US008206899B2

(12) United States Patent
Stearns et al.

(10) Patent No.: US 8,206,899 B2
(45) Date of Patent: Jun. 26, 2012

(54) PROSTATE CANCER-RELATED COMPOSITIONS, METHODS AND KITS BASED ON DNA MICROARRAY PROTEOMICS PLATFORMS

(75) Inventors: Mark Stearns, Villanova, PA (US); Youji Hu, Gulph Mills, PA (US); Min Wang, Gulph Mills, PA (US)

(73) Assignee: Philadelphia Health and Education Corporation, Philadelphia, PA (US)

( * ) Notice: Subject to any disclaimer, the term of this patent is extended or adjusted under 35 U.S.C. 154(b) by 0 days.

(21) Appl. No.: 13/011,792

(22) Filed: Jan. 21, 2011

(65) Prior Publication Data

US 2011/0111979 A1     May 12, 2011

Related U.S. Application Data

(60) Division of application No. 12/782,599, filed on May 18, 2010, now Pat. No. 7,939,274, which is a division of application No. 10/140,602, filed on May 7, 2002, now Pat. No. 7,790,861, which is a continuation-in-part of application No. 09/813,380, filed on Mar. 21, 2001, now abandoned, which is a continuation-in-part of application No. PCT/US02/08673, filed on Mar. 21, 2002, which is a continuation-in-part of application No. 10/098,992, filed on Mar. 15, 2002, which is a continuation of application No. PCT/US00/25981, filed on Sep. 21, 2000.

(60) Provisional application No. 60/155,865, filed on Sep. 24, 1999.

(51) Int. Cl.
| | |
|---|---|
| *C12Q 1/00* | (2006.01) |
| *C12Q 1/68* | (2006.01) |
| *G01N 1/00* | (2006.01) |
| *G01N 33/48* | (2006.01) |
| *G01N 33/567* | (2006.01) |
| *G01N 33/574* | (2006.01) |

(52) U.S. Cl. .............. 435/6; 435/4; 435/7.21; 435/7.23; 436/63; 436/64; 436/174

(58) Field of Classification Search .................. None
See application file for complete search history.

(56) References Cited

U.S. PATENT DOCUMENTS

| | | |
|---|---|---|
| 5,866,325 A | 2/1999 | Sukhatme |
| 5,869,241 A | 2/1999 | Edwards et al. |
| 6,010,849 A | 1/2000 | Edwards et al. |
| 6,066,452 A | 5/2000 | Weissman et al. |
| 6,294,343 B1 | 9/2001 | Mack et al. |
| 6,812,339 B1 | 11/2004 | Venter et al. |
| 7,754,435 B2 | 7/2010 | Stearns et al. |
| 2005/0142592 A1 | 6/2005 | Stearns et al. |
| 2009/0054300 A1 | 2/2009 | Abbas et al. |

FOREIGN PATENT DOCUMENTS

| | | |
|---|---|---|
| WO | 01/21828 A1 | 3/2001 |
| WO | 01/57190 A2 | 8/2001 |

OTHER PUBLICATIONS

Aguilera et al., "A pre-B cell nuclear protein that specifically interacts with the immunoglobulin V-J recombination sequences," 1987, *Cell*, 51:909-917.
Chan et al., "Zinc finger-like motifs in rat ribosomal proteins S27 and S29," 1993, *Nucleic Acids Res.*, 21:649-655.
Chan et al., "The Primary Structure of Rat Ribosomal Protein L10: Relationship to a Jun-Binding Protein and to a Putative Wilms' Tumor Suppressor," 1996, *Biochem. and Biophys. Res. Comm.*, 225:952-956.
Chan et al., "The Primary Structures of Rat Ribosomal Proteins S3a (The V-Fos Transformation Effector) and of S3b," 1996, *Biochem. and Biophys. Res. Comm.*, 228:141-147.
Chiao et al., "Elevated expression of the ribosomal protein S2 gene in human tumors," 1992, *Mol. Carcinog.*, 5:219-231.
Clackson et al., "Making antibody fragments using phage display libraries," 1991, *Nature*, 352:624-628.
Early et al., "An immunoglobulin heavy chain variable region gene is generated from three segments of DNA: $V_H$, D and $J_H$," 1980, *Cell*, 19:981-992.
Fernandez-Pol et al., A growth factor-inducible gene encodes a novel nuclear protein with zinc finger structure, 1993, *J. Biol. Chem.*, 268:21198-211204.
Fernandez-Pol et al., "Metallopanstimulin gene product produced in a baculovirus expression system is a nuclear phosphoprotein that binds to DNA," 1994, *Cell Growth & Differentiation*, 5:811-825.
Fernandez-Pol et al., "Metallopanstimulin gene product produced in a baculovirus expression system is a nuclear phosphoprotein that binds to DNA," 1996, *Anticancer Res.*, 16:2177-2186.
GenCore amino acid database. Alignment between Applicants' SEQ ID No. 2 and U.S. Patent Application sequence 9021 (filed Sep. 10, 2001).
GenCore amino acid database. Alignment between Applicants' SEQ ID No. 2 and WO document No. WO 200157190 A2 sequence 3595 (filed Feb. 5, 2001).
Halligan et al., "Identification of a DNA binding protein that recognizes the nonamer recombinational signal sequence of immunoglobulin genes," 1987, *Proc. Natl. Acad. Sci. USA*, 84:7019-7023.
Hamaguchi et al., "Purification and characterization of a protein that binds to the recombination signal sequence of the immunoglobulin $J_x$ segment," 1989, *Nucleic Acid Res.*, 17:9015-9026.

(Continued)

*Primary Examiner* — Alana H Dent
(74) *Attorney, Agent, or Firm* — Riverside Law LLP

(57) ABSTRACT

The invention relates to novel nucleic acids encoding a mammalian PCADM-1 gene, and proteins encoded thereby, whose expression is increased in certain diseases, disorders, or conditions, including, but not limited to, prostate cancer. The invention further relates to methods of detecting and treating prostate cancer, comprising modulating or detecting PCADM-1 expression and/or production and activity of PCADM-1 polypeptide. Further, the invention relates to novel assays for the identification of DNA-binding proteins and the double-stranded oligonucleotide sequences that specifically bind with them. Finally, the invention relates to DNAZYMs or DNA enzymes which specifically bind PCADM-1 mRNA to inhibit PCADM-1 gene expression and thereby destroy tumor cells and tumor tissue.

6 Claims, 5 Drawing Sheets

OTHER PUBLICATIONS

Mak, 1994, "The V(D)J recombination signal sequence and χB binding protein Rc binds DNA as dimers and forms multimeric structures with its DNA ligands," *Nucleic Acid Res.*, 22:383-390.

Rabbitts et al., 1991, *Advances in Immunology*, 50:119-146.

Rabbitts, 1991, *Cell*, 61:641-644.

Vaarala et al., "Several genes encoding ribosomal proteins are over-expressed in prostate-cancer cell lines: Confirmation of L7a and L37 over-expression in prostate-cancer tissue samples," 1998, *Int. J. Cancer*, 78:27-32.

Wool et al., "Structure and evolution of mammalian ribosomal proteins," 1995, *Biochemistry & Cell Biology*, 73:933-947.

Wool, "Extraribosomal functions of ribosomal proteins," 1996, *Trends in Biochemical Sciences*, 21:164-165.

Wool, 1997, In: The Ribosomal RNA and Group I Introns, pp. 159-178, Green and Schroeder, eds. R.G. Landes Co., Austin, TX.

5'- GCACGAGGGATGACGCCGGTGCAGCGGGGGGGCCCGGG
GGCCCTGGTGGCCCTGGG
ATG GGG AAC CGC GGT GGC TTC CGC GGA GGT TTC GGC AGT GGC ATC
CGG GGC CGG GGT CGC GGC CGT GGA CGG GGC CGG GGC CGA GGC CGC
GGA GCT CGC GGA GGC AAG GCC GAG GAT AAG GAG TGG ATG CCC GTC
ACC AAG TTG GGC CGC TTG GTC AAG GAC ATG AAG ATC AAG TCC CTG
GAG GAG ATC ACT CTC TTC TCC CTG CCC ATT AAG GAA TCA GAG ATC
ATT GAT TTC TTC CTG GGG GCC TCT CTC AAG GAT GAG GTT TTG AAG ATT
ATG CCA GTG CAG AAG CAG ACC CGT GCC GGC CAG CGC ACC AGG TTC
AAG GCA TTT GTT GCT ATC GGG GAC TAC AAT GGC CAC GTC GGT CTG
GGT GTT AAG TGC TCC AAG GAG GTG GCC ACC GCC ATC CGT GGG GCC
ATC ATC CTG GCC AAG CTC TCC ATC GTC CCC GTG CGC AGA GGC TAC
TGG GGG AAC AAC ATC GGC AAG GCC CAC ACT GTC CGT TGC AAG GTG
ACA GGC CGC TGC GGC TCT GTG CTG GTA CGC CTC ATC CCT GCA CCC
AGG GGC ACT GGC ATC GTC TCC GCA CCT GTG CCT AAG AAG CTG CTC
ATG ATG GCT GGT ATC GAT GAC TGC TAC ACC TCA GCC CGG GGC TGC
ACT GCC ACC CTG GGC AAC TTC ACC AAG GCC ACC TTT GAT GCC ATT
TCT AAG ACC TAC AGC TAC CTG ACC CCC GAC CTC TGG AAG GAG ACT
GTA TTC ACC AAG TCT CCC TAT CAG GAG TTC ACT GAC CAC CTC GTC
AAG ACC CAC ACC AGA GTC TCC GTG CAG CGG ACT CAG GCT CCA GCT
GTG GCT ACA ACA *
TAG GGT TTT TAT ACC CAA GAA AAG AAA AAT AAA – 3'

MGNRGGFRGGFGSGIRGRGRGRGRGRGRGARGGKAED
KEWMPVTKLGRLVKDMKIKSLEEITLFSLPIKESEIIDFFLGA
SLKDEVLKIMPVQKQTRAGQRTRFKAFVAIGDYNGHVGLG
VKCSKEVATAIRGAIILAKLSIVPVRRGYWGNNIGKAHTVR
CKVTGRCGSVLVRLIPAPRGTGIVSAPVPKKLLMMAGIDDC
YTSARGCTATLGNFTKATFDAISKTYSYLTPDLWKETVFTK
SPYQEFTDHLVKTHTRVSVQRTQAPAVATT

Sequence of PCADM-1 DNA ZYM-1 and diagram depicting alignment of binding arms with target sequence of PCADM-1

5'- GATCTTCAGGCTAGCTACAACGAGTCCTTG (SEQ ID NO:9)

Sequence of PCADM-1 DNA ZYM-2 and diagram depicting alignment of binding arms with target sequence of PCADM-1

5'- GTTCCCCAGGCTAGCTACAACGACCCAGGGC (SEQ ID NO:10)

PROSTATE CANCER-RELATED COMPOSITIONS, METHODS AND KITS BASED ON DNA MICROARRAY PROTEOMICS PLATFORMS

CROSS-REFERENCE TO RELATED APPLICATIONS

The present application is a divisional of U.S. application Ser. No, 12/782,599, filed May 18, 2010, now issued as U.S. Pat. No. 7,939,274, which is itself a divisional of U.S. application Ser. No. 10/140,602, filed May 7, 2002, now issued as U.S. Pat. No. 7,790,861, which is itself a continuation-in-part of U.S. application Ser. No. 09/813,380, filed Mar. 21, 2001, now abandoned which is a continuation-in-part of PCT Application No. PCT/US02/08673, filed Mar. 21, 2002, which is a continuation-in-part of U.S. application Ser. No. 10/098,992, filed Mar. 15, 2002, which is a continuation of PCT Application No. PCT/US00/25981, filed Sep. 21, 2000, which is entitled to priority under 35 U.S.C. §119(e) to U.S. Provisional Application No. 60/155,865, filed on Sep. 24, 1999, all of which are hereby incorporated by reference in their entireties herein.

STATEMENT REGARDING FEDERALLY SPONSORED RESEARCH OR DEVELOPMENT

This invention was made with government support under Grant No. RFA CA99-007, awarded by the National Institutes of Health (National Cancer Institutes). The U.S. Government therefore has certain rights in this invention.

BACKGROUND OF THE INVENTION

The prior art suggests that ribosomal proteins might play an important role in certain diseases, disorders or conditions. More specifically, there are many reports demonstrating a connection between over expression of the mRNA of genes encoding ribosomal proteins and cancer (Chiao et al., 1992, Mol. Carcinog. 5:219-231; Fernandez-Pol et al., 1993, J. Biol. Chem. 268:21198-211204; Fernandez-Pol et al., 1994, Cell Growth & Differentiation 5:821-825; Fernandez-Pol, 1996, Anticancer Res. 16:2177-2186; Chan et al., 1996, Biochem. and Biophys. Res. Comm. 228:141-147; Chan et al., 1996, Biochem. and Biophys. Res. Comm. 225:952-956; Wool, 1996, Trends in Biochemical Sciences 21:164-165; Wool et al., 1995, Biochem. Cell Biol. 73:933-947; and Vaarala et al., 1998, Int. J. Cancer 78:27-32). For instance, Chiao et al. (1992, Mol. Carcinog. 5:219-231) determined that expression of the S2-ribosomal protein mRNA was elevated in head and neck cancer, but the S2 mRNA was barely detectable in normal tissue. Based upon these studies, it is believed that the over expression of several ribosomal mRNA's might thereby be associated with the development of cancer. For example, it has been proposed that specific zinc finger, leucine zipper motifs, bZIP elements, helix-turn-helix motifs or other motifs characteristic of several ribosomal proteins (e.g., *e. coli* L7, rat S27 and S29) may bind to nucleic acids (Chan et al. Nucleic Acids Res. 1993; 21:649-655; Fernandez-Pol et al., 1996, Anticancer Res. 16:2177-2186; Wool, 1996, Trends in Biochemical Sciences 21:164-165; Wool, 1997, In: The ribosomal RNA and Group I introns, pp. 153-178, Green and Schroeder, eds., R.G. Landes Co., Austin, Tex.). Others have found that the rat ribosomal protein S3a is identical to the rat v-fos transformation effector protein (Chan et al., 1996, Biochem. Biophys. Res. Comm. 228:141-147). S3a is normally involved in initiation of protein synthesis and is also related to proteins involved in the regulation of growth and the cell cycle (Chan et al., 1996, Biochem. and Biophys. Res. Comm. 228:141-147). Likewise, the rat ribosomal protein L10 is homologous to a putative Wilm's tumor suppressor gene (Chan et al., 1996, Biochem. Biophys. Res. Comm. 225:952-956). Malignant cells may express mutant 'ribosomal-like' proteins. However, there is currently no evidence that any of these ribosomal proteins are over expressed or that the proteins acquire DNA binding activities in malignant cells.

The existence of chromosomal abnormalities in lymphoid tumors is well established. Chromosomal translocations associated with T cell acute lymphoblastic leukemia (T-ALL) have led to the identification of several potential oncogenes (Rabbitts, 1991, Cell 67:641-644). Many of the T-ALL associated chromosomal translocations have been localized to the T-cell receptor (TCR) genes. Recombination of the immunoglobulin gene takes place at early phase of B-lymphocyte differentiation. The V-(D)-J recombination that joins two or three germline segments (i.e., variable-V; diversity-D; and joining-J) segments into a variable-gene exon by site-specific recombination contributes to amplification of the V-region diversity. Comparison of the nucleotide sequences of the flanking regions of the V, D, and J segments has demonstrated that two common blocks of nucleotide sequences are conserved (Early et al., 1980, Cell 19:981-992), including a heptamer CACTGTG and a T-rich nonamer GGTTTTTGT, which are separated by a spacer sequence of either 12 or 23 bases. The homology between the heptamer-spacer-heptamer-nonamer sequences of the T-cell receptor and immunoglobulin genes suggests that these elements, commonly referred to as Break Point Cluster Regions or BPCRs, play an important role in V-(D)-J recombination.

The prior art suggests that DNA binding protein(s) that recognize the conserved recombination signal sequence (RS) may be involved in the recombinational machinery that cleaves DNA at the juncture between the signal and coding region sequences and ligates the cleaved ends. Earliest reports disclosed RS proteins as being located in lymphoid cells (Aguilera et al., 1987, Cell 51:909-917; Halligan and Desiderio, 1987, Proc. Natl. Acad. Sci. USA 84:7019-7023; Hamaguchi et al., 1989, Nucleic Acid Res. 17:9015-9026; and Mak, 1994, Nucleic Acid Res. 22:383-390). More recently, different RS proteins have been identified. For example, a DNA binding protein for kappaB binding and recognition component of the V(D)J recombination signal sequence has been identified. Activation of this family of transcription factors is thought to provide a mechanism by which oncogenic tyrosine kinases regulate genes with kappaB-controlled gene regulatory elements.

Studies on T cell abnormalities have been particularly informative with respect to recombinase involvement, especially with respect to breakpoints within the chromosome band 11p13. It seems that recombinase is responsible for abnormal chromosomal unions, because often both reciprocal translocated chromosomes have N-region nucleotide addition, which is a hallmark of recombinase activity (Alt and Baltimore, 1982, Proc. Natl. Acad. Sci. USA 79:4118-4123). These translocations are regarded as mutations of the normal chromosomal joining process.

In sum, the mechanism(s) by which chromosomal abnormalities associated with rearranging genes come about and the role of DNA binding enzymes involved in the normal antigen receptor gene rearrangement (i.e., recombinases) (Croce, 1987, Cell 49:155-169), albeit well-studied, are still poorly understood. Thus, identification of new BPCRs and new recombinases is needed, especially for understanding non-lymphoid type diseases and solid cancer development.

Further, although prior studies suggest that DNA binding proteins are associated with and/or mediate certain diseases, disorders or conditions, very few of these proteins have been identified (e.g., to date, none have been identified in solid cancers) and their role(s) in the disease process is poorly understood. This is so despite the fact that there are various prior art assays for identification of DNA binding proteins (e.g., Weissman et al., 2000, U.S. Pat. No. 6,066,452; Edwards et al., 2000, U.S. Pat. No. 6,010,849; Edwards et al., 1999, U.S. Pat. No. 5,869,241; Sukhatme, 1999, U.S. Pat. No. 5,866,325). Thus, there is a long-felt need for a simple, effective assay for the identification of DNA binding proteins and their cognate duplex DNA sequence binding sites.

In addition, despite the potential usefulness of DNA binding proteins in the diagnosis and the development of therapeutics, there are few, if any, diagnostics and therapeutics based on DNA binding proteins or their cognate binding DNA duplexes.

Although prostate cancer is one of the leading causes of cancer-related mortality and morbidity in men, there are few effective diagnostics and therapeutics for this disease, and none are based on detection of a DNA binding protein, including proteins, which bind BPCRs. To date, there have been approximately 450 partially characterized tissue markers identified in the scientific literature, but only one has been developed as a clinical marker approved by the FDA, i.e., prostate specific antigen (PSA) and it's derivatives. Despite the dearth of useful markers for diagnosis and detection of cancers, including, but not limited to, prostate cancer, development of markers for the early detection of cancers is essential to improved treatment of cancer.

With respect to prostate cancer, it is generally believed that serum prostate specific antigen (PSA) levels are neither sensitive nor specific for identification of patients with prostate cancer (Garnick and Fair, 1998, Scientific Amer. December: 75-83). It has been estimated that as many as 40% of men with prostate cancer have normal PSA levels (i.e. false negatives) and conversely, 30% of men with elevated PSA levels do not have PCA. Thus, development of more sensitive and specific assays for cancer, including prostate cancer, is imperative. Further, non-invasive and inexpensive urine-based screening assays, which would enable widespread implementation through mass community screening programs or in routine clinical examinations, would be particularly useful in diagnosis and treatment of cancers, including prostate cancer.

In sum, there is a long felt and acute need for identification and characterization of DNA binding proteins and the cognate duplex DNA molecules they specifically bind, especially for the development of diagnostics and therapeutics for diseases, disorders or conditions associated with altered expression of a DNA binding protein. Further, there is a long-felt and acute need for improved diagnostics and therapeutics related to cancer, including prostate cancer. The present invention meets these needs.

BRIEF SUMMARY OF THE INVENTION

The invention includes an isolated nucleic acid encoding a mammalian prostate cancer antigen diagnostic marker 1 (PCADM-1), or a fragment thereof.

The invention also includes an isolated nucleic acid encoding a mammalian prostate cancer antigen diagnostic marker 1, and homologs, variants, mutants and fragments thereof.

In one aspect, the isolated nucleic acid encoding a mammalian prostate cancer antigen diagnostic marker 1 (PCADM-1), or a fragment thereof, shares greater than 99% sequence identity with a nucleic acid encoding a human prostate cancer antigen diagnostic marker 1 (SEQ ID NO:1).

In another aspect, the isolated nucleic acid comprises an adenine at nucleotide number 190, a cytosine at nucleotide number 191, a cytosine at nucleotide number 465, a guanine at nucleotide number 475, a guanine at nucleotide number 488, and a cytosine at nucleotide number 505 relative to SEQ ID NO:1.

The invention includes an isolated nucleic acid encoding a mammalian prostate cancer antigen diagnostic marker 1, wherein the sequence of the nucleic acid consists of the sequence of SEQ ID NO:1.

In another aspect, the isolated nucleic acid encoding a mammalian prostate cancer antigen diagnostic marker 1 (PCADM-1), or a fragment thereof, further comprises a nucleic acid encoding a tag polypeptide covalently linked thereto.

In yet another aspect, the tag polypeptide is selected from the group consisting of a myc tag polypeptide, a glutathione-S-transferase tag polypeptide, a green fluorescent protein tag polypeptide, a myc-pyruvate kinase tag polypeptide, a His6 tag polypeptide, an influenza virus hemagglutinin tag polypeptide, a flag tag polypeptide, and a maltose binding protein tag polypeptide.

In one aspect, the isolated nucleic acid encoding a mammalian prostate cancer antigen diagnostic marker 1 (PCADM-1), or a fragment thereof, further comprises a nucleic acid specifying a promoter/regulatory sequence operably linked thereto.

The invention includes a vector comprising an isolated nucleic acid encoding a mammalian prostate cancer antigen diagnostic marker 1, or a fragment thereof. In one aspect, the invention includes a recombinant cell comprising the vector.

In another aspect, the vector further comprises a nucleic acid specifying a promoter/regulatory sequence operably linked to the isolated nucleic acid encoding a mammalian cancer diagnostic marker 1, or fragment thereof.

In yet another aspect, the isolated nucleic acid encoding a mammalian prostate cancer antigen diagnostic marker 1 is expressed when introduced into a cell.

The invention includes a recombinant cell comprising an isolated nucleic acid encoding a mammalian prostate cancer antigen diagnostic marker 1, or a fragment thereof.

The invention also includes a recombinant cell comprising a vector comprising an isolated nucleic acid encoding a mammalian prostate cancer antigen diagnostic marker 1, or a fragment thereof, where the vector further comprises a nucleic acid specifying a promoter/regulatory sequence operably linked to the isolated nucleic acid encoding a mammalian cancer diagnostic marker 1, or fragment thereof.

The invention includes an isolated nucleic acid complementary to an isolated nucleic acid encoding a mammalian prostate cancer antigen diagnostic marker 1, or a fragment thereof, the complementary nucleic acid being in an antisense orientation.

In one aspect, the isolated nucleic acid shares greater than 99% identity with a nucleic acid complementary with a nucleic acid having the sequence of a human prostate cancer antigen diagnostic marker 1 (SEQ ID NO:1).

In another aspect, the isolated nucleic acid further comprises a nucleic acid specifying a promoter/regulatory sequence operably linked thereto.

In yet another aspect, the isolated nucleic acid is expressed when introduced into a cell.

The invention includes a vector comprising an isolated nucleic acid complementary to an isolated nucleic acid encoding a mammalian prostate cancer antigen diagnostic marker 1, or a fragment thereof, the complementary nucleic acid being in an antisense orientation, wherein the isolated nucleic acid encoding a mammalian prostate cancer antigen diagnostic marker 1, or a fragment thereof, shares greater than 99% identity with a nucleic acid complementary with a nucleic acid having the sequence of a human prostate cancer antigen diagnostic marker 1 (SEQ ID NO:1).

The invention includes a vector comprising an isolated nucleic acid complementary to an isolated nucleic acid encoding a mammalian prostate cancer antigen diagnostic marker 1, or a fragment thereof, the complementary nucleic acid being in an antisense orientation, the isolated nucleic acid further comprising a nucleic acid specifying a promoter/regulatory sequence operably linked thereto, further wherein the isolated nucleic acid is expressed when introduced into a cell.

The invention further includes a recombinant cell comprising an isolated nucleic acid complementary to an isolated nucleic acid encoding a mammalian prostate cancer antigen diagnostic marker 1, or a fragment thereof, the complementary nucleic acid being in an antisense orientation.

The invention includes a recombinant cell comprising an isolated nucleic acid complementary to an isolated nucleic acid encoding a mammalian prostate cancer antigen diagnostic marker 1, or a fragment thereof, the complementary nucleic acid being in an antisense orientation, wherein the isolated nucleic acid shares greater than 99% identity with a nucleic acid complementary with a nucleic acid having the sequence of a human prostate cancer antigen diagnostic marker 1 (SEQ ID NO:1).

The invention includes a recombinant cell comprising a vector comprising an isolated nucleic acid complementary to an isolated nucleic acid encoding a mammalian prostate cancer antigen diagnostic marker 1, or a fragment thereof, said complementary nucleic acid being in an antisense orientation, wherein said isolated nucleic acid encoding a mammalian prostate cancer antigen diagnostic marker 1, or a fragment thereof, shares greater than 99% identity with a nucleic acid complementary with a nucleic acid having the sequence of a human prostate cancer antigen diagnostic marker 1 (SEQ ID NO:1).

The invention includes a recombinant cell comprising a vector, the vector comprising an isolated nucleic acid complementary to an isolated nucleic acid encoding a mammalian prostate cancer antigen diagnostic marker 1, or a fragment thereof, said complementary nucleic acid being in an antisense orientation, said isolated nucleic acid further comprising a nucleic acid specifying a promoter/regulatory sequence operably linked thereto, further wherein said isolated nucleic acid is expressed when introduced into a cell.

The invention includes an isolated nucleic acid encoding a mammalian prostate cancer antigen diagnostic marker 1, wherein the amino acid sequence of the prostate cancer antigen diagnostic marker 1 shares greater than 99% sequence identity with the amino acid sequence SEQ ID NO:2.

In one aspect, amino acid sequence of the prostate cancer antigen diagnostic marker 1 comprises an threonine (T) at amino acid residue number 64, an asparagine (N) at amino acid residue number 155, an alanine (A) at residue number 159, an arginine (R) at residue number 163, and an arginine (R) at residue number 169 relative to the amino acid sequence of SEQ ID NO:2.

The invention includes an isolated nucleic acid encoding a mammalian prostate cancer antigen diagnostic marker 1, wherein the amino acid sequence of the prostate cancer antigen diagnostic marker 1 consists of the sequence of SEQ ID NO:2.

In one aspect, the nucleic acid further comprises a nucleic acid encoding a tag polypeptide covalently linked thereto.

In another aspect, the tag polypeptide is selected from the group consisting of a myc tag polypeptide, a glutathione-S-transferase tag polypeptide, a green fluorescent protein tag polypeptide, a myc-pyruvate kinase tag polypeptide, a His6 tag polypeptide, an influenza virus hemagglutinin tag polypeptide, a flag tag polypeptide, and a maltose binding protein tag polypeptide.

In yet another aspect, the nucleic acid further comprises a nucleic acid encoding a promoter/regulatory sequence operably linked thereto.

The invention includes a vector comprising an isolated nucleic acid encoding a mammalian prostate cancer antigen diagnostic marker 1, wherein the amino acid sequence of the prostate cancer antigen diagnostic marker 1 shares greater than 99% sequence identity with the amino acid sequence SEQ ID NO:2, and wherein the amino acid sequence of the prostate cancer antigen diagnostic marker 1 comprises a threonine (T) at amino acid residue number 64, an asparagine (N) at amino acid residue number 155, an alanine (A) at residue number 159, an arginine (R) at residue number 163, and an arginine (R) at residue number 169 relative to the amino acid sequence of SEQ ID NO:2.

In one aspect, the vector further comprises a nucleic acid specifying a promoter/regulatory sequence operably linked thereto.

In another aspect, the isolated nucleic acid encoding a mammalian prostate cancer antigen diagnostic marker 1 is expressed when introduced into a cell.

The invention includes a recombinant cell comprising an isolated nucleic acid encoding a mammalian prostate cancer antigen diagnostic marker 1, wherein the amino acid sequence of the prostate cancer antigen diagnostic marker 1 shares greater than 99% sequence identity with the amino acid sequence SEQ ID NO:2.

The invention also includes a recombinant cell comprising an isolated nucleic acid encoding a mammalian prostate cancer antigen diagnostic marker 1, wherein the amino acid sequence of the prostate cancer antigen diagnostic marker 1 shares greater than 99% sequence identity with the amino acid sequence SEQ ID NO:2, and wherein the amino acid sequence of the prostate cancer antigen diagnostic marker 1 comprises a threonine (T) at amino acid residue number 64, an asparagine (N) at amino acid residue number 155, an alanine (A) at residue number 159, an arginine (R) at residue number 163, and an arginine (R) at residue number 169 relative to the amino acid sequence of SEQ ID NO:2.

The invention includes a recombinant cell comprising an isolated nucleic acid encoding a mammalian prostate cancer antigen diagnostic marker 1, wherein the amino acid sequence of the prostate cancer antigen diagnostic marker 1 consists of the sequence of SEQ ID NO:2, the nucleic acid further comprising a nucleic acid encoding a tag polypeptide covalently linked thereto, wherein the tag polypeptide is selected from the group consisting of a myc tag polypeptide, a glutathione-S-transferase tag polypeptide, a green fluorescent protein tag polypeptide, a myc-pyruvate kinase tag polypeptide, a His6 tag polypeptide, an influenza virus hemagglutinin tag polypeptide, a flag tag polypeptide, and a maltose binding protein tag polypeptide, and the nucleic acid further comprising a nucleic acid encoding a promoter/regulatory sequence operably linked thereto.

The invention includes a recombinant cell comprising a vector comprising an isolated nucleic acid encoding a mammalian prostate cancer antigen diagnostic marker 1, wherein the amino acid sequence of the prostate cancer antigen diagnostic marker 1 shares greater than 99% sequence identity with the amino acid sequence SEQ ID NO:2, and wherein said amino acid sequence of the prostate cancer antigen diagnostic marker 1 comprises a threonine (T) at amino acid residue number 64, an asparagine (N) at amino acid residue number 155, an alanine (A) at residue number 159, an arginine (R) at residue number 163, and an arginine (R) at residue number 169 relative to the amino acid sequence of SEQ ID NO:2.

In one aspect, the vector is expressed when introduced into the cell.

The invention includes an isolated nucleic acid complementary to an isolated nucleic acid encoding a mammalian prostate cancer antigen diagnostic marker 1, wherein the amino acid sequence of the prostate cancer antigen diagnostic marker 1 shares greater than 99% sequence identity with the amino acid sequence SEQ ID NO:2, the complementary nucleic acid being in an antisense orientation.

In one aspect, the complementary nucleic acid further comprises a nucleic acid specifying a promoter/regulatory sequence operably linked thereto.

The invention includes a vector comprising an isolated nucleic acid complementary to an isolated nucleic acid encoding a mammalian prostate cancer antigen diagnostic marker 1, wherein the amino acid sequence of the prostate cancer antigen diagnostic marker 1 shares greater than 99% sequence identity with the amino acid sequence SEQ ID NO:2, the complementary nucleic acid being in an antisense orientation.

The invention includes a vector comprising an isolated nucleic acid complementary to an isolated nucleic acid encoding a mammalian prostate cancer antigen diagnostic marker 1, wherein the amino acid sequence of the prostate cancer antigen diagnostic marker 1 shares greater than 99% sequence identity with the amino acid sequence SEQ ID NO:2, the complementary nucleic acid being in an antisense orientation, wherein the isolated nucleic acid is expressed when introduced into a cell.

The invention includes an isolated nucleic acid complementary to an isolated nucleic acid encoding a mammalian prostate cancer antigen diagnostic marker 1, wherein the amino acid sequence of the prostate cancer antigen diagnostic marker 1 shares greater than 99% sequence identity with the amino acid sequence SEQ ID NO:2, the complementary nucleic acid being in an antisense orientation, and wherein the nucleic acid shares greater than 99% identity with a nucleic acid complementary with a nucleic acid having the sequence of a human prostate cancer antigen diagnostic marker 1 (SEQ ID NO:1).

In one aspect, the isolated nucleic acid further comprises a nucleic acid specifying a promoter/regulatory sequence operably linked thereto.

The invention includes a vector comprising an isolated nucleic acid complementary to an isolated nucleic acid encoding a mammalian prostate cancer antigen diagnostic marker 1, wherein the amino acid sequence of the prostate cancer antigen diagnostic marker 1 shares greater than 99% sequence identity with the amino acid sequence SEQ ID NO:2, the complementary nucleic acid being in an antisense orientation, and wherein the nucleic acid shares greater than 99% identity with a nucleic acid complementary with a nucleic acid having the sequence of a human prostate cancer antigen diagnostic marker 1 (SEQ ID NO:1).

The invention includes a vector comprising an isolated nucleic acid complementary to an isolated nucleic acid encoding a mammalian prostate cancer antigen diagnostic marker 1, wherein the amino acid sequence of the prostate cancer antigen diagnostic marker 1 shares greater than 99% sequence identity with the amino acid sequence SEQ ID NO:2, the complementary nucleic acid being in an antisense orientation, and wherein the nucleic acid shares greater than 99% identity with a nucleic acid complementary with a nucleic acid having the sequence of a human prostate cancer antigen diagnostic marker 1 (SEQ ID NO:1), and the isolated nucleic acid further comprises a nucleic acid specifying a promoter/regulatory sequence operably linked thereto.

In one aspect, the isolated nucleic acid is expressed when introduced into a cell.

The invention includes a recombinant cell comprising an isolated nucleic acid complementary to an isolated nucleic acid encoding a mammalian prostate cancer antigen diagnostic marker 1, wherein the amino acid sequence of said prostate cancer antigen diagnostic marker 1 shares greater than 99% sequence identity with the amino acid sequence SEQ ID NO:2, the complementary nucleic acid being in an antisense orientation, wherein said nucleic acid shares greater than 99% identity with a nucleic acid complementary with a nucleic acid having the sequence of a human prostate cancer antigen diagnostic marker 1 (SEQ ID NO:1).

The invention includes a recombinant cell comprising an isolated nucleic acid complementary to an isolated nucleic acid encoding a mammalian prostate cancer antigen diagnostic marker 1, wherein the amino acid sequence of said prostate cancer antigen diagnostic marker 1 shares greater than 99% sequence identity with the amino acid sequence SEQ ID NO:2, the complementary nucleic acid being in an antisense orientation, wherein said nucleic acid shares greater than 99% identity with a nucleic acid complementary with a nucleic acid having the sequence of a human prostate cancer antigen diagnostic marker 1 (SEQ ID NO:1), the isolated nucleic acid further comprising a nucleic acid specifying a promoter/regulatory sequence operably linked thereto.

In one aspect, the nucleic acid is expressed in the cell.

The invention includes an isolated polypeptide comprising a mammalian prostate cancer antigen diagnostic marker 1.

In one aspect, the mammalian prostate cancer antigen diagnostic marker 1 shares at least 99% sequence identity with an amino acid of SEQ ID NO:2.

In another aspect, the polypeptide comprises an threonine at amino acid residue number 64, an asparagine at amino acid residue number 155, an alanine at residue number 159, an arginine at residue number 163, and an arginine at residue number 169 relative to the amino acid sequence of SEQ ID NO:2.

The invention includes an isolated polypeptide comprising a mammalian prostate cancer antigen diagnostic marker 1, wherein the amino acid sequence of the isolated polypeptide consists of SEQ ID NO:2.

The invention includes an isolated nucleic acid that specifically binds with a prostate cancer antigen diagnostic marker 1 polypeptide.

In one aspect, the nucleic acid is a double-stranded DNA.

In another aspect, the isolated nucleic acid comprises a nucleic acid sequence selected from the group consisting of a nucleic acid sequence CACGGATG (SEQ ID NO:5), a nucleic acid sequence CACAATGA (SEQ ID NO:6), a nucleic acid sequence CACAATG (SEQ ID NO:7), and a nucleic acid sequence CACAATGTTTTTGT (SEQ ID NO:8).

The invention includes an isolated nucleic acid that specifically binds with a mammalian leukemia cell break point cluster region binding protein.

In one aspect, the leukemia break point cluster region binding protein is selected from the group consisting of a Rag 1 protein and a Rag 2 protein.

In yet another aspect, the isolated nucleic acid comprises a double-stranded DNA, the DNA comprising a nucleic acid sequence selected from the group consisting of a nucleic acid sequence CACGGATG (SEQ ID NO:5), and a nucleic acid sequence CACAATGA (SEQ ID NO:6).

The invention includes an isolated nucleic acid that specifically binds with a prokaryotic break point cluster region binding protein.

In one aspect, the prokaryotic break point cluster region binding protein is selected from the group consisting of a RecA protein and a RecB protein.

In another aspect, the polypeptide specifically binds with at least one of a nucleic acid selected from the group consisting of a nucleic acid consisting of the sequence CACGGATG (SEQ ID NO:5), a nucleic acid consisting of the sequence CACAATGA (SEQ ID NO:6), a nucleic acid consisting of the sequence CACAATG (SEQ ID NO:7), and a nucleic acid consisting of the sequence CACAATGTTTTTGT (SEQ ID NO:8).

The invention includes an isolated enzymatic nucleic acid, wherein the nucleic acid specifically cleaves mRNA transcribed from a nucleic acid encoding a prostate cancer antigen diagnostic marker 1.

In one aspect, the nucleic acid sequence of the isolated enzymatic nucleic acid is selected from the group consisting of the sequence of SEQ ID NO:9 (GATCTTCAGGCTAGCTACAACGAGTCCTTGA) and the sequence of SEQ ID NO:10 (GTTCCCCAGGCTAGCTACAACGACCCAGGGC).

The invention includes an isolated enzymatic nucleic acid, wherein the nucleic acid specifically cleaves mRNA transcribed from a nucleic acid encoding a prostate cancer antigen diagnostic marker 1, and further wherein the sequence of the isolated enzymatic nucleic acid is selected from the group consisting of the sequence of SEQ ID NO:9 and the sequence of SEQ ID NO:10.

The invention also includes an isolated enzymatic nucleic acid wherein the nucleic acid specifically cleaves mRNA transcribed from a nucleic acid encoding a prostate cancer antigen diagnostic marker 1, and further wherein the nucleic acid encoding a prostate cancer antigen diagnostic marker 1 comprises a nucleic acid having the sequence SEQ ID NO:1, or a portion thereof.

In one aspect, the enzymatic nucleic acid comprises at least one binding arm and further wherein said binding arm comprises a sequence complementary to SEQ ID NO:1, or a portion thereof.

In another aspect, the nucleic acid further comprises a nucleic acid specifying a promoter/regulatory sequence operably linked thereto.

In yet another aspect, the nucleic acid comprises a catalytic domain comprising a '10-23' motif structure.

In a further aspect, the enzymatic nucleic acid comprises a catalytic core domain and further comprises at least one binding arm flanking the domain wherein the binding arm comprises from about six to ten nucleotides.

In another aspect, the flanking nucleotides comprise a sequence complementary to SEQ ID NO:1, or a portion thereof.

The invention includes an isolated enzymatic nucleic acid which specifically cleaves mRNA transcribed from a nucleic acid encoding a prostate cancer antigen diagnostic marker 1, wherein the amino acid sequence of the prostate cancer antigen diagnostic marker 1 encoded by the nucleic acid encoding a prostate cancer antigen diagnostic marker 1 shares greater than 99% sequence identity with the amino acid sequence SEQ ID NO:2.

The invention includes an enzymatic nucleic acid, which specifically cleaves mRNA transcribed from a nucleic acid encoding a prostate cancer antigen diagnostic marker 1, the enzymatic nucleic acid comprising the sequence GATCTTCAGGCTAGCTACAACGAGTCCTTGA (SEQ ID NO:9) and the sequence GTTCCCCAGGCTAGCTACAACGACCCAGGGC (SEQ ID NO:10).

The invention includes an isolated enzymatic nucleic acid, which specifically cleaves mRNA transcribed from a nucleic acid encoding a prostate cancer antigen diagnostic marker 1, wherein the nucleic acid sequence of the enzymatic nucleic acid is selected from the group consisting of the sequence of SEQ ID NO:9 and the sequence of SEQ ID NO:10.

In one aspect, the enzymatic nucleic acid comprises a binding arm wherein the binding arm comprises a sequence complementary to SEQ ID NO:1, or a portion thereof.

In another aspect, the binding arm comprises from about 6 to 10 nucleotides.

The invention includes an antibody that specifically binds with a mammalian prostate cancer antigen diagnostic marker 1 polypeptide, or a fragment thereof.

In one aspect, the antibody is selected from the group consisting of a polyclonal antibody, a monoclonal antibody, a humanized antibody, a chimeric antibody, and a synthetic antibody.

The invention includes a composition comprising an antibody that specifically binds with a mammalian prostate cancer antigen diagnostic marker 1 polypeptide, or a fragment thereof, and a pharmaceutically-acceptable carrier.

The invention also includes a composition comprising an isolated nucleic acid encoding a mammalian prostate cancer antigen diagnostic marker 1, or a fragment thereof, and a pharmaceutically-acceptable carrier.

The invention includes a composition comprising an isolated polypeptide comprising a mammalian prostate cancer antigen diagnostic marker 1, and a pharmaceutically-acceptable carrier.

The invention includes a composition comprising an isolated nucleic acid that specifically binds with a prostate cancer antigen diagnostic marker 1 polypeptide and a pharmaceutically-acceptable carrier.

The invention also includes a composition comprising an isolated enzymatic nucleic acid, wherein the isolated enzymatic nucleic acid specifically cleaves mRNA transcribed from a nucleic acid encoding a prostate cancer antigen diagnostic marker 1, and a pharmaceutically-acceptable carrier.

The invention includes a composition comprising an antibody that specifically binds with a mammalian prostate cancer antigen diagnostic marker 1 polypeptide, or a fragment thereof, and a pharmaceutically-acceptable carrier.

The invention includes a transgenic non-human mammal comprising an isolated nucleic acid encoding a mammalian prostate cancer antigen diagnostic marker 1, or a fragment thereof.

The invention includes a method of treating a disease mediated by mal-expression of a prostate cancer antigen diagnostic marker 1 in a mammal. The method comprises administering to a human afflicted with a disease mediated by mal-expression of a prostate cancer antigen diagnostic marker 1 expression-inhibiting amount of at least one substance selected from the group consisting of an isolated nucleic acid complementary to an isolated nucleic acid encoding a mammalian prostate cancer antigen diagnostic marker 1, or a fragment thereof, an isolated enzymatic nucleic acid which specifically cleaves mRNA transcribed from a nucleic acid encoding a prostate cancer antigen diagnostic marker 1, and an antibody that specifically binds with a mammalian prostate cancer antigen diagnostic marker 1.

In one aspect, the disease is prostate cancer.

In another aspect, the mammal is selected from the group consisting of a human and a dog.

In yet another aspect, the method further comprises administering an enzymatic nucleic acid which specifically cleaves mRNA transcribed from a nucleic acid encoding a polypeptide wherein the polypeptide is selected from a group consisting of a vascular epithelial growth factor 1 (VEGF-1) and a metalloproteinase 2 (MMP-2).

The invention includes a method of diagnosing prostate cancer in a mammal. The method comprises obtaining a biological sample from the mammal, assessing the level of PCADM-1 in the biological sample, and comparing the level of PCADM-1 in the biological sample with the level of PCADM-1 in a biological sample obtained from a like mammal not afflicted with prostate cancer, wherein a higher level of PCADM-1 in the biological sample from the mammal compared with the level of PCADM-1 in the biological sample from the like mammal is an indication that the mammal is afflicted with prostate cancer, thereby diagnosing prostate cancer in the mammal.

In one aspect, the mammal is selected from the group consisting of a human and a dog.

In another aspect, the biological sample is selected from the group consisting of a prostate tissue sample, a blood sample, a urine sample, a sputum sample, a peritoneal cavity fluid sample, a perineal cavity fluid sample, a pleural cavity fluid sample, a semen sample, a prostatic fluid sample, a stool sample, and a bone marrow sample.

The invention includes a method of diagnosing prostate cancer in a mammal. The method comprises obtaining a biological sample from the mammal, assessing the level of antibody that specifically binds with prostate cancer antigen diagnostic marker 1 in the biological sample, and comparing the level of antibody that specifically binds with prostate cancer antigen diagnostic marker 1 in the biological sample with the level of antibody that specifically binds with prostate cancer antigen diagnostic marker 1 in a biological sample obtained from a like mammal not afflicted with prostate cancer, wherein a higher level of antibody that specifically binds with prostate cancer antigen diagnostic marker 1 in the biological sample from the mammal compared with the level of antibody that specifically binds with prostate cancer antigen diagnostic marker 1 in the biological sample from the like mammal is an indication that the mammal is afflicted with prostate cancer, thereby diagnosing prostate cancer in a mammal.

In one aspect, the mammal is selected from the group consisting of a human and a dog.

In another aspect, the biological sample is selected from the group consisting of a prostate tissue sample, a blood sample, a urine sample, a sputum sample, a peritoneal cavity fluid sample, a perineal cavity fluid sample, a pleural cavity fluid sample, a semen sample, a prostatic fluid sample, a stool sample, and a bone marrow sample.

The invention includes a method of identifying a test compound that affects expression of prostate cancer antigen diagnostic marker 1 in a cell. The method comprises contacting a cell with a test compound and comparing the level of prostate cancer antigen diagnostic marker 1 expression in the cell with the level of prostate cancer antigen diagnostic marker 1 expression in an otherwise identical cell not contacted with the test compound, wherein a higher or lower level of prostate cancer antigen diagnostic marker 1 expression in the cell contacted with the test compound compared with the level of prostate cancer antigen diagnostic marker 1 expression in the otherwise identical cell not contacted with the test compound is an indication that the test compound affects expression of prostate cancer antigen diagnostic marker 1 in a cell. In one aspect, the invention includes a compound identified by the method.

The invention includes a method of identifying a compound that reduces expression of prostate cancer antigen diagnostic marker 1 in a cell. The method comprises contacting a cell with a test compound and comparing the level of prostate cancer antigen diagnostic marker 1 expression in the cell with the level of prostate cancer antigen diagnostic marker 1 expression in an otherwise identical cell not contacted with the test compound, wherein a lower level of prostate cancer antigen diagnostic marker 1 expression in the cell contacted with the test compound compared with the level of prostate cancer antigen diagnostic marker 1 expression in the otherwise identical cell not contacted with the test compound is an indication that the test compound reduces expression of prostate cancer antigen diagnostic marker 1 in a cell. In one aspect, the invention includes a compound identified by this method.

The invention includes a method of identifying a compound that increases expression of prostate cancer antigen diagnostic marker 1 in a cell. The method comprises contacting a cell with a test compound and comparing the level of prostate cancer antigen diagnostic marker 1 expression in the cell with the level of prostate cancer antigen diagnostic marker 1 expression in an otherwise identical cell not contacted with the test compound, wherein a higher level of prostate cancer antigen diagnostic marker 1 expression in the cell contacted with the test compound compared with the level of prostate cancer antigen diagnostic marker 1 expression in the otherwise identical cell not contacted with the test compound is an indication that the test compound increases expression of prostate cancer antigen diagnostic marker 1 in a cell. In one aspect, the invention includes a compound identified by this method.

The invention includes a method of identifying a compound that affects binding of a prostate cancer antigen diagnostic marker 1 with a double-stranded nucleic acid that specifically binds with prostate cancer antigen diagnostic marker 1. The method comprises comparing the level of prostate cancer antigen diagnostic marker 1 binding with a double-stranded nucleic acid that specifically binds with a prostate cancer antigen diagnostic marker 1 in the presence of a compound with the level of prostate cancer antigen diagnostic marker 1 binding with the double-stranded nucleic acid that specifically binds with a prostate cancer antigen diagnostic marker 1 in the absence of the compound, wherein a higher or lower level of prostate cancer antigen diagnostic marker 1 binding with the double-stranded nucleic acid that specifically binds with a prostate cancer antigen diagnostic marker 1 in the presence of the compound compared with the level of prostate cancer antigen diagnostic marker 1 binding with the double-stranded nucleic acid that specifically binds with a prostate cancer antigen diagnostic marker 1 in the absence of the compound is an indication that the compound affects binding of a prostate cancer antigen diagnostic marker 1 with a double-stranded nucleic acid that specifically binds with prostate cancer antigen diagnostic marker 1, thereby identifying a compound that affects binding of a prostate cancer antigen diagnostic marker 1 with a double-stranded nucleic acid that specifically binds with prostate cancer antigen diagnostic marker 1.

In one aspect, the double-stranded nucleic acid that specifically binds with prostate cancer antigen diagnostic marker 1 has a sequence selected from the group consisting of a sequence CACGGATG (SEQ ID NO:5), a sequence CACAATGA (SEQ ID NO:6), a sequence CACAATG (SEQ ID NO:7), and a sequence CACAATGTTTTTGT (SEQ ID NO:8).

In another aspect, the prostate cancer antigen diagnostic marker 1 has a sequence that shares greater than 99% amino acid homology with sequence SEQ ID NO:2. In yet another aspect, the invention includes a compound identified by the method.

The invention includes a method of monitoring the treatment of a human having prostate cancer. The method comprises:
(a) assessing the level of prostate cancer antigen diagnostic marker 1 in a first biological sample obtained from the human to determine an initial level of prostate cancer antigen diagnostic marker 1;
(b) administering an anti-prostate cancer therapy to the human;
(c) assessing the level of prostate cancer antigen diagnostic marker 1 in a second otherwise identical biological sample obtained from the human during or after the therapy;
(d) comparing the level of prostate cancer antigen diagnostic marker 1 in the first biological sample with the level of prostate cancer antigen diagnostic marker 1 in the second biological sample; and
(e) correlating any reduction in level of prostate cancer antigen diagnostic marker 1 with the effectiveness of the anti-prostate cancer therapy,
thereby monitoring the treatment of a human having prostate cancer.

In one aspect, the method further comprises repeating (b) through (e) during a time period selected from the group consisting of the duration of the prostate cancer, the life of the human, and the period of the anti-prostate cancer therapy.

In another aspect, the level of prostate cancer antigen diagnostic marker 1 is assessed using a method selected from the group consisting of a method of detecting a nucleic acid encoding a prostate cancer antigen diagnostic marker 1, and a method of detecting a prostate cancer antigen diagnostic marker 1.

In yet another aspect, the method of detecting a prostate cancer antigen diagnostic marker 1 is selected from the group consisting of a method of detecting an antibody that specifically binds with a prostate cancer antigen diagnostic marker 1, and a method of detecting binding of a double-stranded nucleic acid that specifically binds with a prostate cancer maker 1 wherein the nucleic acid is selected from the group consisting of a nucleic acid having the sequence SEQ ID NO:5, a nucleic acid having the sequence SEQ ID NO:6, a nucleic acid having the sequence SEQ ID NO:7, and a nucleic acid having the sequence SEQ ID NO:8.

The invention includes a kit for alleviating a disease mediated by mal-expression of prostate cancer antigen diagnostic marker 1 in a mammal. The kit comprises a prostate cancer antigen diagnostic marker 1 expression-inhibiting amount of at least one molecule selected from the group consisting of an antibody that specifically binds with prostate cancer antigen diagnostic marker 1, an isolated nucleic acid complementary to a nucleic acid encoding a prostate cancer antigen diagnostic marker 1, the complementary nucleic acid being in an antisense orientation, and an isolated enzymatic nucleic acid which specifically cleaves RNA transcribed from a nucleic acid encoding a prostate cancer antigen diagnostic marker 1, the kit further comprising an applicator, and an instructional material for the use thereof.

In one aspect, the disease is prostate cancer.

In another aspect, the isolated enzymatic nucleic acid which specifically cleaves RNA transcribed from a nucleic acid encoding a prostate cancer antigen diagnostic marker 1 comprises a sequence selected from the group consisting of the sequence of SEQ ID NO:9 and the sequence of SEQ ID NO:10.

In yet a further aspect, the kit further comprises an enzymatic nucleic acid, which specifically cleaves mRNA transcribed from a nucleic acid encoding a polypeptide selected from a group consisting of a vascular epithelial growth factor 1 (VEGF-1) and a metalloproteinase 2 (MMP-2).

The invention includes a kit for treating a disease mediated by mal-expression of prostate cancer antigen diagnostic marker 1 in a mammal, the kit comprising a prostate cancer antigen diagnostic marker 1 expression-inhibiting amount of at least one molecule selected from the group consisting of an antibody that specifically binds with prostate cancer antigen diagnostic marker 1, an isolated nucleic acid complementary to a nucleic acid encoding a prostate cancer antigen diagnostic marker 1, the complementary nucleic acid being in an antisense orientation, and an isolated enzymatic nucleic acid which specifically cleaves mRNA transcribed from a nucleic acid encoding a prostate cancer antigen diagnostic marker 1, the kit further comprising an applicator, and an instructional material for the use thereof.

The invention includes a kit for assessing the level of prostate cancer antigen diagnostic marker 1 in a sample. The kit comprises a molecule that specifically binds with prostate cancer antigen diagnostic marker 1 the kit further comprising an applicator, and an instructional material for the use thereof.

In one aspect, the molecule that specifically binds with a prostate cancer antigen diagnostic marker 1 is selected from the group consisting of an antibody that specifically binds with prostate cancer antigen diagnostic marker 1, and a double-stranded nucleic acid that specifically binds with prostate cancer antigen diagnostic marker 1.

In one aspect, the nucleic acid encoding prostate cancer antigen diagnostic marker 1 shares greater than 99% sequence identity with a nucleic acid having the sequence SEQ ID NO:1.

In another aspect, the prostate cancer antigen diagnostic marker 1 polypeptide shares greater than 99% amino acid sequence identity with the sequence of SEQ ID NO:2.

In a further aspect, the double-stranded nucleic acid that specifically binds with prostate cancer antigen diagnostic marker 1 comprises a sequence selected from the group consisting of a sequence CACGGATG (SEQ ID NO:5), a sequence CACAATGA (SEQ ID NO:6), a sequence CACAATG (SEQ ID NO:7), and a sequence CACAATGTTTTTGT (SEQ ID NO:8).

The invention includes a kit for detecting prostate cancer antigen diagnostic marker 1 in a mammal. The kit comprises a molecule that specifically binds with prostate cancer antigen diagnostic marker 1 polypeptide or with a nucleic acid encoding a prostate cancer antigen diagnostic marker 1, the kit further comprising an applicator, and an instructional material for the use thereof.

In one aspect, the mammal is selected from the group consisting of a dog and a human.

In another aspect, the molecule that specifically binds with a prostate cancer antigen diagnostic marker 1 polypeptide is selected from the group consisting of an antibody that specifically binds with a prostate cancer antigen diagnostic marker 1, and a double-stranded nucleic acid that specifically binds with prostate cancer antigen diagnostic marker 1.

In yet another aspect, the double-stranded nucleic acid that specifically binds with prostate cancer antigen diagnostic marker 1 comprises a sequence selected from the group consisting of a sequence CACGGATG (SEQ ID NO:5), a sequence CACAATGA (SEQ ID NO:6), a sequence CACAATG (SEQ ID NO:7), and a sequence CACAATGTTTTTGT (SEQ ID NO:8).

In a further aspect, the molecule that specifically binds with a nucleic acid encoding a prostate cancer antigen diagnostic marker 1 is selected from the group consisting of a nucleic acid complementary with a nucleic acid sharing greater than 99% sequence identity with sequence SEQ ID NO:1.

The invention includes a Monte Carlo-like screening assay for identification of a double-stranded oligonucleotide that specifically binds with a DNA-binding protein. The assay comprises:

(a) producing a semi-random double stranded oligonucleotide set wherein each double-stranded oligonucleotide comprises a random core nucleotide sequence flanked by a known sequence comprising at least two base pairs; and (b) detecting any oligonucleotide member of the set that specifically binds with a DNA-binding protein, thereby identifying a double-stranded oligonucleotide that specifically binds with a DNA-binding protein.

In one aspect, the invention includes an isolated double-stranded oligonucleotide that specifically binds with a DNA-binding protein identified by the assay.

In one aspect, the detecting of (b) comprises a method selected from the group consisting of an electrophoretic mobility shift assay and a method of detecting a double-stranded oligonucleotide bound with a polypeptide.

In another aspect, the random core nucleotide sequence comprises from about 3 to 12 base pairs.

In yet another aspect, the double-stranded oligonucleotide ranges in length from about 7 to 16 base pairs.

In a further aspect, the random core nucleotide sequence comprises a length selected from the group consisting of 7 base pairs, 8 base pairs, and 9 base pairs.

In yet a further aspect, the assay further comprises:

(c) identifying the sequence of the double-stranded oligonucleotide that binds with the greatest affinity with a DNA-binding protein; and (d) producing a semi-random double stranded oligonucleotide set wherein each double-stranded oligonucleotide consists of the known flanking sequence identified in (c), the oligonucleotide further comprising an additional known such that the unknown random core sequence consists of one less unknown base pair than the sequence identified in (c), and repeating the assay steps of detecting and identifying the sequence of double-stranded oligonucleotide.

In another aspect, the assay further comprises repeating (a) through (d) until the entire sequence of the double-stranded oligonucleotide that binds with the greatest affinity with a DNA-binding protein is identified.

134. A method of identifying a double stranded-oligonucleotide that specifically binds with a DNA-binding protein associated with a tumor, the method comprising (a) producing a semi-random double-stranded oligonucleotide set wherein each double-stranded oligonucleotide comprises a random core nucleotide sequence flanked by a known sequence comprising at least two base pairs;

(b) mixing a double-stranded oligonucleotide member of the set with a sample containing a mixture comprising DNA-binding proteins prepared from a tumor cell or tissue under conditions in which one or more of the double-stranded oligonucleotides in the set specifically binds a DNA-binding protein;

(c) mixing an identical double-stranded oligonucleotide member of the set with an otherwise identical sample containing a mixture comprising DNA-binding proteins prepared from an otherwise identical cell or tissue not comprising a tumor under conditions in which one or more of the double-stranded oligonucleotides in the set specifically binds with a DNA-binding protein;

(d) detecting any specific oligonucleotide-protein binding in (a) and (b); and (e) identifying any double-stranded oligonucleotide that specifically binds with a DNA-binding protein in (b) but which does not specifically bind with a DNA-binding protein in (c), thereby identifying a double-stranded oligonucleotide that specifically binds with a DNA-binding protein associated with a tumor.

In one aspect, the invention includes an isolated double-stranded oligonucleotide identified by this method.

In another aspect, the detecting of (d) comprises a method selected from the group consisting of an electrophoretic mobility shift assay and a method of detecting a labeled double-stranded oligonucleotide bound with a polypeptide.

In yet another aspect, the random core nucleotide sequence comprises from about 3 to 12 base pairs.

In a further aspect, the double-stranded oligonucleotide ranges in length from about 7 to 16 base pairs.

In yet a further aspect, the random core nucleotide sequence comprises a length selected from the group consisting of 7 base pairs, 8 base pairs, and 9 base pairs.

In another aspect, the method further comprises:

(f) identifying the sequence of the double-stranded oligonucleotide that binds with the greatest affinity with a DNA-binding protein in (e);

(g) producing a semi-random double stranded oligonucleotide set wherein each double-stranded oligonucleotide consists of the known flanking sequence identified in (f), the oligonucleotide further comprising an additional known base pair adjacent to the unknown random core sequence such that the unknown random core sequence consists of one less unknown base pair than the sequence identified in (f); and (h) repeating (b) and (e).

In one aspect, the method further comprises repeating (b) through (h) until the entire sequence of the double-stranded oligonucleotide that binds with the greatest affinity with a DNA-binding protein is identified.

The invention includes a Monte Carlo-like screening assay for identification of a double-stranded DNA-binding protein. The assay comprises:

(a) producing a semi-random double stranded oligonucleotide set wherein each double-stranded oligonucleotide comprises a random core nucleotide sequence flanked by a known sequence comprising at least two base pairs; and (b) detecting any DNA-binding protein that specifically binds with an oligonucleotide member of the set, thereby identifying a double-stranded DNA-binding protein.

In one aspect, the detecting of (b) comprises a method selected from the group consisting of an electrophoretic mobility shift assay and a method of detecting a double-stranded oligonucleotide bound with a polypeptide.

In another aspect, the random core nucleotide sequence comprises from about 3 to 12 base pairs.

In yet another aspect, the double-stranded oligonucleotide ranges in length from about 7 to 16 base pairs.

In a further aspect, the random core nucleotide sequence comprises a length selected from the group consisting of 7 base pairs, 8 base pairs, and 9 base pairs.

In another aspect, the assay further comprises:

(c) identifying the sequence of the double-stranded oligonucleotide that binds with the greatest affinity with a DNA-binding protein;

(d) producing a semi-random double stranded oligonucleotide set wherein each double-stranded oligonucleotide consists of the known flanking sequence identified in (c), the oligonucleotide further comprising an additional known such that the unknown random core sequence consists of one less unknown base pair than the sequence identified in (c), and repeating the assay steps of detecting and identifying the sequence of double-stranded oligonucleotide.

In a further aspect, the assay further comprises repeating the steps of the assay until the entire sequence of the double-stranded oligonucleotide that binds with the greatest affinity with a DNA-binding protein is identified.

In another aspect, the invention includes an isolated double-stranded DNA-binding protein identified by the assay.

The invention includes a method of designing a DNA enzyme that specifically cleaves a mRNA encoding PCADM-1. The method comprises (a) synthesizing a test nucleic acid comprising a catalytic core domain wherein the core domain is flanked by a nucleic acid comprising a complementary arm, and wherein the sequence of the complementary arm is selected from a sequence complementary with a sequence comprising the sequence of SEQ ID NO:1, and further wherein the complementary arm sequence is from about 8 to 10 nucleotides in length; and (b) assessing whether the test nucleic acid specifically cleaves a mRNA encoding PCADM-1, thereby designing a DNA enzyme that specifically cleaves a mRNA encoding PCADM-1.

In one aspect, the invention includes a DNA enzyme designed by the method.

The invention includes a method of identifying a DNA enzyme that specifically cleaves a mRNA encoding PCADM-1. The method comprises: (a) synthesizing a test nucleic acid comprising a catalytic core domain flanked by a nucleic acid comprising a binding arm, wherein the sequence of the binding arm is complementary to a sequence comprising from about nucleotide −9 to about nucleotide +450 of SEQ ID NO:1 relative to the translational start site, and further wherein the binding arm sequence is from about 8 to 10 nucleotides in length; and (b) assessing whether the test nucleic acid specifically cleaves a ribonucleic acid encoding PCADM-1, thereby identifying a DNA enzyme that specifically cleaves a ribonucleic acid encoding PCADM-1.

In one aspect, the sequence of the binding arm is complementary to a sequence comprising from about nucleotide +155 to about nucleotide +171 of SEQ ID NO:1 relative to the translational start site. In a further aspect, the invention includes a DNA enzyme identified by the method.

In another aspect, the sequence of the binding arm is complementary to a sequence comprising from about nucleotide −7 to about nucleotide +9 of SEQ ID NO:1 relative to the translational start site.

The invention includes a method of inhibiting expression of prostate cancer antigen diagnostic marker 1 in a cell. The method comprises administering to a cell an isolated enzymatic nucleic acid which specifically cleaves mRNA transcribed from a nucleic acid encoding said prostate cancer antigen diagnostic marker 1, thereby inhibiting expression of said prostate cancer antigen diagnostic marker 1 in said cell.

In one aspect, the isolated enzymatic nucleic acid is selected from the group consisting of an enzymatic nucleic acid having the sequence of SEQ ID NO:9 and an enzymatic nucleic acid having the sequence of SEQ ID NO:10.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiment(s), which, are presently preferred. It should be understood, however, that the invention is not limited to the precise arrangements and instrumentalities shown. In the drawings:

FIG. 1A depicts the nucleic acid sequence (SEQ ID NO:1) of prostate cancer antigen diagnostic marker 1 (PCADM-1). The base substitutions at nucleotide position 190, 191, 465, 475, 488, and 505, relative to the ATG translational start site represent substitutions relative to the nucleic acid sequence of a nucleic acid encoding human S2 ribosomal gene, and are indicated in bold and underline.

FIG. 1B depicts the amino acid sequence (SEQ ID NO:2) of PCADM-1. The five amino acid residues at position 64 (T), 155 (N), 159 (A), 163 (R) and 169 (R), representing amino acid substitutions in the PCADM-1 sequence relative to the amino acid sequence of human S2 ribosomal protein, are indicated in bold and underline.

DETAILED DESCRIPTION OF THE INVENTION

Figure 2:
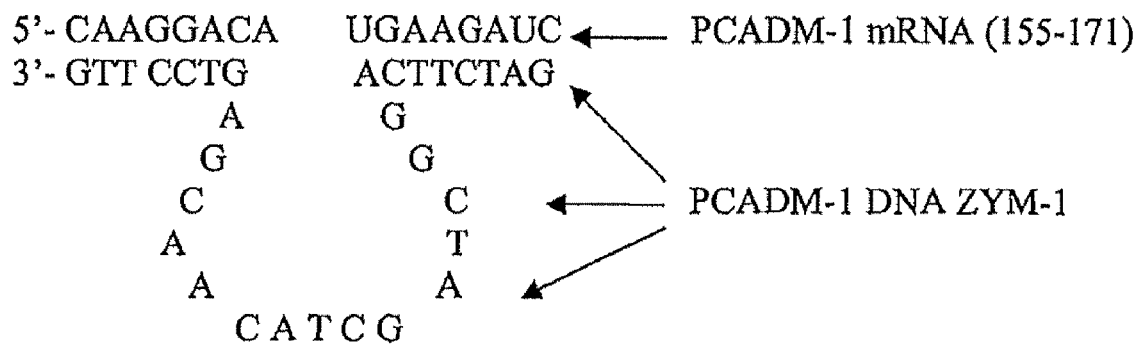
FIG. 2 is a diagram depicting PCADM-1 DNAZYM-1 (SEQ ID NO:9) demonstrating the complementary (i.e., binding) arms matching PCADM-1 mRNA and the 15 bp catalytic domain of the enzyme molecule.

The present invention relates to a novel "Monte Carlo-like" assay for identification of DNA binding proteins and their cognate DNA molecule binding partner. Further, the invention relates to the identification of a novel DNA binding protein, and the cognate DNA sequence that specifically binds therewith. That is, the invention provides the nucleic and amino acid sequences of the novel DNA binding protein, designated PCADM-1 (prostate cancer antigen diagnostic marker 1, previously designated PSTF-1). The invention further relates to a nucleic acid enzyme complementary to PCADM-1 (termed PCADM-1 DNAZYM), which cleaves PCADM-1, and methods of treating cancer using the same.

The present invention relates to PCADM-1-based assays that easily and efficiently assess the presence or absence of prostate cancer in a patient by assessing the level of PCADM-1 in a biological sample compared to the level of PCADM-1 in an otherwise identical biological sample obtained from a human known not to have prostate cancer. The disclosure of International Application No. PCT/US00/25981 is hereby incorporated herein by reference in its entirety.

It has also been discovered, as disclosed herein, that expression of PCADM-1 is increased in prostate cancer tissue and in urine of prostate cancer patients. Further, expression of PCADM-1 is particularly increased in nuclear protein extracts from prostate cancer tumors compared with the level of PCADM-1 in matching seminal vesicle (SV), benign prostatic hyperplasia (BPH) or high-grade prostatic intraepithelial neoplasm (HGPIN) foci. Moreover, the data disclosed herein demonstrate a correlation between the level of PCADM-1 protein in a biological sample and the Gleason Score (GS) of the prostate cancer examined thereby indicating that PCADM-1 can be a stage specific prostate cancer marker useful for proper staging of prostate cancer.

Further, the present invention relates to modulation of PCADM-1 expression and methods of treating cancer, including prostate cancer, mediated thereby. The data disclosed herein suggests that expression of PCADM-1 is associated with prostate cancer and the invention provides methods of diagnosis as well as for the development of therapeutics useful for treating and diagnosing diseases, disorders or conditions associated with altered expression of PCADM-1, including prostate cancer.

Definitions

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

As used herein, the term "adjacent" is used to refer to nucleotide sequences, which are directly attached to one another, having no intervening nucleotides. By way of example, the pentanucleotide 5'-AAAAA-3' is adjacent the trinucleotide 5'-TTT-3' when the two are connected thus: 5'-AAAAATTT-3' or 5'-TTTAAAAA-3', but not when the two are connected thus: 5'-AAAAACTTT-3'.

As used herein, amino acids are represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

As used herein, to "alleviate" cancer means reducing the severity of one or more symptoms of prostate cancer. This can include, but is not limited to, reducing the level of PCADM-1 expressed in a cell or tissue, reducing the level of cell proliferation, reducing or increasing the level of PCADM-1 in the bloodstream or in the urine or other bodily fluid, and the like, in a patient, compared with the level of PCADM-1 in the patient prior to or in the absence of the method of treatment.

By the term "altered expression of PCADM-1," as used herein, is meant that the level of expression of a PCADM-1 in a cell, tissue, organ or bodily fluid is detectably higher or lower than the level of expression of PCADM-1 in an otherwise identical cell, tissue, organ or bodily fluid where the otherwise identical cell, tissue, organ or bodily fluid is obtained from normal patients that do not exhibit any detectable disease, disorder or condition associated with or mediated by expression of PCADM-1, such as, but not limited to, prostate cancer, other cancers and degenerative disorders such as osteoporosis, immune suppressive disorders or inflammatory disorders.

"Antisense" refers particularly to the nucleic acid sequence of the non-coding strand of a double stranded DNA molecule encoding a protein, or to a sequence, which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

By the term "applicator" as the term is used herein, is meant any device including, but not limited to, a hypodermic syringe, a pipette, and the like, for administering the PCADM-1 nucleic acid, protein, and/or composition of the invention to a mammal.

"Biological sample," as that term is used herein, means a sample obtained from an animal that can be used to assess the level of expression of a PCADM-1, the level of PCADM-1 protein present, or both. Such a sample includes, but is not limited to, a blood sample, a prostate biopsy, a urine sample, prostatic fluid, semen, lymph fluid, perineal cavity fluid sample, a peritoneal cavity fluid sample, pleural cavity fluid sample, a bone marrow sample, a salivary gland fluid, and a seminal vesicle tissue sample.

"Break point cluster region," as used herein, refers to nucleic acid sequences associated with a chromosomal translocation site, such as, but not limited to, those identified in studies relating to leukemia.

By "candidate anti-PCADM-1 drug," as the term is used herein, is meant a compound that when contacted with a cell, reduces the level of expression of a nucleic acid encoding a PCADM-1 in the cell compared with the level of PCADM-1 expression in that cell prior to contacting the cell with the compound, or which compound reduces the level of expression in the cell compared with the level of PCADM-1 expression in an otherwise identical cell which is not contacted with the compound.

By "complementary to a portion or all of the nucleic acid encoding PCADM-1" is meant a sequence of a nucleic acid, which does not encode a PCADM-1 protein. Rather, the sequence, which is being expressed in the cells, is identical to the non-coding strand of the nucleic acid encoding a PCADM-1 protein and thus, does not encode PCADM-1 protein.

The terms "complementary" and "antisense" as used herein, are not entirely synonymous. "Antisense" refers particularly to the nucleic acid sequence of the non-coding strand of a double stranded DNA molecule encoding a protein, or to a sequence, which is substantially homologous to the non-coding strand. "Complementary" as used herein refers to the broad concept of subunit sequence complementary between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs).

A "coding region" of a gene consists of the nucleotide residues of the coding strand of the gene (i.e., exon) and the nucleotides of the non-coding strand of the gene, which are homologous with or complementary to, respectively, the coding region of an mRNA molecule, which is produced by transcription of the gene.

A "coding region" of an mRNA molecule also consists of the nucleotide residues of the mRNA molecule which are matched with an anticodon region of a transfer RNA molecule during translation of the mRNA molecule or which encode a stop codon. The coding region may thus include nucleotide residues corresponding to amino acid residues which are not present in the mature protein encoded by the mRNA molecule (e.g., amino acid residues in a protein export signal sequence).

By the term "consensus", as used herein, is meant a nucleic acid sequence which has been re-sequenced to resolve un-called bases, or which has been extended using RT-PCR extension kit (such as, e.g., that available from Perkin Elmer, Norwalk, Conn.) in the 5' and/or 3' direction and re-sequenced, or which has been assembled from the overlapping sequences of more that one derived clone (or which have been both extended and assembled).

A "non-coding" region of a gene consists of the nucleotide residues of the gene (i.e., introns) including "leader sequences" which are important for mRNA binding to ribosomal proteins involved in mRNA translation to proteins.

"PCADM-1 DNAZYM-1," as the term is used herein, means a DNAZYM comprising SEQ ID NO:9, which specifically targets PCADM-1 mRNA.

By "PCADM-1 DNAZYM-2," as used herein, is meant a DNAZYM comprising SEQ ID NO:10, which enzyme specifically targets PCADM-1 mRNA.

"DNA-protein hybridization assay," as used herein, refers to a binding assay for identification of protein(s), which bind with specific DNA sequences, and for assessing the amounts of protein binding to the DNA.

By "substrate complementary arm" is meant that portion of a DNAZYM, which is complementary to (i.e., able to base-pair with) a portion of its substrate. Generally, such complementary sequence is 100% for a 8 base pair sequence, but can be less or more if desired. For example, as few as 4 bases out of 8 to 10 may be base-paired.

"Electrophoretic mobility shift assay" or "EMSA", as these terms are used herein, refers to a gel based assay for identification of protein(s), which bind specific DNA sequences, and for assessing the amounts of protein binding to the DNA.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting there from. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

By "enhanced enzymatic activity" is meant to include activity measured in cells and/or in vivo where the activity is a reflection of both catalytic activity and PCADM-1 DNAZYMs stability.

As used herein, "enzyme linked immuno-sandwich assay" is an antibody based assay for identification of protein and for measurements of protein levels in cell or tissue preparations.

By "catalytic or enzymatic domain" is meant that part of the DNA enzyme essential for cleavage of an RNA substrate.

By "equivalent" RNA to PCADM-1 is meant to include those naturally occurring RNA molecules associated with cancer in various animals, including human. By "complementary" is meant a nucleic acid that can form hydrogen bond(s) with another RNA sequence by either traditional Watson-Crick or other non-traditional types of base-paired interactions.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., retroviruses, adenoviruses, and adeno-associated viruses) that incorporate the recombinant polynucleotide.

A first region of an oligonucleotide "flanks" a second region of the oligonucleotide if the two regions are adjacent one another or if the two regions are separated by no more than about 100 nucleotides, and preferably no more than about 50 nucleotides, more preferably, no more than about 40 nucleotides, even more preferably, no more than about 30 nucleotides, yet more preferably, no more than about 20 nucleotides, preferably, no more than about 10 nucleotides, and even more preferably, by no more than about 5 nucleotides.

As used herein, the term "fragment" as applied to a nucleic acid, may ordinarily be at least about 20 nucleotides in length, typically, at least about 30 nucleotides, more typically, from about 50 to about 100 nucleotides, preferably, at least about 100 to about 200 nucleotides, even more preferably, at least about 200 nucleotides to about 300 nucleotides, yet even more preferably, at least about 300 to about 350, even more preferably, at least about 350 nucleotides to about 500 nucleotides, yet even more preferably, at least about 500 to about 600, even more preferably, at least about 600 nucleotides to about 620 nucleotides, yet even more preferably, at least about 620 to about 650, and most preferably, the nucleic acid fragment will be greater than about 650 nucleotides in length.

As applied to a protein, a "fragment" of PCADM-1 is about 20 amino acids in length. More preferably, the fragment of a PCADM-1 is about 30 amino acids, even more preferably, at least about 40, yet more preferably, at least about 60, even more preferably, at least about 80, yet more preferably, at least about 100, even more preferably, about 100, and more preferably, greater than 110 amino acids in length.

A "genomic DNA" is a DNA strand which has a nucleotide sequence homologous with a gene. By way of example, both a fragment of a chromosome and a cDNA derived by reverse transcription of a mammalian mRNA are genomic DNAs.

A double-stranded oligonucleotide binds with "greatest affinity," as the term is used herein, when the double-stranded oligonucleotide produces the highest detectable signal indicating protein/DNA binding compared with any signal produced by any other member of the semi-random double-stranded oligonucleotide set of which the double-stranded oligonucleotide is a member.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'-ATTGCC-5' and 3'-TATGGC-5' share 75% homology.

As used herein, "homology" is used synonymously with "identity."

In addition, when the terms "homology" or "identity" are used herein to refer to the nucleic acids and proteins, it should be construed to be applied to homology or identity at both the nucleic acid and the amino acid sequence levels.

A first oligonucleotide anneals with a second oligonucleotide with "high stringency" or "under high stringency conditions" if the two oligonucleotides anneal under conditions whereby only oligonucleotides which are at least about 60%, more preferably at least about 65%, even more preferably at least about 70%, yet more preferably at least about 80%, and preferably at least about 90% or, more preferably, at least about 95% complementary anneal with one another. The stringency of conditions used to anneal two oligonucleotides is a function of, among other factors, temperature, ionic strength of the annealing medium, the incubation period, the length of the oligonucleotides, the G-C content of the oligonucleotides, and the expected degree of non-homology between the two oligonucleotides, if known. Methods of adjusting the stringency of annealing conditions are known (see, e.g., Sambrook et al., 1989, In: Molecular Cloning: A Laboratory Manual, Cold Spring Harbor Laboratory, New York).

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87: 2264-2268), modified as in Karlin and Altschul (1993, Proc. Natl. Acad. Sci. USA 90: 5873-5877). This algorithm is incorporated into the NBLAST and XBLAST programs of Altschul, et al. (1990, J. Mol. Biol. 215: 403-410), and can be accessed, for example, at the National Center for Biotechnology Information (NCBI) world wide web site having the universal resource locator "http://www.ncbi.nlm.nih.gov/BLAST/". BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein.

To obtain gapped alignments for comparison purposes, Gapped BLAST can be utilized as described in Altschul et al. (1997, Nucleic Acids Res. 25: 3389-3402). Alternatively, PSI-Blast or PHI-Blast can be used to perform an iterated search, which detects distant relationships between molecules (id.) and relationships between molecules, which share a common pattern. When utilizing BLAST, Gapped BLAST, PSI-Blast, and PHI-Blast programs, the default parameters of the respective programs (e.g., XBLAST and NBLAST) can be used. See http://www.ncbi.nlm.nih.gov.

The percent identity between two sequences can be determined using techniques similar to those described above, with or without allowing gaps. In calculating percent identity, typically exact matches are counted.

By "inhibit PCADM-1" is meant that the activity of PCADM-1 or level of mRNAs encoded by PCADM-1 is reduced below that detected in the absence of the nucleic acid. More preferably, inhibition with DNAZYMs or DNA enzymes is below that level observed in the presence of an inactive RNA molecule able to bind to the same site on the mRNA, but unable to cleave the RNA.

As used herein, the term "Gleason Score" refers to the pathological scoring system developed by Gleason et al. (1993, J. Urol. 149: 1568-1576).

As used herein, the terms "gene" and "recombinant gene" refer to nucleic acid molecules comprising an open reading frame encoding a polypeptide of the invention. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

Moreover, nucleic acid molecules encoding proteins of the invention from other species (homologs), which have a nucleotide sequence which, differs from that of the human proteins described herein, are within the scope of the invention. Nucleic acid molecules corresponding to natural allelic variants and homologs of a cDNA of the invention can be isolated based on their identity to human nucleic acid molecules using the human cDNAs, or a portion thereof, as a hybridization probe according to standard hybridization techniques under stringent hybridization conditions. For example, a homolog of a human PCADM-1 protein of the invention can be isolated based on its hybridization with a nucleic acid molecule encoding all or part of human PCADM-1 under high stringency conditions.

As used herein, an "instructional material" includes a publication, a recording, a diagram, or any other medium of expression, which can be used to communicate the usefulness of the nucleic acid, peptide, and/or composition of the invention in the kit for effecting alleviation of the various diseases or disorders recited herein. Optionally, or alternately, the instructional material may describe one or more methods of alleviation the diseases or disorders in a cell or a tissue of a mammal. The instructional material of the kit of the invention may, for example, be affixed to a container, which contains the nucleic acid, peptide, DNAZYM and/or composition of the invention or be shipped together with a container, which contains the nucleic acid, peptide, and/or composition. Alternatively, the instructional material may be shipped separately from the container with the intention that the instructional material and the compound be used cooperatively by the recipient.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids, which have been substantially purified from other components, which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA, which is part of a hybrid gene encoding additional polypeptide sequence.

In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

By the term "mal-expression of a PCADM-1 molecule," as used herein, is meant that the level of expression of a PCADM-1 in a cell is detectably higher or lower than the level of expression of PCADM-1 in an otherwise identical cell where the otherwise identical cell is obtained from normal tissue that does not exhibit any detectable disease, disorder or condition associated with or mediated by expression of PCADM-1, such as, but not limited to, prostate cancer, other cancers and degenerative disorders such as osteoporosis, immune suppressive disorders or inflammatory disorders, and the like, such that mal-expression is associated with or mediates a disease, disorder or condition.

"Monte-Carlo-like" screening assay, as used herein, refers to the production of random 7 base pair (bp), 8 bp, and 9 bp DNA sequences and protein binding assays employed to identify the 7 bp, 8 bp, and/or 9 bp sequence which binds a DNA-binding protein(s) produced by tumor tissue where the DNA-binding protein is either not produced, or produced at a lower level, or otherwise not detected, in otherwise identical non-tumor tissue.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized, upon the other. By way of example, a promoter operably linked to the coding region of a gene is able to promote transcription of the coding region.

Preferably, when the nucleic acid encoding the desired protein further comprises a promoter/regulatory sequence, the promoter/regulatory sequence is positioned at the 5' end of the desired protein coding sequence such that it drives expression of the desired protein in a cell. Together, the nucleic acid encoding the desired protein and its promoter/regulatory sequence comprise a "transgene."

By "patient" is meant an organism, which, is a donor or recipient of explanted cells or the cells themselves. "Patient" also refers to an organism to which enzymatic nucleic acid molecules can be administered. Preferably, a patient is a mammal or mammalian cells. More preferably, a patient is a human or human cells or human tumors.

"PCADM-1", as used herein, refers to the amino acid sequences of purified recombinant or native "PCADM-1" protein obtained from any species or tissue or cells or from recombinant, synthetic or semi-synthetic sources. Preferably, the PCADM-1 is encoded by a nucleic acid that hybridizes with a nucleic acid having the sequence SEQ ID NO:1 under stringent conditions. Further, the PCADM-1 shares at least 99% sequence identity with the amino acid sequence SEQ ID NO:2. Further, the PCADM-1 is over-expressed, i.e., expressed at a level higher than the level present in a cell or tissue known not to have a disease, disorder, or condition.

Also, the PCADM-1 is a cytoplasmic and nuclear protein of about 32 kDa with six (6) nucleotide substitutions relative to the human S2 gene. More specifically, a nucleic acid encoding PCADM-1 comprises a change from a T to A at nucleotide number 190, a A to C at nucleotide number 191, a G to C at nucleotide number 465, a change from C to G at nucleotide number 475, a change from C to G at nucleotide number 488, and a T to a C at nucleotide number 505 where the nucleotide numbers relate to SEQ ID NO:1. Thus, it would be understood, that PCADM-1 comprises a A at nt 190, a C at nt 191, a C at nt 465, a G at nt 475, a G at nt 488, a C at nt 505 relative to the AGT translation start site. More preferably, the mRNA encoding PCADM-1 is cleaved by a PCADM-1 DNAZYM disclosed herein, e.g., a DNA enzyme having the sequence GATCTTCAGGCTAGCTACAAC-GAGTCCTTGA (SEQ ID NO:9), GTTCCCCAGGCTAGC-TACAACGACCCAGGGC (SEQ ID NO:10), and the like.

Unless otherwise indicated, "PCADM-1" and "prostate cancer antigen diagnostic marker 1" are used alternatively and refer to the polypeptide encoded by the nucleic acid encoding PCADM-1. Preferably, the nucleic acid encoding PCADM-1 shares greater than 99% identity with the sequence SEQ ID NO:1, the PCADM-1 shares greater than 98% with a protein having the amino acid sequence SEQ ID NO:2, or both. Further, the polypeptide preferably binds at least one double-stranded nucleic acid oligomer that specifically binds with PCADM-1, e.g., the oligonucleotides having the sequence SEQ ID NOs:3-6. Additionally, the amino acid sequence of PCADM-1 shares at least about 98% sequence identity with the amino acid sequence of SEQ ID NO:2.

Further, relative to the amino acid sequence of human S2, PCADM-1 comprises five (5) amino acid substitution at amino acid residue numbers 64, 155, 159, 163 and 169 relative to the amino acid sequence of SEQ ID NO:2. Even more specifically, it would be understood that PCADM-1 comprises a T (threonine) at amino acid residue number 64, an N (asparagine) at amino acid residue number 155, an A (alanine) at residue number 159, an R (arginine) at residue number 163, and an R (arginine) at residue number 169, relative to the amino acid sequence of SEQ ID NO:2.

As used herein, the term "promoter/regulatory sequence" means a nucleic acid sequence, which is required for expression of a gene product operably linked to the promoter/regulatory sequence. In some instances, this sequence may be the core promoter sequence and in other instances, this sequence may also include an enhancer sequence and other regulatory elements, which are required for expression of the gene product. The promoter/regulatory sequence may, for example, be one, which expresses the gene product in a tissue specific manner.

A "constitutive" promoter is a nucleotide sequence which, when operably linked with a polynucleotide which encodes or specifies a gene product, causes the gene product to be produced in a living human cell under most or all physiological conditions of the cell.

An "inducible" promoter is a nucleotide sequence which, when operably linked with a polynucleotide which encodes or specifies a gene product, causes the gene product to be produced in a living human cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living human cell substantially only if the cell is a cell of the tissue type corresponding to the promoter.

A "polyadenylation sequence" is a polynucleotide sequence, which directs the addition of a poly A tail onto a transcribed messenger RNA sequence.

A "polynucleotide" means a single strand or parallel and anti-parallel strands of a nucleic acid. Thus, a polynucleotide may be either a single-stranded or a double-stranded nucleic acid.

The term "nucleic acid" typically refers to large polynucleotides.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T".

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which, are located 5' to a reference point on the DNA are referred to as "upstream sequences"; sequences on the DNA strand which are 3' to a reference point on the DNA are referred to as "downstream sequences."

A "portion" of a polynucleotide means at least at least about twenty sequential nucleotide residues of the polynucleotide. It is understood that a portion of a polynucleotide may include every nucleotide residue of the polynucleotide.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Probe" refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A "recombinant polypeptide" is one, which is produced upon expression of a recombinant polynucleotide.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

As used herein, the term "reporter gene" means a gene, the expression of which can be detected using a known method. By way of example, the *Escherichia coli* lacZ gene may be used as a reporter gene in a medium because expression of the lacZ gene can be detected using known methods by adding the chromogenic substrate o-nitrophenyl-β-galactoside to the medium (Gerhardt et al., eds., 1994, Methods for General and Molecular Bacteriology, American Society for Microbiology, Washington, D.C., p. 574).

"PCADM-1-inhibiting amount," as used herein, means any amount of a substance or molecule that detectably decreases the level of PCADM-1 expression, amount, and/or activity compared with the level of PCADM-1 expression, amount, and/or activity in the absence of the substance or molecule. Thus, any amount that mediates a detectable decrease in: the amount of PCADM-1 present and/or the level of PCADM-1 mRNA or protein expression, is encompassed in the present invention. The assays by which these conditions are examined are well-known in the art and several are exemplified herein.

The term "PCADM-1 activity", as used herein, refers to the ability of a molecule or compound to ensure cell survival and growth, to be detected in prostate cancer tissue but not in non-cancer tissue, and the like. Further, PCADM-1 activity encompasses the ability of a polypeptide to specifically bind with a nucleic acid having the sequence of a least one of SEQ ID NOs:5-8 as more fully set forth elsewhere herein.

By "PCADM-1 DNAZYM" it is meant a nucleic acid molecule, which has complementary sequence in a substrate binding region to a specified gene target, and also has an enzymatic or catalytic activity, which is active to specifically cleave RNA in that target. That is, the enzymatic nucleic acid molecule is able to inter-molecularly cleave RNA and thereby inactivate a target RNA molecule. This complementary matching of sequence functions to allow sufficient hybridization of the enzymatic nucleic acid molecule to the target RNA to allow the cleavage to occur. The term "DNAZYMs", "DNA enzymes" or "enzymatic nucleic acid" or "PCADM-1 DNAZYM" specifically refers to a DNA sequence complementary, or partially complimentary, to the PCADM-1 mRNA sequence and the terms are used interchangeably herein. However, because they share a common functional capability, the term "DNAZYM" is used interchangeably with phrases such as ribozymes, catalytic RNA, enzymatic RNA, catalytic DNA, nucleozyme, RNA enzyme, endo-ribonuclease, mini-zyme, or leadzyme, oligozyme, as used in the art. All of these terminologies describe nucleic acid molecules with enzymatic activity.

By "associated with" and "mediated", used in the context of diseases, disorders or conditions associated with and/or mediated by PCADM-1 'mal-expression', is meant that the inhibition of PCADM-1 RNAs and thus reduction in the level respective protein activity, will relieve, to some extent, the symptoms of the disease, disorder or condition.

A "restriction site" is a portion of a double-stranded nucleic acid, which is recognized by a restriction endonuclease.

A portion of a double-stranded nucleic acid is "recognized" by a restriction endonuclease if the endonuclease is capable of cleaving both strands of the nucleic acid at the portion when the nucleic acid and the endonuclease are contacted.

By the term "specifically binds," as used herein, is meant a compound, e.g., a protein, a nucleic acid, or an antibody, enzyme, DNAZYM and the like, which recognizes and binds a specific molecule, but does not substantially recognize or bind other molecules in a sample.

A first oligonucleotide anneals with a second oligonucleotide "with high stringency" if the two oligonucleotides anneal under conditions whereby only oligonucleotides which have complementary regions of 2-10 bp flanking the catalytic core can anneal with one another. The stringency of conditions used to anneal two oligonucleotides is a function of, among other factors, temperature, ionic conditions, ionic strength of the annealing medium, the incubation period, the length of the oligonucleotides, the G-C content of the oligonucleotides, and the expected degree of non-homology between the two oligonucleotides, if known. Methods of adjusting the stringency of annealing conditions are known (see, e.g., Sambrook et al., 1989, Molecular Cloning: A Laboratory Manual, Cold Spring Harbor Laboratory, New York).

As used herein, the term "transgene" means an exogenous nucleic acid sequence which exogenous nucleic acid is encoded by a transgenic cell or mammal.

A "recombinant cell" is a cell that comprises a transgene. Such a cell may be a eukaryotic cell or a prokaryotic cell. Also, the transgenic cell encompasses, but is not limited to, an embryonic stem cell comprising the transgene, a cell obtained from a chimeric mammal derived from a transgenic ES cell where the cell comprises the transgene, a cell obtained from a transgenic mammal, or fetal or placental tissue thereof, and a prokaryotic cell comprising the transgene.

By the term "exogenous nucleic acid" is meant that the nucleic acid has been introduced into a cell or an animal using technology, which, has been developed for the purpose of facilitating the introduction of a nucleic acid into a cell or an animal.

By "substrate flanking region" is meant that portion of a DNAZYM, which, is located on either side of the catalytic care and which is complementary to (i.e., able to base-pair with) a portion of its substrate. Generally, such complementary sequence is 100%, For example, as few as 2 bases out of 8 to 10 may be base-paired.

By "tag" polypeptide is meant any protein which, when linked by a peptide bond to a protein of interest, may be used to localize the protein, to purify it from a cell extract, to immobilize it for use in binding assays, or to otherwise study its biological properties and/or function.

As used herein, the term "transgenic mammal" means a mammal, the germ cells of which, comprise an exogenous nucleic acid.

As used herein, to "treat" means reducing the frequency with which symptoms of the prostate cancer, are experienced by a patient.

By the term "vector" as used herein, is meant any plasmid or virus encoding an exogenous nucleic acid. The term should also be construed to include non-plasmid and non-viral compounds which facilitate transfer of nucleic acid into virions or cells, such as, for example, polylysine compounds and the like. The vector may be a viral vector which is suitable as a delivery vehicle for delivery of the PCADM-1 protein or nucleic acid encoding a mammalian PCADM-1, or a DNAZYM complementary to a nucleic acid encoding PCADM-1, or a portion thereof, to the patient, or the vector may be a non-viral vector which is suitable for the same purpose. Examples of viral and non-viral vectors for delivery of DNA to cells and tissues are well known in the art and are described, for example, in Ma et al. (1997, Proc. Natl. Acad. Sci. U.S.A. 94: 12744-12746). Examples of viral vectors include, but are not limited to, a recombinant vaccinia virus, a recombinant adenovirus, a recombinant retrovirus, a recombinant adeno-associated virus, a recombinant avian pox virus, and the like (Cranage et al., 1986, EMBO J. 5: 3057-3063; International Patent Application No. WO94/17810, published Aug. 18, 1994; International Patent Application No. WO94/23744, published Oct. 27, 1994). Examples of non-viral vectors include, but are not limited to, liposomes, polyamine derivatives of DNA, and the like.

A "knock-out targeting vector," as the term is used herein, means a vector comprising two nucleic acid sequences each of which is complementary to a nucleic acid regions flanking a target sequence of interest, which is to be deleted and/or replaced, by another nucleic acid sequence. The two nucleic acid sequences therefore flank the target sequence, which is to be removed by the process of homologous recombination.

Description

I. Isolated Nucleic Acids
  A. Sense Nucleic Acids
  The present invention includes an isolated nucleic acid encoding a mammalian PCADM-1, or a fragment thereof, wherein the nucleic acid shares at least 98% identity with a nucleic acid having the sequence SEQ ID NO:1. Preferably, the nucleic acid is about 99% homologous to SEQ ID NO:1. Even more preferably, the nucleic acid is SEQ ID NO:1.

Preferably, a nucleic acid encoding PCADM-1 comprises a change from a T to A at nucleotide number 190, a change from A to C at nucleotide 191, a change from a G to C at nucleotide number 465, a change from C to G at nucleotide number 475, a change from C to G at nucleotide number 488, and a T to a C at nucleotide number 505 where the nucleotide numbers relate to SEQ ID NO:1. Thus, it would be understood that PCADM-1 comprises a A at nucleotide 190, a C at nucleotide 191, a C at nucleotide 465, a G at nucleotide 475, a G at nucleotide 488, a C at nucleotide 505 relative to the ATG translation start site.

More preferably, the mRNA encoding PCADM-1 is cleaved by a PCADM-1 DNAZYM nuclease disclosed herein, e.g., a PCADM-1 DNAZYM having the sequence GATCTTCAGGCTAGCTACAACGAGTCCTTGA (SEQ ID NO:9), and the sequence GTTCCCCAGGCTAGCTA-CAACGACCCAGGGC (SEQ ID NO:10).

In another aspect, the present invention includes an isolated nucleic acid encoding a mammalian PCADM-1, or a fragment thereof, wherein the protein encoded by the nucleic acid shares at least 98% homology with the amino acid sequence SEQ ID NO:2. Preferably, the protein is about 99% homologous, and most preferably, about 100% homologous to SEQ ID NO:2. Even more preferably, the PCADM-1 protein encoded by the nucleic acid is SEQ ID NO:2.

Further, the polypeptide encoded by a nucleic acid having the sequence of SEQ ID NO:1 preferably binds at least one double-stranded nucleic acid oligomer that specifically binds with PCADM-1, e.g., the oligonucleotides having the sequence SEQ ID NOs:5-8.

Additionally, the amino acid sequence of PCADM-1 preferably shares at least about 98% sequence identity with the amino acid sequence of SEQ ID NO:2 and comprises an amino acid substitution at amino acid residue numbers 64, 155, 159, 163 and 169 of the PCADM-1 protein of SEQ ID NO:2 and compared with the amino acid sequence of human S2. Even more specifically, it would be understood that PCADM-1 comprises a T (threonine) residue at amino acid residue number 64; an N (asparagine) residue at amino acid residue number 155, an A (alanine) at residue number 159, an R (arginine) at residue number 163, and an R (arginine) at residue number 169 relative to the amino acid sequence of SEQ ID NO:2.

One skilled in the art would appreciate, based upon the disclosure provided herein, that mammalian PCADM-1 homologs likely exist and can be readily identified and isolated using the methods described herein using the sequence data disclosed herein. Thus, the present invention encompasses additional PCADM-1s, both human isoforms and PCADM-1 homologs from other species that can be readily identified based upon the disclosure provided herein.

The isolated nucleic acid of the invention should be construed to include an RNA or a DNA sequence encoding a PCADM-1 protein of the invention, and any modified forms thereof, including chemical modifications of the DNA or RNA which render the nucleotide sequence more stable when it is cell free or when it is associated with a cell. Chemical modifications of nucleotides may also be used to enhance the efficiency with which a nucleotide sequence is taken up by a cell or the efficiency with which it is expressed in a cell. Any and all combinations of modifications of the nucleotide sequences are contemplated in the present invention.

The present invention should not be construed as being limited solely to the nucleic and amino acid sequences disclosed herein. Once armed with the present invention, it is readily apparent to one skilled in the art that other nucleic acids encoding PCADM-1 proteins such as those present in other species of mammals (e.g., ape, gibbon, bovine, ovine, equine, porcine, canine, feline, and the like) can be obtained by following the procedures described herein in the experimental details section for the isolation of human PCADM-1 nucleic acids encoding PCADM-1 polypeptides as disclosed herein (e.g., screening of genomic or cDNA libraries), and procedures that are well-known in the art (e.g., reverse transcription PCR using mRNA samples and antibody-based methods) or to be developed.

Further, any number of procedures may be used for the generation of mutant, derivative or variant forms of PCADM-1 using recombinant DNA methodology well known in the art such as, for example, that described in Sambrook et al. (1989, In: Molecular Cloning: A Laboratory Manual, Cold Spring Harbor Laboratory Press, New York) and Ausubel et al. (1997, Current Protocols in Molecular Biology, Green & Wiley, New York).

Procedures for the introduction of amino acid changes in a protein or polypeptide by altering the DNA sequence encoding the polypeptide are well known in the art and are also described in Sambrook et al. (1989, supra); Ausubel et al. (1997, supra).

The invention includes a nucleic acid encoding a mammalian PCADM-1 wherein the nucleic acid encoding a tag polypeptide is covalently linked thereto. That is, the invention encompasses a chimeric nucleic acid wherein the nucleic acid sequences encoding a tag polypeptide is covalently linked to the nucleic acid encoding human PCADM-1. Such tag polypeptides are well known in the art and include, for instance, green fluorescent protein, myc, myc-pyruvate kinase (myc-PK), $His_6$, maltose biding protein (MBP), an influenza virus hemagglutinin tag polypeptide, a flag tag polypeptide, and a glutathione-S-transferase (GST) tag polypeptide. However, the invention should in no way be construed to be limited to the nucleic acids encoding the above-listed tag polypeptides. Rather, any nucleic acid sequence encoding a polypeptide, which may function in a manner substantially similar to these tag polypeptides should be construed to be included in the present invention.

The nucleic acid comprising a nucleic acid encoding a tag polypeptide can be used to localize PCADM-1 within a cell, a tissue, and/or a whole organism (e.g., a mammalian embryo), detect PCADM-1 secreted from a cell, and to study the role(s) of PCADM-1 in a cell. Further, addition of a tag polypeptide facilitates isolation and purification of the "tagged" protein such that the proteins of the invention can be produced and purified readily.

The invention also includes a duplex (i.e., double-stranded) nucleic acid that specifically binds with a mammalian PCADM-1 polypeptide. One skilled in the art would understand, based upon the disclosure provided herein, that such duplex nucleic acids include PCADM-1 probe 1 (5'-CACG-GATG-3' [SEQ ID NO:5] and PCADM-1 probe 2 (5'-CA-CAATGA-3' [SEQ ID NO:6]), 5'-CACAATG-3' (SEQ ID NO:7), and 5'-CACAATGTTTTTGT-3' (SEQ ID NO:8). The skilled artisan would appreciate that nucleic acids that specifically bind with PCADM-1 can be used to detect the presence or absence of PCADM-1 in a protein sample derived from solid tissue or fluids, and to assess the level of PCADM-1 therein, as more fully discussed elsewhere herein. Thus, the duplex (i.e., double-stranded, which is used interchangeably herein), nucleic acids are powerful probes useful for detection of any disease, disorder, or condition associated with mal-expression of PCADM-1, including, but not limited to, prostate cancer.

B. Antisense Nucleic Acids

In certain situations, it may be desirable to inhibit expression of PCADM-1 and the invention therefore includes compositions useful for inhibition of PCADM-1 expression. Thus, the invention features an isolated nucleic acid complementary to a portion or all of a nucleic acid encoding a mammalian PCADM-1 which nucleic acid is in an antisense orientation with respect to transcription. Preferably, the antisense nucleic acid is complementary with a nucleic acid having at least about 95% homology with SEQ ID NO:1. Preferably, the nucleic acid is about 96% homologous, more preferably, about 97% homologous, more preferably, about 98% homologous, and most preferably, about 99% homologous to a nucleic acid complementary to a portion or all of a nucleic acid encoding a mammalian PCADM-1 having the sequence SEQ ID NO:1, or a fragment thereof, which is in an antisense orientation with respect to transcription. Most preferably, the nucleic acid is complementary to a portion or all of a nucleic acid having the sequence SEQ ID NO:1, or a fragment thereof. Such antisense nucleic acid serves to inhibit the expression, function, or both, of a PCADM-1.

Alternatively, antisense molecules of the invention may be made synthetically and then provided to the cell. Antisense oligomers of between about 10 to about 30, and more preferably about 15 nucleotides, are preferred, since they are easily synthesized and introduced into a target cell. Synthetic antisense molecules contemplated by the invention include oligonucleotide derivatives known in the art, which have improved biological activity compared to unmodified oligonucleotides (see Cohen, supra; Tullis, 1991, U.S. Pat. No. 5,023,243, incorporated by reference herein in its entirety).

II. Isolated Polypeptides

The invention also includes an isolated polypeptide comprising a mammalian PCADM-1 molecule. Preferably, the isolated polypeptide is about 98% homologous, and even more preferably, 99% homologous to SEQ ID NO:2. More preferably, the isolated polypeptide comprising a mammalian PCADM-1 is human PCADM-1. Most preferably, the isolated polypeptide comprising a mammalian PCADM-1 is SEQ ID NO:2.

Additionally, relative to the amino acid sequence of human S2, PCADM-1 comprises an amino acid substitution at amino acid residue numbers 64, 155, 159, 163 and 169 relative to the amino acid sequence of SEQ ID NO:2. Even more specifically, it would be understood that PCADM-1 preferably comprises an T (threonine) at amino acid residue number 64, an N (asparagine) at amino acid residue number 155, an A (alanine) at residue number 159, an R (arginine) at residue number 163, and an R (arginine) at residue 169 relative to the amino acid sequence of SEQ ID NO:2.

A biological property of a PCADM-1 protein should be construed but not be limited to include, the ability to specifically bind with a nucleic acid sequence having the sequence of at least one of CACGGATG (PCADM-1 probe 1; SEQ ID NO:5) and CACAATGA (PCADM-1 probe 2; SEQ ID NO:6), CACAATG (SEQ ID NO:7), and CACAATGTTTTTGT (SEQ ID NO:8), and the like.

The present invention also provides for analogs of proteins or peptides, which comprise a PCADM-1 as disclosed herein. Analogs may differ from naturally occurring proteins or peptides by conservative amino acid sequence differences or by modifications, which do not affect sequence, or by both. For example, conservative amino acid changes may be made, which although they alter the primary sequence of the protein or peptide, do not normally alter its function. Conservative amino acid substitutions typically include substitutions within the following groups:

glycine, alanine;
valine, isoleucine, leucine;
aspartic acid, glutamic acid;
asparagine, glutamine;
serine, threonine;
lysine, arginine;
phenylalanine, tyrosine.

Modifications (which do not normally alter primary sequence) include in vivo, or in vitro, chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences, which have phosphorylated amino acid residues, e.g., phosphotyrosine, phosphoserine, or phosphothreonine.

Also included are polypeptides, which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

The present invention should also be construed to encompass "mutants," "derivatives," and "variants" of the peptides of the invention (or of the DNA encoding the same) which mutants, derivatives and variants are PCADM-1 peptides which are altered in one or more amino acids (or, when referring to the nucleotide sequence encoding the same, are altered in one or more base pairs) such that the resulting peptide (or DNA) is not identical to the sequences recited herein, but has the same biological property as the peptides disclosed herein, in that the peptide has biological/biochemical properties of the PCADM-1 peptide of the present invention.

Further, the invention should be construed to include naturally occurring variants or recombinant derived mutants of PCADM-1 sequences, which variants or mutants render the protein encoded thereby either more, less, or just as biologically active as the full-length clones of the invention.

The nucleic acids, and peptides encoded thereby, are useful tools for elucidating the function(s) of PCADM-1 in a cell. Further, nucleic and amino acids comprising mammalian PCADM-1 are useful diagnostics, which can be used, for example, to identify a compound that affects PCADM-1 expression and is a potential prostate anticancer anti-cell proliferation drug candidate. The nucleic acids, the proteins encoded thereby, or both, can be administered to a mammal to increase or decrease expression of PCADM-1 in the mammal. This can be beneficial for the mammal in situations where under or over-expression of PCADM-1 in the mammal mediates a disease or condition associated with altered expression of PCADM-1 compared with normal expression of PCADM-1 in a healthy mammal.

Additionally, the nucleic and amino acids of the invention can be used to produce recombinant cells and transgenic non-human mammals, which are useful tools for the study of PCADM-1 action, the identification of novel diagnostics and therapeutics for treatment of prostate cancer, and possibly other cancers, and for elucidating the cellular role(s) of PCADM-1, among other things.

Further, the nucleic and amino acids of the invention can be used diagnostically, either by assessing the level of gene expression or protein expression, to assess severity, stage and prognosis of prostate tumors and the like. The nucleic acids and proteins of the invention are also useful in the development of assays to assess the efficacy of a treatment for prostate tumors. That is, the nucleic acids and polypeptides of the invention can be used to detect the effect of various therapies on PCADM-1 expression, thereby ascertaining the effectiveness of the therapies.

III. Vectors

In other related aspects, the invention includes an isolated nucleic acid encoding a mammalian PCADM-1 operably linked to a nucleic acid comprising a promoter/regulatory sequence such that the nucleic acid is preferably capable of directing expression of the protein encoded by the nucleic acid. Thus, the invention encompasses expression vectors and methods for the introduction of exogenous DNA into cells with concomitant expression and transcription of the exogenous DNA in the cells such as those described, for example, in Sambrook et al. (1989, supra), and Ausubel et al. (1997, supra).

Expressing PCADM-1 using a vector allows the isolation of large amounts of recombinant produced protein. Further, where the lack or decreased level of PCADM-1 expression causes a disease, disorder, or condition associated with such expression, the expression of PCADM-1 driven by a promoter/regulatory sequence can provide useful therapeutics including, but not limited to, gene therapy whereby PCADM-1 is provided. A disease, disorder or condition associated with a decreased level of expression, level of protein, or decreased activity of the protein, for which administration of PCADM-1 can be useful can includes, but is not limited to, prostate cancer, and other cancers, and the like. Therefore, the invention includes not only methods of inhibiting PCADM-1 expression, translation, and/or activity, but it also includes methods relating to increasing PCADM-1 expression, protein level, and/or activity since both decreasing and increasing PCADM-1 expression and/or activity can be useful in providing effective therapeutics.

Selection of any particular plasmid vector or other DNA vector is not a limiting factor in this invention and a wide plethora vectors is well-known in the art. Further, it is well within the skill of the artisan to choose particular promoter/regulatory sequences and to operably link those promoter/regulatory sequences to a DNA sequence encoding a desired polypeptide. Such technology is well known in the art and is described, for example, in Sambrook et al. (1989, In: Molecular Cloning: A Laboratory Manual, Cold Spring Harbor Laboratory Press, New York) and Ausubel et al. (1997, Current Protocols in Molecular Biology, Green & Wiley, New York).

The invention thus includes a vector comprising an isolated nucleic acid encoding a mammalian PCADM-1. The incorporation of a desired nucleic acid into a vector and the choice of vectors is well-known in the art as described in, for example, Sambrook et al., supra, and Ausubel et al., supra.

The invention also includes cells, viruses, proviruses, and the like, containing such vectors. Methods for producing cells comprising vectors and/or exogenous nucleic acids are well-known in the art. See, e.g., Sambrook et al., supra; Ausubel et al., supra.

The nucleic acids encoding PCADM-1 may be cloned into various plasmid vectors. However, the present invention should not be construed to be limited to plasmids or to any particular vector. Instead, the present invention should be construed to encompass a wide plethora of vectors, which are readily available and/or well-known in the art.

IV. Antisense Molecules, Ribozymes, and DNA Enzymes

Further, the invention includes a recombinant cell comprising an antisense nucleic acid which cell is a useful model for elucidating the role(s) of PCADM-1 in cellular processes. That is, without wishing to be bound by any particular theory, the increased expression of PCADM-1 in prostate cancer tissues but not in benign prostate tumors or in normal prostate tissues indicates that PCADM-1 is involved in cell survival and cell proliferation associated with tumor growth. Accordingly, a transgenic cell comprising an antisense nucleic acid complementary to PCADM-1 is a useful tool for the study of the mechanism(s) of action of PCADM-1 and its role(s) in the cell and for the identification of therapeutics that ameliorate the effect(s) of PCADM-1 over-expression. Further, methods of decreasing PCADM-1 expression and/or activity in a cell can provide useful diagnostics and/or therapeutics for diseases, disorders or conditions mediated by or associated with increased PCADM-1 expression, increased level of PCADM-1 protein in a cell or secretion there from, and/or increased PCADM-1 activity. Such diseases, disorders or conditions include, but are not limited to, prostate cancer, and the like.

One skilled in the art will appreciate that one way to decrease the levels of PCADM-1 mRNA and/or protein in a cell is to inhibit expression of the nucleic acid encoding the protein. Expression of PCADM-1 may be inhibited using, for example, antisense molecules, and also by using ribozymes or double-stranded RNA as described in, for example, Wianny and Kernicka-Goetz (2000, Nature Cell Biol. 2: 70-75).

A. Antisense Molecules

Antisense molecules and their use for inhibiting gene expression are well known in the art (see, e.g., Cohen, 1989, In: Oligodeoxyribonucleotides, Antisense Inhibitors of Gene Expression, CRC Press). Antisense nucleic acids are DNA or RNA molecules that are complementary, as that term is defined elsewhere herein, to at least a portion of a specific mRNA molecule (Weintraub, 1990, Scientific American 262: 40). In the cell, antisense nucleic acids hybridize to the corresponding mRNA, forming a double-stranded molecule thereby inhibiting the translation of genes.

The use of antisense methods to inhibit the translation of genes is known in the art, and is described, for example, in Marcus-Sakura (1988, Anal. Biochem. 172:289). Such antisense molecules may be provided to the cell via genetic expression using DNA encoding the antisense molecule as taught by Inoue (1993, U.S. Pat. No. 5,190,931).

Alternatively, antisense molecules of the invention may be made synthetically and then provided to the cell. Antisense oligomers of between about 10 to about 100, and more preferably about 15 to about 50 nucleotides, are preferred, since they are easily synthesized and introduced into a target cell. Synthetic antisense molecules contemplated by the invention include oligonucleotide derivatives known in the art, which have improved biological activity compared to unmodified oligonucleotides (see Cohen, supra; Tullis, 1991, U.S. Pat. No. 5,023,243, incorporated by reference herein in its entirety).

B. Ribozymes

Ribozymes and their use for inhibiting gene expression are also well known in the art (see, e.g., Cech et al., 1992, J. Biol. Chem. 267: 17479-17482; Hampel et al., 1989, Biochemistry 28: 4929-4933; Eckstein et al., International Publication No. WO 92/07065; Altman et al., U.S. Pat. No. 5,168,053, incorporated by reference herein in its entirety). Ribozymes are RNA molecules possessing the ability to specifically cleave other single-stranded RNA in a manner analogous to DNA restriction endonucleases. Through the modification of nucleotide sequences encoding these RNAs, molecules can be engineered to recognize specific nucleotide sequences in an RNA molecule and cleave it (Cech, 1988, J. Amer. Med. Assn. 260:3030). A major advantage of this approach is that, because they are sequence-specific, only mRNAs with particular sequences are inactivated.

There are two basic types of ribozymes, namely, Tetrahymena-type (Hasselhoff, 1988, Nature 334:585) and hammerhead-type. Tetrahymena-type ribozymes recognize sequences, which are four bases in length, while hammerhead-type ribozymes recognize base sequences 11-18 bases in length. The longer the sequence, the greater the likelihood that the sequence will occur exclusively in the target mRNA species. Consequently, hammerhead-type ribozymes are preferable to Tetrahymena-type ribozymes for inactivating specific mRNA species, and 18-base recognition sequences are preferable to shorter recognition sequences, which may occur randomly within various unrelated mRNA molecules.

Ribozymes useful for inhibiting the expression of PCADM-1 may be designed by incorporating target sequences into the basic ribozyme structure which are complementary to the mRNA sequence of the PCADM-1 encoded by PCADM-1 or having at least about 80% homology to at least one of SEQ ID NO:1. Ribozymes targeting PCADM-1 can be synthesized using commercially available reagents (Applied Biosystems, Inc., Foster City, Calif.) or they may be genetically expressed from DNA encoding them.

C. DNA Enzymes

The invention encompasses DNA enzymes, or enzymatic nucleic acid molecules, directed to cleave RNA species that are required for cellular growth responses. In particular, the invention comprises selection and characterization of DNAZYMs (DNA enzymes) capable of cleaving RNA encoded by the PCADM-1 gene. Such DNA enzymes can be used, among other things, to inhibit the survival of tumor cells in one or more cancers.

Figure 3:
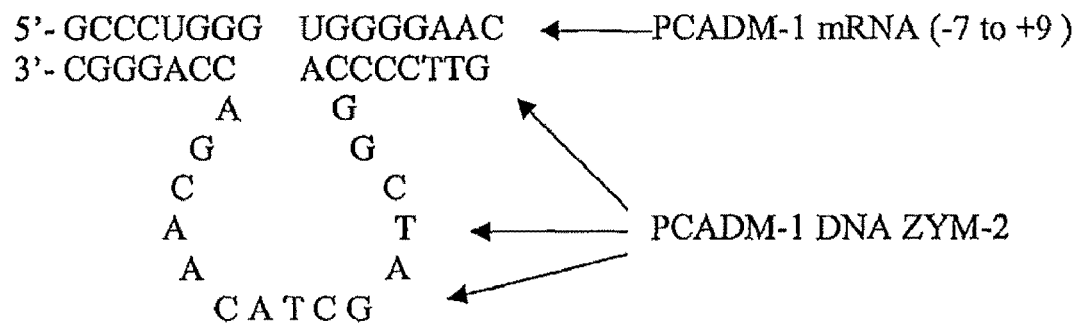
FIG. 3 is a diagram of PCADM-1 DNAZYM-2 (SEQ ID NO:10) depicting the complementary arms matching PCADM-1 mRNA and the 15 bp catalytic domain of the enzyme molecule.

In the present invention, examples of DNAZYMs that cleave PCADM-1 RNA are described FIG. 2 and FIG. 3 (i.e., PCADM-1 DNAZYM-1 (SEQ ID NO:9) and PCADM-1 DNAZYM-2 (SEQ ID NO:10)). Those of ordinary skill in the art, based upon the disclosure provided herein, will understand that from the examples described, other DNAZYMs that cleave target RNAs required for cell proliferation can be readily designed following the teachings described in, e.g., Finkel (1999, Science 286: 2441-2442), and that such DNAZYMs are encompassed by the invention.

DNAZYMs, also referred to herein as DNA enzymes, have recently proven of import since they are short DNA molecules with simple structures, which are more stable to nucleases. One catalytic motif identified for DNA enzymes is the 15 bp '10-23' catalytic motif (that is, "10-23" is the name of the clone), GGCTAGCTACAACGA (Finkel, 1999, Science 286: 2441-2442; Sriram et al., 2000, Biochem J. 15: 667-673; Sun et al., 1999, J. Biol. Chem. 274: 17236-17241). Several examples of DNA enzymes comprising the '10-23' catalytic motif include DNA enzymes which target HIV-1 gag RNA (Sriram et al., 2000, Biochem J. 15: 667-673), and c-myc RNA (Sun et al., 1999, J. Biol. Chem. 274: 17236-17241), and egr-1 mRNA (Santiago et al., 1999, Nature Med. 11: 1264-1269). Such DNA enzymes can comprise a catalytic domain of about 15 bp further comprising flanking regions of 6 to 10 bp on both sides of the catalytic domain. The flanking regions can share about 100% homology with human PCADM-1 (SEQ ID NO:1) (see FIGS. 2 and 3). Thus, one skilled in the art and armed with the disclosure provided herein would appreciate that an active PCADM-1 DNAZYM or DNA enzyme comprises an enzymatic center, also referred to as a catalytic core, similar to those exemplified elsewhere herein and/or known in the art, and further comprises binding arms that can bind PCADM-1 mRNA such that cleavage at a target site occurs. The DNAZYMs of the invention can comprise additional sequences, which do not interfere with such cleavage, as would be understood by the skilled artisan, based upon the disclosure provided herein.

In general, enzymatic nucleic acids act by first specifically binding with a target RNA. Binding is mediated by the target binding portion of the enzymatic nucleic acid (i.e., the flanking binding regions or "arms"), such that the enzymatic nucleic acid enzymatic core domain is held in close proximity to a target RNA and cleavage then occurs. Thus, the enzymatic nucleic acid first recognizes and then binds a target RNA through complementary base-pairing, and once bound to the correct site, acts enzymatically to cleave the target RNA. Strategic cleavage of such a target RNA can destroy its ability to direct synthesis of an encoded protein. After an enzymatic nucleic acid has bound and cleaved its RNA target, it is released from that RNA to search for another target and can repeatedly bind and cleave new targets, such that a single DNAZYM molecule can cleave more than one target RNA molecule.

The enzymatic nature of a DNAZYM is advantageous over other technologies, since the DNAZYM does not require phosphoriate modifications and is relatively stable to nucleases. One other advantage of a DNAZYM is that the "half-life" of a DNAZYM in vivo is days rather than hours as reported for ribozymes. A single DNAZYM molecule is able to cleave many molecules of target RNA. In addition, the DNAZYM is a highly specific inhibitor, with the specificity of inhibition depending not only on the base-pairing mechanism of the flanking sequences binding to the target RNA, but also on the mechanism of target RNA cleavage. Single mismatches, or base-substitutions, near the site of cleavage can be selected to completely eliminate catalytic activity of a DNAZYM and provide a negative control oligonucleotide in experimental studies.

Nucleic acid molecules having an endonuclease enzymatic activity are able to repeatedly cleave other separate RNA molecules in a nucleotide base sequence-specific manner. Such enzymatic DNA or RNA molecules can be targeted to virtually any RNA transcript, and efficient cleavage is achieved in vitro (Zaug et al., 1986, Nature 324:429; Uhlenbeck, 1987, Nature 328:596; Kim et al., 1987, Proc. Natl. Acad. Sci. USA 84:8788; Dreyfus, 1988, Einstein Quart. J. Bio. Med. 6:92; Haseloff and Gerlach, 1988, Nature 334:585; Cech, 1988, J. Amer. Med. Assn. 260:3030; and Jefferies et al., 1989, Nucleic Acids Res. 17:1371).

Because of their sequence-specificity, trans-cleaving DNAZYMs are important potential therapeutic agents for human disease. DNAZYMs can be designed to cleave specific RNA targets within the background of cellular RNA. Such a cleavage event renders the RNA non-functional and abrogates protein expression from that RNA. In this manner, synthesis of a protein associated with a disease state can be selectively inhibited.

DNAZYMs that cleave the specified sites in PCADM-1 mRNAs (i.e., PCADM-1 DNAZYM-1 SEQ ID NO:9 and SEQ ID NO:10), represent a novel therapeutic approach to treat diseases, such as cancer and other conditions. The data disclosed elsewhere herein demonstrates that PCADM-1 DNAZYMs inhibit the activity of PCADM-1 and that the catalytic activity of the PCADM-1 DNAZYM is required for the inhibitory effect. Those of ordinary skill in the art, will find that it is clear from the disclosure provided herein, that additional PCADM-1 DNAZYMs that cleave PCADM-1 RNA can be readily designed based upon the disclosure provided herein and that such DNAZYMs are within the scope of the invention.

In one of the preferred embodiments of the inventions herein, the enzymatic nucleic acid molecule comprises a '10-

23' motif, a hammerhead motif or hairpin motif. DNAZYMs with the '10-23' catalytic motif (GGCTAGCTACAACGA) include DNAZYMs which target HIV-1 gag RNA (Sriram and Banerjea, 2000, Biochem J. 15: 667-673), and c-myc RNA (Sun et al., 1999, Biol. Chem. 274: 17236-17241), and egr-1 mRNA (Santiago et al., 1999, Nature Med. 11: 1264-1269). Examples of hammerhead motifs are described by Dreyfus, supra, Rossi et al. (1992, AIDS Research and Human Retroviruses 8:183). Examples of hairpin motifs are described in, e.g., Hampel et al. (EP0360257), Hampel et al. (1997, Methods Mol. Biol. 74: 171-177), Feldstein et al. (1989, Gene 82: 53-61), Haseloff and Gerlach (1989, Nature, 334: 585-591) and Hampel et al. (2001, Methods Enzymol. 341: 566-580).

The specific motifs discussed elsewhere herein are not limiting in the invention and those skilled in the art would recognize, based upon the disclosure provided herein, that all that is important in an enzymatic nucleic acid molecule (or multiple fragments of such molecules) of this invention is that the DNAZYM comprise a specific substrate binding site or arm(s) flanking the catalytic domain, which binding arm is complementary to one or more of the target RNA sequence, and that the DNAZYM further comprise nucleotide sequences within or surrounding that substrate binding site which impart an RNA cleaving activity to the molecule (i.e., an enzymatic portion).

Such arms flanking the catalytic core of a DNAZYM are exemplified herein (e.g., SEQ ID NO:9 and SEQ ID NO:10) and are depicted, diagrammatically, in FIGS. 2 and 3, respectively. That is, these arms contain sequences at the 5' and 3' ends of a DNAZYM, which are intended to bring DNAZYM and target PCADM-1 RNA in sufficient proximity with each other via complementary base-pairing interactions, e.g., DNAZYM sequences SEQ ID NO:9 and SEQ ID NO:10 comprise binding arms (i.e., 8 to 10 base pairs) flanking the catalytic domain of the DNA enzyme thereby comprising a substrate-binding domain.

In one aspect the invention encompasses a method for designing and/or producing an enzymatic cleaving agent (i.e., PCADM-1 DNAZYMs or DNA enzymes), which exhibit a high degree of specificity for the RNA of a desired target, i.e., it specifically cleaves PCADM-1 mRNA but not other mRNA that may be present in a sample. Therefore, once armed with the teachings provided herein, inter alia, the sequence of PCADM-1, the surprising discovery that PCADM-1 is associated with and/or is diagnostic for prostate cancer, and the reduction to practice of two PCADM-1 DNAZYMs exemplified herein (i.e., PCADM-1 DNAZYM-1 (SEQ ID NO:9) and PCADM-1 DNAZYM-2 (SEQ ID NO:10)), the skilled artisan, based upon the disclosure provided herein, can produce and/or design DNA enzymes that specifically cleave PCADM-1 mRNA.

The enzymatic nucleic acid molecule is preferably targeted to a highly conserved sequence region of a target mRNA encoding PCADM-1 proteins (i.e., the 5' mRNA region comprising from about nucleotide −9 to about nucleotide +450 from the AUG translational start site.). This is because one skilled in the art of producing DNA enzymes would appreciate, based upon the disclosure provided herein, that a DNAZYM that specifically cleaves PCADM-1 mRNA can be produced by selecting a PCADM-1 DNAZYM which preferably targets the 5' end of the mRNA, since a truncated PCADM-1 protein can comprise a biological activity or property similar to the intact PCADM-1 protein. In addition, PCADM-1 DNAZYMs which target regions (including overlapping regions), spanning the 5' end up to about 450 bases from the 5' translational start site of the PCADM-1 mRNA sequence, are particularly valuable. That is, without wishing to be bound by any particular theory, any short peptides that may be expressed by the residual mRNA (i.e., following PCADM-1 DNAZYM treatment) would not contain the downstream leucine zipper-like domain, which domain contains PCADM-1 mutation sites and the presumptive DNA binding domain. In this regard, PCADM-1-DNAZYM-1 targets sequences 155 to 171 of the PCADM-1 mRNA, and PCADM-1-DNAZYM-2 targets sequences −7 to +9 of the PCADM-1 mRNA (i.e. from the AUG translational start sites of the PCADM-1 mRNA).

Thus, binding arms comprising sequences complementary to these regions of PCADM-1 mRNA can be synthesized, or otherwise produced, such that they are covalently linked to a nucleic acid comprising a catalytic domain that can cleave a ribonucleic acid. The DNA enzyme activity of the molecule thus produced can be assessed by, among other assays well-known in the art, assessing the ability of the molecule to cleave PCADM-1 mRNA, to identify the DNA enzymes of the invention. Methods of synthesizing these molecules, and for assessing their DNA enzyme activity, are well-known in the art and/or are described elsewhere herein.

The skilled artisan, armed with the teachings provided herein, would understand that the invention encompasses treatment of a disease or condition using at least one enzymatic nucleic acid. That is, one skilled in the art would appreciate, based upon the disclosure provided herein, that DNAZYMs or enzymatic nucleic acids can be used in combination with each other, and also in combination with other compounds including, but not limited to, chemotherapeutic agents, small molecules, peptidomimetics, anti-sense, ribozymes, antibodies, and the like. Thus, the invention is not limited to using a single enzymatic nucleic acid by itself; rather, the invention compasses using other DNAZYMs such as, DNA enzyme against MMP-2 and VEGF-1, and the like, in combination with at least one DNAZYM that specifically cleaves PCADM-1 mRNA. An enzymatic nucleic acid molecule can be delivered exogenously to specific cells or tissues, as required. The PCADM-1 DNAZYM of the invention are useful for the treatment, prevention, or both, of the diseases and conditions discussed above (e.g., prostate cancer), and any other diseases or conditions that are related to an increased level of PCADM-1 activity in a cell or tissue compared with the level of PCADM-1 activity in a cell or tissue not afflicted with a disease or condition.

PCADM-1 DNAZYMs are administered to a cell directly, or can be complexed with cationic lipids, packaged within liposomes, or otherwise delivered to a cell. The nucleic acid or nucleic acid complexes can be locally administered to relevant tissues ex vivo, or in vivo through injection, infusion pump or stent, with or without their incorporation in biopolymers. In preferred embodiments, the PCADM-1 DNAZYMs comprise binding arms (8-10 bps) complementary with the sequence of SEQ ID NO:1, depicted in FIG. 1A.

Thus, in one aspect, the invention includes a PCADM-1 DNAZYM that inhibits gene expression and/or cell proliferation via cleavage of RNA expressed from a nucleic acid encoding PCADM-1. These chemically or enzymatically synthesized DNA molecules comprise a binding domain, i.e., a "binding arm", that bind with an accessible region of their target mRNA.

The DNA molecule further comprises a catalytic core or domain that catalyzes the cleavage of mRNA. The DNA molecules preferably comprise a '10-23' motif catalytic core. Upon binding, the PCADM-1 DNAZYM cleaves the target mRNA, preventing translation, protein accumulation, or both. In the absence of the expression of the target mRNA, cell proliferation and/or survival are inhibited.

In one embodiment, the PCADM-1 DNAZYMs cleave PCADM-1 mRNA and inhibit cell proliferation and/or survival. Such PCADM-1 DNAZYMs are useful for the prevention and/or treatment of cancer or other diseases. PCADM-1 DNAZYMs are added directly, or can be complexed with cationic lipids, packaged within liposomes, or otherwise delivered to smooth muscle cells. The DNA or DNA complexes can be locally administered to relevant tissues through the use of a catheter, infusion pump or stent, with or without their incorporation in biopolymers. The PCADM-1 DNAZYMs, similarly delivered, also are useful for inhibiting proliferation and/or survival of certain cancers associated with elevated levels of the PCADM-1, particularly prostate cancer. Using the methods described herein, various PCADM-1 DNAZYMs that cleave PCADM-1 mRNA and thereby inhibit tumor cell proliferation and/or survival can be produced, identified, and used as described elsewhere herein.

These PCADM-1 DNAZYMs, individually, or in combination or in conjunction with other drugs, can be used to treat diseases or conditions as disclosed elsewhere herein. For example, the DNAZYM can be used to treat a disease or condition associated with PCADM-1 levels, the patient can be treated, or other appropriate cells may be treated, as is evident to those skilled in the art, based upon the disclosure provided herein.

In a further embodiment, the described PCADM-1 DNAZYMs can be used in combination with other known treatments or surgical procedures (e.g., cryoablation), to treat conditions or diseases discussed above. For example, the described PCADM-1 DNAZYMs could be used in combination with one of more known therapeutic agents to treat cancer.

Target mRNA

One skilled in the art would appreciate, based upon the disclosure provided herein, that PCADM-1 DNAZYMs can be designed to specifically target PCADM-1 mRNA. Those PCADM-1 DNAZYMs with unfavorable intramolecular interactions between the binding arms and the catalytic core are eliminated from consideration using various assays exemplified herein or assays well-known in the art.

The skilled artisan would understand, based upon the teachings provided herein, that binding arm length can be selected to optimize mRNA cleaving activity. Generally, at least about 6 to 8 bases on each arm are sufficient to bind with, or otherwise interact with, the target mRNA. The PCADM-1 DNAZYMs exemplified herein were chemically synthesized. The method of synthesis used follows the procedure for normal oligonucleotide synthesis as described in Usman et al. (1987, J. Am. Chem. Soc. 109:7845), Scaringe et al. (1990, Nucleic Acids Res. 18:5433), and Wincott et al. (1995, Nucleic Acids Res. 23: 2677-2684), and makes use of common nucleic acid protecting and coupling groups, such as dimethoxytrityl at the 5'-end, and phosphoramidites at the 3'-end. However, the present invention is not limited to any particular method of producing the DNAZYM of the invention.

One skilled in the art would understand, based upon the disclosure provided herein, that once armed with the sequence of a nucleic acid encoding PCADM-1 (e.g., a nucleic acid sharing greater than about 98% sequence identity with SEQ ID NO:1), it would be routine for the skilled artisan to produce various DNAZYMs that specifically cleave an mRNA encoding a PCADM-1 polypeptide. That is, by selecting various 6-10 base pair 'arms' nucleotide sequences along the mRNA sequence and assaying the putative DNAZYM for PCADM-1 mRNA cleaving activity as disclosed herein, or as known in the art or as developed in the future, various PCADM-1 specific enzymatic nucleic acids can be identified and produced. Therefore, such enzymatic nucleic acids that specifically cleave PCADM-1 mRNA are encompassed in the present invention. Preferably, an enzymatic nucleic acid that specifically cleaves PCADM-1 mRNA comprises at least one binding arm ranging in size from about 6 to 10 nucleotides in length. More preferably, the enzymatic nucleic acid comprises at least one binding arm complementary to the sequence of PCADM-1 mRNA from about −9 to about +450 relative to the AUG translational start site as set forth in SEQ ID NO:1. Even more preferably, a binding arm is complementary to the sequence from about −7 to about +9 of SEQ ID NO:1, and from about +155 to +171 of SEQ ID NO:1 relative to the translational start site. Such enzymes include, but are not limited to, those exemplified herein having the sequence GATCTTCAGGCTAGCTACAACGAGTCCTTGA (SEQ ID NO. 9) and GTTCCCCAGGCTAGCTACAACGAC-CCAGGGC (SEQ ID NO. 10).

PCADM-1 DNAZYMs can be purified by gel electrophoresis using general methods or purified by high pressure liquid chromatography (HPLC; see Wincott et al., supra, which is hereby incorporated herein by reference) and are resuspended in water.

Optimizing PCADM-1 DNAZYM Activity

DNAZYM activity can be optimized as described by Draper et al., supra. The details will not be repeated here, but include altering the length of the DNA enzyme binding arms (from about 6 to 10 base pairs), or chemically synthesizing PCADM-1 DNAZYMs with modifications (base, sugar and/or phosphate) that prevent their degradation by serum Dnase and/or that enhance their enzymatic activity (see, e.g., Eckstein et. al., International Publication No. WO 92/07065; Perrault et al., 1990, Nature 344:565; Pieken et al., 1991, Science 253:314; Usman and Cedergren, 1992, Trends in Biochem. Sci. 17:334; Usman et al., International Publication No. WO 93/15187; and Rossi et al., International Publication No. WO 91/03162; Sproat, U.S. Pat. No. 5,334,711; and Burgin et al., supra).

PCADM-1 DNAZYMs may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules or polymer matrices, and bioadhesive microspheres. For some indications, PCADM-1 DNAZYMs can be directly delivered ex vivo to cells or tissues with or without the aforementioned vehicles. Alternatively, the DNA/vehicle combination is locally delivered by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of DNAZYM delivery and administration are provided in Sullivan et al., supra, and Draper et al., supra, which have been incorporated by reference herein.

V. Recombinant Cells and Transgenic Non-Human Mammals

The invention includes a recombinant cell comprising, inter alia, an isolated nucleic acid encoding PCADM-1. In one aspect, the recombinant cell comprising an isolated nucleic acid encoding mammalian PCADM-1 is used to produce a transgenic non-human mammal. That is, the exogenous nucleic acid, or transgene as it is also referred to herein, of the invention is introduced into a cell, and the cell is then used to generate the non-human transgenic mammal. The cell into which the transgene is introduced is preferably an embryonic stem (ES) cell. However, the invention should not be construed to be limited solely to ES cells comprising the transgene of the invention nor to cells used to produce transgenic animals. Rather, a transgenic cell of the invention includes, but is not limited to, any cell derived from a transgenic animal comprising a transgene, a cell comprising the transgene derived from a chimeric animal derived from the transgenic ES cell, and any other comprising the transgene which may or may not be used to generate a non-human transgenic mammal.

Further, it is important to note that the purpose of transgene-comprising, i.e., recombinant, cells should not be construed to be limited to the generation of transgenic mammals. Rather, the invention should be construed to include any cell type into which a nucleic acid encoding a mammalian PCADM-1 is introduced, including, without limitation, a prokaryotic cell and a eukaryotic cell comprising an isolated nucleic acid encoding mammalian PCADM-1.

When the cell is a eukaryotic cell, the cell may be any eukaryotic cell, which when the transgene of the invention is introduced therein, and the protein encoded by the desired gene is no longer expressed there from, a benefit is obtained. Such a benefit may include the fact that there has been provided a system in which lack of expression of the desired gene can be studied in vitro in the laboratory or in a mammal in which the cell resides, a system wherein cells comprising the introduced gene deletion can be used as research, diagnostic and therapeutic tools, and a system wherein animal models are generated which are useful for the development of new diagnostic and therapeutic tools for selected disease states in a mammal including, for example, prostate cancer, and the like.

Alternatively, the invention includes a eukaryotic cell which, when the transgene of the invention is introduced therein, and the protein encoded by the desired gene is expressed there from where it was not previously present or expressed in the cell or where it is now expressed at a level or under circumstances different than that before the transgene was introduced, a benefit is obtained. Such a benefit may include the fact that there has been provided a system in the expression of the desired gene can be studied in vitro in the laboratory or in a mammal in which the cell resides, a system wherein cells comprising the introduced gene can be used as research, diagnostic and therapeutic tools, and a system wherein animal models are generated which are useful for the development of new diagnostic and therapeutic tools for selected disease states in a mammal.

Such cell expressing an isolated nucleic acid encoding PCADM-1 can be used to provide PCADM-1 to a cell, tissue, or whole animal where a higher level of PCADM-1 can be useful to treat or alleviate a disease, disorder or condition associated with low level of PCADM-1 expression and/or activity. Such diseases, disorders or conditions can include, but are not limited to prostate cancer, and possibly other solid cancers or leukemias, AIDS, HIV infection, immune disorders and inflammatory or degenerative disorders, and the like. Therefore, the invention includes a cell expressing PCADM-1 to increase or induce PCADM-1 expression, translation, and/or activity, where increasing PCADM-1 expression, protein level, and/or activity can be useful to treat or alleviate a disease, disorder or condition.

One of ordinary skill would appreciate, based upon the disclosure provided herein, that a "knock-in" or "knock-out" vector of the invention comprises at least two sequences homologous to two portions of the nucleic acid which, is to be replaced or deleted, respectively. The two sequences are homologous with sequences that flank the gene; that is, one sequence is homologous with a region at or near the 5' portion of the coding sequence of the nucleic acid encoding PCADM-1 and the other sequence is further downstream from the first. One skilled in the art would appreciate, based upon the disclosure provided herein, that the present invention is not limited to any specific flanking nucleic acid sequences. Instead, the targeting vector may comprise two sequences, which remove some, or all (i.e., a "knock-out" vector) or which insert (i.e., a "knock-in" vector) a nucleic acid encoding PCADM-1, or a fragment thereof, from or into a mammalian genome, respectively. The crucial feature of the targeting vector is that it comprise sufficient portions of two sequences located towards opposite, i.e., 5' and 3', ends of the PCADM-1 open reading frame (ORF) in the case of a "knock-out" vector, to allow deletion/insertion by homologous recombination to occur such that all or a portion of the nucleic acid encoding PCADM-1 is deleted from or inserted into a location on a mammalian chromosome.

The design of transgenes and knock-in and knock-out targeting vectors is well-known in the art and is described in standard treatises such as Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York), and the like. The upstream and downstream portions flanking or within the PCADM-1 coding region to be used in the targeting vector may be easily selected based upon known methods and following the teachings disclosed herein based on the disclosure provided herein including the nucleic and amino acid sequences of both mouse and human PCADM-1. Armed with these sequences, one of ordinary skill in the art would be able to construct the transgenes and knockout vectors of the invention.

The invention further includes a knock-out targeting vector comprising a nucleic acid encoding a selectable marker such as, for example, a nucleic acid encoding the $neo^R$ gene thereby allowing the selection of a transgenic cell where the nucleic acid encoding PCADM-1, or a portion thereof, has been deleted and replaced with the neomycin resistance gene by the cell's ability to grow in the presence of G418. However, the present invention should not be construed to be limited to neomycin resistance as a selectable marker. Rather, other selectable markers well-known in the art may be used in the knock-out targeting vector to allow selection of recombinant cells where the PCADM-1 gene has been deleted and/or inactivated and replaced by the nucleic acid encoding the selectable marker of choice. Methods of selecting and incorporating a selectable marker into a vector are well-known in the art and are describe in, for example, Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York).

As noted herein, the invention includes a non-human transgenic mammal comprising an exogenous nucleic acid inserted into a desired site in the genome thereof thereby deleting the coding region of a desired endogenous target gene, i.e., a knock-out transgenic mammal. Further, the invention includes a transgenic non-human mammal wherein an exogenous nucleic acid encoding PCADM-1 is inserted into a site the genome, i.e., a "knock-in" transgenic mammal. The knock-in transgene inserted may comprise various nucleic acids encoding, for example, a polypeptide, and a promoter/regulatory region operably linked to the nucleic acid encoding PCADM-1 not normally present in the cell or not typically operably linked to PCADM-1.

The generation of the non-human transgenic mammal of the invention is preferably accomplished using the method, which, is now described. However, the invention should in no way be construed as being limited solely to the use of this method, in that, other methods can be used to generate the desired knock-out mammal.

In the preferred method of generating a non-human transgenic mammal, ES cells are generated comprising the transgene of the invention and the cells are then used to generate the knock-out animal essentially as described in Nagy and Rossant (1993, In: Gene Targeting, A Practical Approach, pp. 146-179, Joyner, ed., IRL Press). ES cells behave as normal embryonic cells if they are returned to the embryonic environment by injection into a host blastocyst or aggregate with blastomere stage embryos. When so returned, the cells have the full potential to develop along all lineages of the embryo. Thus, it is possible, to obtain ES cells, introduce a desired DNA therein, and then return the cell to the embryonic environment for development into mature mammalian cells, wherein the desired DNA may be expressed.

Precise protocols for the generation of transgenic mice are disclosed in Nagy and Rossant (1993, In: Gene Targeting, A Practical Approach, Joyner, ed., IRL Press, pp. 146-179), and are therefore not repeated herein. Transfection or transduction of ES cells in order to introduce the desired DNA therein is accomplished using standard protocols, such as those described, for example, in Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York). Preferably, the desired DNA contained within the transgene of the invention is electroporated into ES cells, and the cells are propagated as described in Soriano et al. (1991, Cell 64: 693-702).

Introduction of an isolated nucleic acid into the fertilized egg of the mammal is accomplished by any number of standard techniques in transgenic technology (Hogan et al., 1986, Manipulating the Mouse Embryo: A Laboratory Manual, Cold Spring Harbor, N.Y.). Most commonly, the nucleic acid is introduced into the embryo by way of microinjection.

Once the nucleic acid is introduced into the egg, the egg is incubated for a short period of time and is then transferred into a pseudopregnant mammal of the same species from which the egg was obtained as described, for example, in Hogan et al. (1986, Manipulating the Mouse Embryo: A Laboratory Manual, Cold Spring Harbor, N.Y.). Typically, many eggs are injected per experiment, and approximately two-thirds of the eggs survive the procedure. About twenty viable eggs are then transferred into pseudopregnant animals, and usually four to ten of the viable eggs so transferred will develop into live pups.

Any mammalian PCADM-1 gene may be used in the methods described herein to produce a transgenic mammal or a transgenic cell harboring a transgene comprising a deletion of all or part of that mammalian PCADM-1 gene. Preferably, a rodent PCADM-1 is used.

The transgenic mammal of the invention can be any species of mammal. Thus, the invention should be construed to include generation of transgenic mammals encoding the chimeric nucleic acid, which mammals include mice, hamsters, rats, rabbits, pigs, sheep and cattle. The methods described herein for generation of transgenic mice can be analogously applied using any mammalian species. Preferably, the transgenic mammal of the invention is a rodent and even more preferably, the transgenic mammal of the invention is a mouse. By way of example, Lukkarinen et al. (1997, Stroke 28: 639-645), teaches that gene constructs, which enable the generation of transgenic mice, also enable the generation of other transgenic rodents, including rats. Similarly, nullizygous mutations in a genetic locus of an animal of one species can be replicated in an animal of another species having a genetic locus highly homologous to the first species.

To identify the transgenic mammals of the invention, pups are examined for the presence of the isolated nucleic acid using standard technology such as Southern blot hybridization, PCR, and/or RT-PCR. Expression of the nucleic acid in the cells and in the tissues of the mammal is also assessed using ordinary technology described herein. Further, the presence or absence of PCADM-1 in the circulating blood of the transgenic animal can be determined, for example, as disclosed herein (e.g., Western blot analysis), or using standard methods for protein detection that are well-known in the art.

Cells obtained from the transgenic mammal of the invention, which are also considered "transgenic cells" as the term is used herein, encompass such as cells as those obtained from the PCADM-1 (+/−) and (−/−) transgenic non-human mammal described elsewhere herein, are useful systems for modeling diseases and symptoms of mammals which are believed to be associated with altered levels of PCADM-1 expression such as prostate cancer, and any other disease, disorder or condition associated with an altered level of PCADM-1 expression.

Moreover, as a marker of a pathway(s) associated with tumor proliferation and other abnormalities such prostate, PCADM-1 expression levels are also useful indicators in assessment of such diseases, disorders or conditions.

Particularly suitable are cells derived from a tissue of the non-human knock-out or knock-in transgenic mammal described herein, wherein the transgene comprising the PCADM-1 gene is expressed or inhibits expression of PCADM-1 in various tissues. By way of example, cell types from which such cells are derived include fibroblasts, endothelial, adipocyte, and myoblast cells of (1) the PCADM-1 (+/+), (+/−) and (−/−) non-human transgenic live born mammal, (2) the PCADM-1 (+/+), (−/−) or (+/−) fetal animal, and (3) placental cell lines obtained from the PCADM-1 (+/+), (−/−) and (+/−) fetus and live born mammal.

One skilled in the art would appreciate, based upon this disclosure, that cells comprising decreased levels of PCADM-1 protein, decreased level of PCADM-1 activity, or both, include, but are not limited to, cells expressing inhibitors of PCADM-1 expression (e.g., DNAZYMs, antisense or ribozyme molecules).

Methods and compositions useful for maintaining mammalian cells in culture are well known in the art, wherein the mammalian cells are obtained from a mammal including, but not limited to, cells obtained from a mouse such as the transgenic mouse described herein, or cells obtained from primate and non-primate mammals.

The recombinant cell of the invention can be used to produce PCADM-1 for use for therapeutic and/or diagnostic purposes. That is, a recombinant cell expressing PCADM-1 can be used to produce large amounts of purified and isolated PCADM-1 that can be administered to treat or alleviate a disease, disorder or condition associated with or caused by a decreased level of PCADM-1.

Alternatively, recombinant cells expressing PCADM-1 can be administered in ex vivo and in vivo therapies where administering the recombinant cells thereby administers the protein to a cell, a tissue, and/or an animal. Additionally, the recombinant cells are useful for the discovery of PCADM-1 receptor and PCADM-1 signaling pathways.

The recombinant cell of the invention may be used to study the effects of elevated or decreased PCADM-1 levels on cell homeostasis and cell proliferation since PCADM-1 has been hypothesized to play a role in prostate cancer, and the like.

The recombinant cell of the invention, wherein the cell has been engineered such that it does not express PCADM-1, or expresses reduced or altered PCADM-1 lacking biological activity, can also be used in ex vivo and in vivo cell therapies where either an animal's own cells (e.g., epithelial cells, fibroblast cells, smooth muscle cells, white blood cells, dendritic cells, and the like) or those of a syngeneic matched donor are recombinant engineered as described elsewhere herein (e.g., by insertion of an antisense nucleic acid or a knock-out vector such that PCADM-1 expression and/or protein levels are thereby reduced in the recombinant cell), and the recombinant cell is administered to the recipient animal. In this way, recombinant cells that express PCADM-1 at a reduced level can be administered to an animal whose own cells express increased levels of PCADM-1 thereby treating or alleviating a disease, disorder or condition associated with or mediated by increased PCADM-1 expression as disclosed elsewhere herein.

The transgenic mammal of the invention, rendered susceptible to prostate cancer, can be used to study the pathogenesis of prostate cancer and the possible role of PCADM-1 therein.

Further, the transgenic mammal and/or cell of the invention may be used to study the subcellular localization of PCADM-1.

Also, the transgenic mammal (both +/− and −/− live born and fetuses) and/or cell of the invention may be used to study to role(s) of PCADM-1 in glucose metabolism and to elucidate the target(s) of PCADM-1 action as well as any receptor(s) that bind with PCADM-1 to mediate its effect(s) in the cell.

VI. Antibodies

The invention also includes an antibody that specifically binds PCADM-1, or a fragment thereof.

In one embodiment, the antibody is directed to human PCADM-1 comprising the amino acid sequence of SEQ ID NO:2, or an immunogenic portion thereof.

Polyclonal antibodies are generated by immunizing rabbits according to standard immunological techniques well-known in the art (see, e.g., Harlow et al., 1988, In: Antibodies, A Laboratory Manual, Cold Spring Harbor, N.Y.). The antibodies exemplified herein were produced using standard techniques whereby the animal was immunized with recombinantly produced antigen and boosted repeatedly using antigen according to standard art-recognized methodologies. However, the present invention is not limited to this, or any other, approach and it should be understood that antibodies can be produced by such methods, but not limited to, as immunizing an animal with a chimeric protein comprising a portion of another protein such as a maltose binding protein or glutathione (GSH) tag polypeptide portion, and/or a moiety such that the PCADM-1 portion is rendered immunogenic (e.g., PCADM-1 conjugated with keyhole limpet hemocyanin, KLH) and a portion comprising the respective rodent and/or human PCADM-1 amino acid residues. The chimeric proteins are produced by cloning the appropriate nucleic acids encoding PCADM-1 (e.g., SEQ ID NO:1) into a plasmid vector suitable for this purpose, such as but not limited to, pBK-CMV, pMAL-2 or pCMX.

However, the invention should not be construed as being limited solely to these antibodies or to these portions of the protein antigens. Rather, the invention should be construed to include other antibodies, as that term is defined elsewhere herein, that specifically binds with mouse and human PCADM-1, or portions thereof. Further, the present invention should be construed to encompass antibodies that, inter alia, bind to PCADM-1 and they are able to bind PCADM-1 present on Western blots, in solution in enzyme linked immunoassays, in fluorescence activated cells sorting (FACS) assays, in immunohistochemical staining of tissues thereby localizing PCADM-1 in the tissues, and in immunofluorescence microscopy of a cell transiently transfected with a nucleic acid encoding at least a portion of PCADM-1.

One skilled in the art would appreciate, based upon the disclosure provided herein, that the antibody can specifically bind with any portion of the protein and the full-length protein can be used to generate antibodies specific therefor. However, the present invention is not limited to using the full-length protein as an immunogen. Rather, the present invention includes using an immunogenic portion of the protein to produce an antibody that specifically binds with mammalian PCADM-1. That is, the invention includes immunizing an animal using an immunogenic portion, or antigenic determinant, of the PCADM-1 protein.

The antibodies can be produced by immunizing an animal such as, but not limited to, a rabbit or a mouse, with a protein of the invention, or a portion thereof, or by immunizing an animal using a protein comprising at least a portion of PCADM-1, or a fusion protein including a tag polypeptide portion comprising, for example, a maltose binding protein tag polypeptide portion, covalently linked with a portion comprising the appropriate PCADM-1 amino acid residues. One skilled in the art would appreciate, based upon the disclosure provided herein, that smaller fragments of these proteins can also be used to produce antibodies that specifically bind PCADM-1.

One skilled in the art would appreciate, based upon the disclosure provided herein, that various portions of an isolated PCADM-1 polypeptide can be used to generate antibodies to either highly conserved regions of PCADM-1 or to non-conserved regions of the polypeptide including regions containing mutations.

Once armed with the sequence of PCADM-1 and the detailed analysis localizing the various conserved and non-conserved domains of the protein, the skilled artisan would understand, based upon the disclosure provided herein, how to obtain antibodies specific for the various portions of a mammalian PCADM-1 polypeptide using methods well-known in the art or to be developed.

Further, the skilled artisan, based upon the disclosure provided herein, would appreciate that the non-conserved regions of a protein of interest can be more immunogenic than the highly conserved regions, which are conserved among various organisms. Further, immunization using a non-conserved immunogenic portion can produce antibodies specific for the non-conserved region thereby producing antibodies that do not cross-react with other proteins, which, can share one or more conserved portions. Thus, one skilled in the art would appreciate, based upon the disclosure provided herein, that the non-conserved regions of each PCADM-1 molecule can be used to produce antibodies that are specific only for that PCADM-1 and do not cross-react non-specifically with other PCADM-1s or with other proteins, e.g., with human S2. More specifically, the skilled artisan would appreciate, based upon the disclosure provided herein, that PCADM-1 and S2 differ in that PCADM-1 comprises five amino acids that differ from the same residues of S2, i.e., PCADM-1 comprises an T (threonine) at amino acid residue number 64, N (asparagine) at amino acid residue number 155, an A (alanine) at residue number 159, an R (arginine) at residue number 163, and an R (arginine) at residue number 169 relative to the amino acid sequence of SEQ ID NO:2, all of which differ from the amino acid residue at that same position of the amino acid sequence of human S2 (see, e.g., GenBank Accession No. XM045032, Human S2 40S ribosomal protein).

Alternatively, the skilled artisan would also understand, based upon the disclosure provided herein, that antibodies developed using a region that is conserved among one or more PCADM-1 molecule can be used to produce antibodies that react specifically with one or more PCADM-1 molecule and with human S2, which shares about 98% amino acid homology with PCADM-1. That is, the skilled artisan would understand that portions of S2 and PCADM-1 that do not comprise the region of amino acid substitutions (i.e., amino acid residue numbers 64, 155, 159, 163 and 169) can be used to produce antibodies that specifically bind with S2 and with PCADM-1 and that these antibodies can also be used for the methods of the invention. The sequence of S2 is well known in the art and includes, but is not limited to, the sequence of GenBank Accession No. XM045032, and the like.

Methods for producing antibodies that specifically bind with a conserved protein domain which may otherwise be less immunogenic than other portions of the protein are well-known in the art and include, but are not limited to, conjugating the protein fragment of interest to a molecule (e.g., keyhole limpet hemocyanin, and the like), thereby rendering the protein domain immunogenic, or by the use of adjuvants (e.g., Freund's complete and/or incomplete adjuvant, and the like), or both. Thus, the invention encompasses antibodies that recognize at least one PCADM-1 and antibodies that specifically bind with more than one PCADM-1, including antibodies that specifically bind with all PCADM-1 and/or with S2.

One skilled in the art would appreciate, based upon the disclosure provided herein, which portions of PCADM-1 are less homologous with other proteins sharing conserved domains. However, the present invention is not limited to any particular domain; instead, the skilled artisan would understand that other non-conserved regions of the PCADM-1 proteins of the invention can be used to produce the antibodies of the invention as disclosed herein.

Therefore, the skilled artisan would appreciate, based upon the disclosure provided herein, that the present invention encompasses antibodies that neutralize and/or inhibit PCADM-1 activity (e.g., by necessary PCADM-1/DNA binding interactions, and the like), which antibodies can recognize one or more PCADM-1s.

The invention should not be construed as being limited solely to the antibodies disclosed herein or to any particular immunogenic portion of the proteins of the invention. Rather, the invention should be construed to include other antibodies, as that term is defined elsewhere herein, to PCADM-1, or portions thereof, or to proteins sharing at least about 98% homology with a polypeptide having the amino acid sequence of SEQ ID NO:2. Preferably, the polypeptide is 99% homologous to human PCADM-1 (SEQ ID NO:2). More preferably, the polypeptide that specifically binds with an antibody specific for mammalian PCADM-1 is human PCADM-1. Most preferably, the polypeptide that specifically binds with an antibody that specifically binds with a mammalian PCADM-1 is SEQ ID NO: 2.

The invention encompasses polyclonal, monoclonal, synthetic antibodies, and the like. One skilled in the art would understand, based upon the disclosure provided herein, that the crucial feature of the antibody of the invention is that the antibody bind specifically with PCADM-1. That is, the antibody of the invention recognizes PCADM-1, or a fragment thereof (e.g., an immunogenic portion or antigenic determinant thereof), on Western blots, in immunostaining of cells, and immunoprecipitates PCADM-1 using standard methods well-known in the art.

One skilled in the art would appreciate that because of the high degree of similarity between PCADM-1 and 40S ribosomal S2 protein, antibodies to S2 can cross-react with PCADM-1. Such S2 antibodies are also useful for methods described in the present disclosure, as they can be used to detect PCADM-1. Thus, one skilled in the art would understand, based upon the disclosure provided herein, that antibodies that specifically bind with S2, and which also bind with PCADM-1, can be used in the methods of the invention as more fully set forth elsewhere herein.

One skilled in the art would appreciate, based upon the disclosure provided herein, that the antibodies can be used to localize the relevant protein in a cell and to study the role(s) of the antigen recognized thereby in cell processes. Moreover, the antibodies can be used to detect and or measure the amount of protein present in a biological sample using well-known methods such as, but not limited to, Western blotting and enzyme-linked immunosorbent assay (ELISA). Moreover, the antibodies can be used to immunoprecipitate and/or immuno-affinity purify their cognate antigen using methods well-known in the art. In addition, the antibody can be used to decrease the level of PCADM-1 in a cell thereby inhibiting the effect(s) of PCADM-1 in a cell. Thus, by administering the antibody to a cell or to the tissues of an animal or to the animal itself, the required PCADM-1 receptor/ligand interactions are therefore inhibited such that the effect of PCADM-1 mediated signaling are also inhibited. One skilled in the art would understand, based upon the disclosure provided herein, that detectable effects upon inhibiting PCADM-1 protein/nucleic acid binding interaction using an anti-PCADM-1 antibody can include, but are not limited to, decreased proliferation of prostate tumor cells, and the like.

The skilled artisan would appreciate, based upon the disclosure provided herein, that that present invention includes use of either a single antibody recognizing a single PCADM-1 epitope but that the invention is not limited to use of a single antibody. Instead, the invention encompasses use of at least one antibody where the antibodies can be directed to the same or different PCADM-1 epitopes.

The generation of polyclonal antibodies is accomplished by inoculating the desired animal with the antigen and isolating antibodies, which specifically bind the antigen there from using standard antibody production methods such as those described in, for example, Harlow et al. (1988, In: Antibodies, A Laboratory Manual, Cold Spring Harbor, N.Y.).

Monoclonal antibodies directed against full length or peptide fragments of a protein or peptide may be prepared using any well known monoclonal antibody preparation procedures, such as those described, for example, in Harlow et al. (1988, In: Antibodies, A Laboratory Manual, Cold Spring Harbor, N.Y.) and in Tuszynski et al. (1988, Blood, 72: 109-115). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

Nucleic acid encoding the monoclonal antibody obtained using the procedures described herein may be cloned and sequenced using technology which is available in the art, and is described, for example, in Wright et al. (1992, Critical Rev. Immunol. 12: 125-168), and the references cited therein.

Further, the antibody of the invention may be "humanized" using the technology described in, for example, Wright et al., id., and in the references cited therein, and in Gu et al. (1997, Thrombosis and Hematocyst 77: 755-759), and other methods of humanizing antibodies well-known in the art or to be developed.

To generate a phage antibody library, a cDNA library is first obtained from mRNA which is isolated from cells, e.g., the hybridoma, which express the desired protein to be expressed on the phage surface, e.g., the desired antibody. cDNA copies of the mRNA are produced using reverse transcriptase. cDNA, which specifies immunoglobulin fragments are obtained, by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al., supra.

Bacteriophage, which encode the desired antibody, may be engineered such that the protein is displayed on the surface thereof in such a manner that it is available for binding to its corresponding binding protein, e.g., the antigen against which the antibody is directed. Thus, when bacteriophage, which express a specific antibody, are incubated in the presence of a cell, which expresses the corresponding antigen, the bacteriophage will bind to the cell. Bacteriophage, which, do not express the antibody, will not bind to the cell. Such panning techniques are well known in the art and are described for example, in Wright et al. (supra).

Processes such as those described above, have been developed for the production of human antibodies using M13 bacteriophage display (Burton et al., 1994, Adv. Immunol. 57: 191-280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage, which display the antibody of interest, are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells, which express human immunoglobulin.

The procedures just presented describe the generation of phage, which, encode the Fab portion of an antibody molecule. However, the invention should not be construed to be limited solely to the generation of phage encoding Fab antibodies. Rather, phage which encode single chain antibodies (scFv/phage antibody libraries) are also included in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al. (1991, J. Mol. Biol. 222: 581-597). Panning of phage so generated for the isolation of a desired antibody is conducted in a manner similar to that described for phage libraries comprising Fab DNA.

The invention should also be construed to include synthetic phage display libraries in which the heavy and light chain variable regions may be synthesized such that they include nearly all possible specificities (Barbas, 1995, Nature Medicine 1: 837-839; de Kruif et al. 1995, J. Mol. Biol. 248: 97-105).

One skilled in the art would appreciate, based upon the disclosure provided herein, that present invention encompasses an immunotoxin comprising an antibody component that specifically binds with PCADM-1 linked to another agent, particularly a cytotoxic or otherwise anticellular agent, having the ability to kill or suppress the growth or cell division of cells. Such immunotoxins, or immuno-conjugates, are well known in the art and there are a plethora of toxic agents that can be used to produce them such as, but not limited to, ricin toxin, staphylococcal enterotoxin A (SEA) (Dohlsten et al., 1994, Proc. Natl. Acad. Sci. USA 91: 8945-8949), the plant toxin gelonin (Rosenblum et al., U.S. Pat. No. 5,624, 827), *Pseudomonas* exotoxin (PE), and the like. Therefore, the invention encompasses use of antibodies that specifically bind with PCADM-1 to preferentially target cytotoxic agents to tumor cells while minimizing the cytotoxic effect(s) to normal cells and tissues since, as disclosed herein, tumor cells express higher level of PCADM-1 than normal, non-tumor cells.

VII. Compositions

The invention includes a composition comprising an isolated nucleic complementary to a nucleic acid, or a portion thereof, encoding a mammalian PCADM-1, which is in an antisense orientation with respect to transcription. Preferably, the composition comprises a pharmaceutically acceptable carrier.

The invention includes a composition comprising an isolated nucleic complementary to a nucleic acid, or a portion thereof, encoding a mammalian PCADM-1, which is a DNAZYM or DNA enzyme that specifically cleaves PCADM-1. Preferably, the composition comprises a pharmaceutically acceptable carrier.

The invention includes a composition comprising an isolated mammalian PCADM-1 polypeptide as described herein. Preferably, the composition comprises a pharmaceutically-acceptable carrier.

The invention also includes a composition comprising an antibody that specifically binds PCADM-1. Preferably, the composition comprises a pharmaceutically-acceptable carrier.

The invention further includes a composition comprising an isolated nucleic acid encoding a mammalian PCADM-1. Preferably, the composition comprises a pharmaceutically acceptable carrier. The compositions can be used to administer PCADM-1, and/or a nucleic acid encoding the protein, to a cell, a tissue, or an animal or to inhibit expression of PCADM-1 in a cell, a tissue, or an animal. The compositions are useful to treat a disease, disorder or condition mediated by altered expression of PCADM-1 such that decreasing or increasing PCADM-1 expression or the level of the protein in a cell, tissue, or animal, is beneficial to the animal. That is, where a disease, disorder or condition in an animal is mediated by or associated with altered level of PCADM-1 expression or protein level, the composition can be used to modulate such expression or protein level of PCADM-1.

One skilled in the art would understand, based on the disclosure provided herein, that PCADM-1 can be administered to a cell or tissue by administering the protein itself or by administering a nucleic acid encoding the protein. Either way, PCADM-1 is administered to the cell and/or tissue.

For administration to the mammal, a polypeptide, or a nucleic acid encoding it, a ribozyme that specifically cleaves an mRNA encoding the polypeptide, and/or an antisense nucleic acid complementary to all or a portion of a nucleic acid encoding the protein, can be suspended in any pharmaceutically acceptable carrier, for example, HEPES buffered saline at a pH of about 7.8.

The skilled artisan would further appreciate, based upon the disclosure provided herein, that the invention encompasses compositions comprising at least one of a nucleic acid encoding PCADM-1, an isolated PCADM-1 polypeptide, an enzymatic nucleic acid (DNAZYM) that specifically cleaves mRNA transcribed from a nucleic acid encoding PCADM-1, and an antibody that specifically binds with PCADM-1, or a portion thereof.

The compositions encompassed in the invention also comprise those comprising various antibodies that specifically bind with various epitopes of the PCADM-1 polypeptide, and DNAZYMs that specifically bind with and cleave different regions of the PCADM-1 mRNA and/or overlapping regions of the mRNA encoding PCADM-1 mRNA.

One skilled in the art would understand, based upon the instant disclosure, that compositions comprising mixtures of the above-discussed compounds, i.e., DNAZYMs or DNA enzymes, ribozymes, antisense nucleic acids, antibodies, nucleic acids encoding PCADM-1, and PCADM-1 polypeptides, double-stranded oligonucleotides that specifically bind with PCADM-1 polypeptide, and the like, are encompassed in the invention.

Additionally, compositions comprising at least one of the afore-mentioned compounds where the compositions further comprise additional compounds, such as, but not limited to, small molecules, peptidomimetics, DNAZYMs or DNA enzymes, ribozymes and antisense nucleic acids specific for other proteins (e.g., VEGF-1 and MMP-2, and the like), drugs, chemotherapeutic agents, and the like, are also contemplated in the present invention. One skilled in the art would appreciate, based upon the disclosure provided herein, that such compositions are useful for diagnosis and treatment of diseases, disorders, or conditions associated with or mediated by altered expression of PCADM-1.

Other pharmaceutically acceptable carriers, which are useful include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides.

Pharmaceutical compositions that are useful in the methods of the invention may be administered, prepared, packaged, and/or sold in formulations suitable for oral, rectal, vaginal, peritoneal, topical, pulmonary, intranasal, buccal, ophthalmic, or another route of administration. Other contemplated formulations include projected nanoparticles, liposomal preparations, resealed erythrocytes containing the active ingredient, and immunologically-based formulations.

The compositions of the invention may be administered via numerous routes, including, but not limited to, oral, rectal, vaginal, parenteral, topical, pulmonary, intranasal, buccal, or ophthalmic administration routes. The route(s) of administration will be readily apparent to the skilled artisan and will depend upon any number of factors including the type and severity of the disease being treated, the type and age of the veterinary or human patient being treated, and the like.

Pharmaceutical compositions that are useful in the methods of the invention may be administered systemically in oral solid formulations, ophthalmic, suppository, aerosol, topical or other similar formulations. In addition to the compound such as heparan sulfate, or a biological equivalent thereof, such pharmaceutical compositions may contain pharmaceutically-acceptable carriers and other ingredients known to enhance and facilitate drug administration. Other possible formulations, such as nanoparticles, liposomes, resealed erythrocytes, and immunologically based systems may also be used to administer PCADM-1 and/or a nucleic acid encoding the same according to the methods of the invention.

Compounds, which are identified using any of the methods described herein may be formulated and administered to a mammal for treatment of prostate cancer are now described.

The invention encompasses the preparation and use of pharmaceutical compositions comprising a compound useful for treatment of prostate cancer as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "pharmaceutically acceptable carrier" means a chemical composition with which the active ingredient may be combined and which, following the combination, can be used to administer the active ingredient to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions, which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

Pharmaceutical compositions that are useful in the methods of the invention may be prepared, packaged, or sold in formulations suitable for oral, rectal, vaginal, parenteral, topical, pulmonary, intranasal, buccal, ophthalmic, intrathecal or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient, which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants and preservatives.

A pharmaceutical composition of the invention may be prepared, packaged, or sold in a formulation suitable for vaginal administration. Such a composition may be in the form of, for example, a suppository, an impregnated or coated vaginally-insertable material such as a tampon, a douche preparation, or gel or cream or a solution for vaginal irrigation.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

Douche preparations or solutions for vaginal irrigation may be made by combining the active ingredient with a pharmaceutically acceptable liquid carrier. As is well known in the art, douche preparations may be administered using, and may be packaged within, a delivery device adapted to the vaginal anatomy of the subject. Douche preparations may further comprise various additional ingredients including, but not limited to, antioxidants, antibiotics, antifungal agents, and preservatives.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations, which are useful, include those, which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken, i.e., by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1-1.0% (w/w) solution or suspension of the active ingredient in an aqueous or oily liquid carrier. Such drops may further comprise buffering agents, salts, or one or more other of the additional ingredients described herein. Other ophthalmically-administrable formulations, which are useful, include those, which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

Typically, dosages of the compound of the invention which may be administered to an animal, preferably a human, will vary depending upon any number of factors, including but not limited to, the type of animal and type of disease state being treated, the age of the animal and the route of administration.

The compound can be administered to an animal as frequently as several times daily, or it may be administered less frequently, such as once a day, once a week, once every two weeks, once a month, or even once a year or less. The frequency of the dose will be readily apparent to the skilled artisan and will depend upon any number of factors, such as, but not limited to, the type and severity of the disease being treated, the type and age of the animal, and the like.

VIII. Methods

A. Methods of Identifying Useful Compounds

The present invention further includes a method of identifying a compound that affects expression of PCADM-1 in a cell. The method comprises contacting a cell with a test compound and comparing the level of expression of PCADM-1 in the cell so contacted with the level of expression of PCADM-1 in an otherwise identical cell not contacted with the compound. If the level of expression of PCADM-1 is higher or lower in the cell contacted with the test compound compared to the level of expression of PCADM-1 in the otherwise identical cell not contacted with the test compound, this is an indication that the test compound affects expression of PCADM-1 in a cell.

Similarly, the present invention includes a method of identifying a compound that reduces expression of PCADM-1 in a cell. The method comprises contacting a cell with a test compound and comparing the level of expression of PCADM-1 in the cell contacted with the compound with the level of expression of PCADM-1 in an otherwise identical cell, which is not contacted with the compound. If the level of expression of PCADM-1 is lower in the cell contacted with the compound compared to the level in the cell that was not contacted with the compound, then that is an indication that the test compound affects reduces expression of PCADM-1 in a cell.

One skilled in the art would appreciate, based on the disclosure provided herein, that the level of expression of PCADM-1 in the cell may be measured by determining the level of expression of mRNA encoding PCADM-1. Alternatively, the level of expression of mRNA encoding PCADM-1 can be determined by using immunological methods to assess PCADM-1 production from such mRNA as exemplified herein using Western blot analysis, FACS analysis, or enzyme linked immunoassays using an anti-PCADM-1 antibody of the invention. Further, nucleic acid-based detection methods, such as Northern blot and PCR assays and the like, can be used as well. Thus, one skilled in the art would appreciate, based upon the extensive disclosure and reduction to practice provided herein, that there are a plethora of methods that are well-known in the art, which can be used to asses the level of expression of PCADM-1 in a cell including those disclosed herein and others which may be developed in the future.

Further, one skilled in the art would appreciate based on the disclosure provided herein that, as disclosed in the examples below, a cell which lacks endogenous PCADM-1 expression can be transfected with a vector comprising an isolated nucleic acid encoding PCADM-1 whereby expression of PCADM-1 is effected in the cell. The transfected cell is then contacted with the test compound thereby allowing the determination of whether the compound affects the expression of PCADM-1. Therefore, one skilled in the art armed with the present invention would be able to, by selectively transfecting a cell lacking detectable levels of PCADM-1 using PCADM-1-expressing vectors, identify a compound which selectively affects PCADM-1 expression.

One skilled in the art would understand, based upon the disclosure provided herein, that the invention encompasses any test compound identified using the methods discussed elsewhere herein. That is, a compound that inhibits PCADM-1 expression can be used to develop therapeutics and diagnostics for diseases, disorders or conditions mediated by PCADM-1 over-expression such as prostate cancer. That is, one skilled in the art would appreciate, as more fully set forth elsewhere herein in discussing DNAZYMs or ribozymes, or anti sense that specifically cleave PCADM-1, that decreasing the level of PCADM-1 expression associated with a disease, disorder or condition is a potential therapeutic for treatment of the disease, disorder or condition. Thus, a compound identified by the methods disclosed herein is a potential therapeutic for treatment of prostate cancer, among other things.

One skilled in the art would understand, based upon the disclosure provided herein, that the invention encompasses methods of identifying a compound that increases the level of PCADM-1 in a cell. These methods are useful in that the data disclosed herein demonstrate, for the first time, that increased expression of PCADM-1 is associated with and/or mediates prostate cancer. Thus, a compound that increases the level of PCADM-1 is a potential prostate carcinogen and the identification of such compounds is important in assessing the potential toxicity of a compound and is thus a useful assay, for example, in the field of drug development where the identification of potential deleterious effects associated with a novel compound is of utmost importance. Therefore, the present invention provides useful assays for identification of potential negative effect in the field of drug development, and the like.

The skilled artisan would further appreciate, based upon the disclosure provided herein, that the present invention includes a method of identifying a compound that inhibits binding of PCADM-1 with a double-stranded nucleic acid that specifically binds with PCADM-1. The method comprises assessing the level of PCADM-1 binding with a double-stranded nucleic acid known to specifically bind with PCADM-1. Such double-stranded nucleic acids include, but are not limited to, a nucleic acid having the sequence SEQ ID NO:5, sequence SEQ ID NO:6, SEQ ID NO:7 and SEQ ID NO:8. That is, by assessing and comparing the level of PCADM-1 binding with a double-stranded nucleic acid that specifically binds with PCADM-1 in the presence and absence of a compound, a compound can be identified where the level of binding of PCADM-1 with the nucleic acid is lower in the presence of the compound compared with the level in the absence of the compound. Thus, a compound that inhibits PCADM-1 binding with a nucleic acid that specifically binds with PCADM-1 can be identified and such assays are encompassed in the present invention. These compounds may be useful therapeutics since the specific binding interaction between PCADM-1 and a nucleic acid that specifically binds therewith can be a potential target for treatment of a disease, disorder or disease associated with or mediated by such binding interaction, e.g., prostate cancer, and the like.

B. Methods of Treating or Alleviating a Disease, Disorder or Condition Associated with or Mediated by PCADM-1 Expression The invention includes a method of alleviating a disease, disorder or condition mediated by mal-expression of PCADM-1. The method comprises administering an expression modulating compound, e.g., a DNAZYM, an antisense nucleic acid or ribozyme complementary to a nucleic acid encoding PCADM-1, to a patient afflicted with a disease, disorder or condition mediated by increased PCADM-1 expression compared to the level of PCADM-1 expression in otherwise identical but normal tissue, i.e., tissue which does not exhibit any detectable clinical parameters associated with the disease, disorder or condition being treated or alleviated. This, in turn, mediates a decrease in PCADM-1 expression thereby alleviating a disease, disorder or condition mediated by mal-expression of PCADM-1. Such diseases, disorder or conditions include, but are not limited to, prostate cancer PCADM-1 DNAZYMs, or antisense nucleic acids or ribozymes that inhibit expression of PCADM-1 can therefore also be used for the manufacture of a medicament for treatment of a disease, disorder or condition mediated by increased expression of PCADM-1 when compared with expression of PCADM-1 in a cell and/or a patient not afflicted with the disease, disorder or condition.

Additionally, the invention includes a method of inhibiting expression of prostate cancer antigen diagnostic marker 1 in a cell. This method is extremely useful in that as demonstrated by the data disclosed elsewhere herein, inhibition of expression of PCADM-1 inhibited the growth and/or survival of cancer cells (e.g., prostate tumor cells) but not normal, non-tumor cells. Thus, the skilled artisan would appreciated, based on the disclosure provided herein, that the invention encompasses a method of inhibiting expression of PCADM-1, which includes, but is not limited to, using DNAZYMs to cleave PCADM-1 mRNA in a cell thereby inhibiting expression of PCADM-1 in that cell. However, the invention is not limited to inhibiting expression of PCADM-1 using solely DNA enzymes; rather, the invention encompasses methods of inhibiting transcription or translation of a protein, i.e., PCADM-1, using methods known in the art or to be developed in the future.

More particularly, the method comprises administering to a cell an isolated enzymatic nucleic acid which specifically cleaves mRNA transcribed from a nucleic acid encoding said prostate cancer antigen diagnostic marker 1, thereby inhibiting expression of said prostate cancer antigen diagnostic marker 1 in said cell.

In one aspect, the isolated enzymatic nucleic acid is selected from the group consisting of an enzymatic nucleic acid having the sequence of SEQ ID NO:9 and an enzymatic nucleic acid having the sequence of SEQ ID NO:10. However, based upon the teachings provided herein, the skilled artisan would understand the invention encompasses using other DNAZYMs based upon the sequence of PCADM-1 (SEQ ID NO:1), and/or using other methods to inhibit expression of PCADM-1 in a cell, such methods being well-known in the art (e.g., use of antisense molecules, antibodies, and the like). Therefore, the invention is not limited to using PCADM-1 DNAZYM-1 (SEQ ID NO:9) or PCADM-1 DNAZYM-1 (SEQ ID NO:10), but includes methods well-known in the art for inhibiting expression of a nucleic acid where the sequence of the nucleic acid is known, including using other DNAZYMs based upon the sequence of PCADM-1 (SEQ ID NO:1).

One skilled in the art would understand, based upon the disclosure provided herein, that because reducing expression of PCADM-1 can mediate a beneficial effect in a patient afflicted with prostate cancer (as demonstrated by the selective inhibition of prostate cancer cells, but not normal cells, mediated by administering PCADM-1 DNAZYMs to the cells), decreased PCADM-1 expression can be useful for treating such diseases, disorders, or conditions. This is because, as disclosed elsewhere herein, increased expression of PCADM-1 is associated with abnormal cell proliferation and/or cell survival and/or net tumor growth associated with prostate cancer. Further, the data disclosed elsewhere herein demonstrate that inhibition of PCADM-1 expression, such as by administered by a PCADM-1 DNAZYM that specifically cleaved PCADM-1 mRNA, effected a beneficial decrease in tumors and increased the survival time in an art-recognized mouse model for study of prostate cancer therapeutics. Thus, one skilled in the art would appreciate, based upon the disclosure provided herein, that inhibition of PCADM-1 expression can inhibit the deleterious effects of PCADM-1 mal-expression.

One skilled in the art would understand, based upon the disclosure provided herein, that since reduced PCADM-1 expression can mediate a beneficial effect, methods of decreasing expression of PCADM-1 mRNA, decreasing the level of PCADM-1 polypeptide present in the cell, and/or decreasing the activity of PCADM-1 in a cell (using, e.g., DNAZYMs, antisense nucleic acids, ribozymes, antibodies, and the like), can be used to treat and/or alleviate a disease, disorder or condition associated with altered expression of PCADM-1 where a lower level of PCADM-1 would provide a benefit. Thus, whether a DNAZYM, antisense nucleic acid, a ribozyme or a blocking antibody is administered, the crucial feature of the present invention is that the expression of PCADM-1 be reduced in a cell.

Techniques for inhibiting expression of a nucleic acid in a cell are well known in the art and encompass such methods as disclosed herein (e.g., inhibition using an antibody, a DNAZYM, antisense nucleic acid, a ribozyme and the like). Other techniques useful for inhibiting expression of a nucleic acid encoding PCADM-1 include, but are not limited to, using nucleotide reagents that target specific sequences of the PCADM-1 promoter, and the like.

One skilled in the art would understand, based upon the disclosure provided herein, that it may be useful to increase the level or activity of PCADM-1 in a cell. That is, it can be useful to treat or alleviate a disease, disorder of condition associated with or mediated by decreased expression, level, or activity of PCADM-1 by administering PCADM-1. Such diseases, disorders or conditions include, but are not limited to prostate cancer, and possibly other solid cancers or leukemias, AIDS, HIV infection, immune disorders and inflammatory or degenerative disorders, and the like.

Whether expression of PCADM-1, levels of the polypeptide, or its activity, is increased or decreased, one skilled in the art would appreciate, based on this disclosure, that methods of reducing or inducing PCADM-1 of the invention encompass administering a recombinant cell that either expresses or lacks expression of PCADM-1.

In another embodiment of the invention, an individual suffering from a disease, disorder or a condition that is associated with or mediated by altered PCADM-1 expression can be treated by supplementing, augmenting and/or replacing defective cells with cells that lack PCADM-1 expression. The cells can be derived from cells obtained from a normal syngeneic matched donor or cells obtained from the individual to be treated. The cells may be genetically modified to inhibit PCADM-1 expression.

An example of a disease, disorder or a condition associated with or mediated by PCADM-1 expression is prostate cancer, and the like. In addition to replacing defective cells with repaired cells or normal cells from matched donors, the method of the invention may also be used to facilitate expression of a desired protein that when secreted in the an animal, has a beneficial effect. That is, cells may be isolated, furnished with a gene encoding PCADM-1 and introduced into the donor or into a syngeneic matched recipient. Expression of the PCADM-1 exerts a therapeutic effect. This aspect of the invention relates to gene therapy in which therapeutic amounts of PCADM-1 are administered to an individual.

In particular, a gene construct that comprises a heterologous gene, which encodes PCADM-1 is introduced into cells. These recombinant cells are used to purify isolated PCADM-1, which was then administered to an animal. One skilled in the art would understand, based upon the disclosure provided herein, that instead of administering an isolated PCADM-1 polypeptide, PCADM-1 can be administered to a mammal in need thereof by administering to the mammal the recombinant cells themselves. This will benefit the recipient individual who will benefit when the protein is expressed and secreted by the recombinant cell into the recipient's system.

According to the present invention, gene constructs comprising nucleotide sequences of the invention are introduced into cells. That is, the cells, referred to herein as "recombinant cells," are genetically altered to introduce a nucleic acid encoding PCADM-1 or a nucleic acid that inhibits PCADM-1 expression in and/or secretion by the recombinant cell (e.g., an antisense nucleic acid, an enzymatic nucleic acid that specifically cleaves RNA transcribed from a nucleic acid encoding a PCADM-1) thereby mediating a beneficial effect on an recipient to which the recombinant cell is administered. According to some aspects of the invention, cells obtained from the same individual to be treated or from another individual, or from a non-human animal, can be genetically altered to replace a defective gene and/or to introduce a nucleic acid whose expression has a beneficial effect on the individual or to inhibit PCADM-1 expression which inhibition can have a beneficial effect on the individual.

In some aspects of the invention, an individual suffering from a disease, disorder or a condition can be treated by supplementing, augmenting and/or replacing defective or deficient nucleic acid encoding PCADM-1 by providing an isolated recombinant cells containing gene constructs that include normal, functioning copies of a nucleic acid encoding PCADM-1. This aspect of the invention relates to gene therapy in which the individual is provided with a nucleic encoding PCADM-1 for which they are deficient in presence and/or function. The isolated nucleic acid encoding PCADM-1 provided by the cell compensates for the defective PCADM-1 expression of the individual, because, when the nucleic acid is expressed in the individual, a protein is produced which serves to alleviate or otherwise treat the disease, disorder or condition in the individual. Such nucleic acid preferably encodes a PCADM-1 polypeptide that is secreted from the recombinant cell.

In all cases in which a gene construct encoding PCADM-1 is transfected into a cell, the nucleic acid is operably linked to an appropriate promoter/regulatory sequence, which is required to achieve expression of the nucleic acid in the recombinant cell. Such promoter/regulatory sequences include but are not limited to, constitutive and inducible and/or tissue specific and differentiation specific promoters, and are discussed elsewhere herein. Constitutive promoters include, but are not limited to, the cytomegalovirus immediate early promoter and the Rous sarcoma virus promoter. In addition, housekeeping promoters such as those, which regulate expression of housekeeping genes may also be used. Other promoters include those, which are preferentially expressed in cells of the central nervous system, such as, but not limited the promoter for the gene encoding glial fibrillary acidic protein. In addition, promoter/regulatory elements may be selected such that gene expression is inducible. For example, a tetracycline inducible promoter may be used (Freundlich et al., 1997, Meth. Enzymol. 283: 159-173).

The gene construct is preferably provided as an expression vector, which, includes the coding sequence of a mammalian PCADM-1 of the invention operably linked to essential promoter/regulatory sequences such that when the vector is transfected into the cell, the coding sequence is expressed by the cell. The coding sequence is operably linked to the promoter/regulatory elements necessary for expression of the sequence in the cells. The nucleotide sequence that encodes the protein may be cDNA, genomic DNA, synthesized DNA or a hybrid thereof or an RNA molecule such as mRNA.

The gene construct, which includes the nucleotide sequence encoding PCADM-1 operably linked to the promoter/regulatory elements, may remain present in the cell as a functioning episomal molecule or it may integrate into the chromosomal DNA of the cell. Genetic material may be introduced into cells where it remains as separate genetic material in the form of a plasmid. Alternatively, linear DNA, which can integrate into a host cell chromosome may be introduced into the cell. When introducing DNA into the cell, reagents, which promote DNA integration into chromosomes may be added. DNA sequences, which are useful to promote integration may also be included in the DNA molecule. Alternatively, RNA may be introduced into the cell.

In order for genetic material in an expression vector to be expressed, the promoter/regulatory elements must be operably linked to the nucleotide sequence that encodes the protein. In order to maximize protein production, promoter/regulatory sequences may be selected which are well suited for gene expression in the desired cells. Moreover, codons may be selected which are most efficiently transcribed in the cell. One having ordinary skill in the art can produce recombinant genetic material as expression vectors which are functional in the desired cells.

It is also contemplated that promoter/regulatory elements may be selected to facilitate tissue specific expression of the protein. Thus, for example, specific promoter/regulatory sequences may be provided such that the heterologous gene will only be expressed in the tissue where the recombinant cells are implanted. One skilled in the art would understand, based upon the disclosure provided herein, that the preferred tissues where the expression or lack of expression of PCADM-1 is to be targeted include, but are not limited to, prostate tissue. In addition, promoter/regulatory elements may be selected such that gene expression is inducible. For example, a tetracycline inducible promoter may be used (Freundlich et al., 1997, Meth. Enzymol. 283: 159-173).

In addition to providing cells with recombinant genetic material that either corrects a genetic defect in the cells, that encodes a protein which is otherwise not present in sufficient quantities and/or functional condition so that the genetic material corrects a genetic defect in the individual, and/or that encodes a protein which is useful as beneficial in the treatment or prevention of a particular disease, disorder or condition associated therewith, and that inhibits expression of PCADM-1 in the cell (e.g., a knock-out targeting gene, a DNAZYM, a antisense nucleic acid, a ribozyme, and the like), genetic material can also be introduced into the recombinant cells used in the present invention to provide a means for selectively terminating such cells should such termination become desirable. Such means for targeting recombinant cells for destruction may be introduced into recombinant cells.

According to the invention, recombinant cells can be furnished with genetic material, which, renders them specifically susceptible to destruction. For example, recombinant cells may be provided with a gene that encodes a receptor that can be specifically targeted with a cytotoxic agent. An expressible form of a gene that can be used to induce selective cell death can be introduced into the recombinant cells. In such a system, cells expressing the protein encoded by the gene are susceptible to targeted killing under specific conditions or in, the presence or absence of specific agents. For example, an expressible form of a herpes virus thymidine kinase (herpes tk) gene can be introduced into the recombinant cells and used to induce selective cell death. When the introduced genetic material that includes the herpes tk gene is introduced into the individual, herpes tk will be produced. If it is desirable or necessary to kill the implanted recombinant cells, the drug gancyclovir can be administered to the individual, which will cause the selective killing of any cell producing herpes tk. Thus, a system can be provided which allows for the selective destruction of implanted recombinant cells.

One skilled in the art would understand, based upon the disclosure provided herein, that the present invention encompasses production of recombinant cells to either provide PCADM-1 to or inhibit PCADM-1 expression in a mammal. That is, the cells can be used to administer PCADM-1 to an animal or to deliver a molecule (e.g., a knock-out targeting gene, a DNAZYM, a antisense nucleic acid, a ribozyme [e.g., an isolated enzymatic nucleic acid having the sequence of SEQ ID NO:9, SEQ ID NO:10 and antibody that specifically binds with PCADM-1, and the like).

Administration of PCADM-1 to an animal can be used as a model system to study the mechanism of action of PCADM-1, e.g., for assessing the effect(s) of inhibiting PCADM-1/DNA binding interactions, and to develop model systems useful for the development of diagnostics and/or therapeutics for diseases, disorders or conditions associated with PCADM-1 expression.

Further, the delivery of PCADM-1 to an animal mediated by administration of recombinant cells expressing and secreting PCADM-1 can also be used to treat or alleviate a disease, disorder or condition where increasing the level of PCADM-1 mediates a therapeutic effect. More specifically, administration of PCADM-1 to an animal by administering a recombinant cell expressing a nucleic acid encoding PCADM-1 can be useful for treatment of prostate cancer (i.e., in dogs and humans) prostate cancer, and possibly other solid cancers or leukemias, AIDS, HIV infection, immune disorders, and inflammatory or degenerative disorders which afflict humans and animals alike, among other things.

Alternatively, administration of recombinant cells comprising a nucleic acid the expression of which inhibits or reduces PCADM-1 expression, activity, and/or PCADM-1 binding with DNA, can be used as a model for the development of diagnostics and/or therapeutics useful for diseases, disorders or conditions associated with or mediated by PCADM-1 expression, activity, and/or protein/nucleic acid binding interactions. The present invention encompasses that the recombinant cells can produce the molecule that inhibits PCADM-1 expression thereby providing such molecule to the animal. Alternatively, without wishing to be bound by any particular theory, the recombinant cells themselves, which are otherwise functional cells, except for the inability to express PCADM-1, can perform the functions of otherwise identical but non-recombinant cells, without being subject to the PCADM-1 signaling pathway.

Cells, whether obtained from an animal, from established cell lines that are commercially available or to be developed, or primary cells cultured in vitro, can be transfected using well known techniques readily available to those having ordinary skill in the art. Thus, the present invention is not limited to obtaining cells from a donor animal or from the patient animal itself. Rather, the invention includes using any cell that can be engineered using a nucleic acid of the invention such that the recombinant cell expresses PCADM-1, a PCADM-1 DNAZYM, and/or antibody that specifically binds with PCADM-1 (where it did not express such molecule prior to being engineered, or where the cell produced the molecule an a different level prior to the introduction of the nucleic acid into the cell) or the recombinant cell does not express PCADM-1, PCADM-1 DNAZYMs, and/or antibody that specifically binds with PCADM-1 or expresses it at a lower level (where it expressed the molecule before or expressed it a different level prior to introduction of the nucleic acid into the cell).

Nucleic acids can be introduced into the cells using standard methods which are employed for introducing a gene construct into cells which express the protein encoded by the gene or which express a molecule that inhibits PCADM-1 expression (Sambrook et al.). In some embodiments, cells are transfected by calcium phosphate precipitation transfection, DEAE dextran transfection, electroporation, microinjection, liposome-mediated transfer, chemical-mediated transfer, ligand mediated transfer or recombinant viral vector transfer.

In some embodiments, recombinant adenovirus vectors are used to introduce DNA having a desired sequence into the cell. In some embodiments, recombinant retrovirus vectors are used to introduce DNA having a desired sequence into the cell. In some embodiments, standard calcium phosphate, DEAE dextran or lipid carrier mediated transfection techniques are employed to incorporate a desired DNA into dividing cells. Standard antibiotic resistance selection techniques can be used to identify and select transfected cells. In some embodiments, DNA is introduced directly into cells by microinjection. Similarly, well known electroporation or particle bombardment techniques can be used to introduce foreign DNA into cells. A second gene is usually co-transfected with and/or covalently linked to the nucleic acid encoding PCADM-1, or knock-out targeting vectors, thereto. The second gene is frequently a selectable antibiotic-resistance gene. Transfected recombinant cells can be selected by growing the cells in an antibiotic that kills cells that do not take up the selectable gene. In most cases where the two genes are unlinked and co-transfected, the cells that survive the antibiotic treatment contain and express both genes.

Where an isolated PCADM-1 DNAZYM, PCADM-1 polypeptide, an antibody that specifically binds with PCADM-1, and/or recombinant cells of the invention are administered to an animal either to increase or reduce the level of PCADM-1 present in the animal, one skilled in the art would understand, based upon the disclosure provided herein, that the amount of the polypeptide, nucleic acid, antibody, or cell to be administered to the animal can be titrated by assessing the level of PCADM-1 and/or sugar present in the blood/urine/other fluids or by determining the level of expression of PCADM-1 mRNA or the level of PCADM-1 polypeptide or nucleic acid encoding PCADM-1 present in the tissues of the animal.

Further, the skilled artisan would understand, based upon the disclosure provided herein, that a mixture of any compound that inhibits the effect of PCADM-1 (e.g., a PCADM-1 DNAZYM, an antibody, a double-stranded nucleic acid that specifically binds with PCADM-1 thereby disrupting PCADM-1/DNA binding necessary for PCADM-1 activity) can also be used to alleviate and/or treat a disease, disorder or condition associated with or mediated by altered PCADM-1 expression. Further, one or more such compounds can be combined with other compounds useful to treat diseases, disorders or conditions such as prostate cancer. That is, the invention encompasses administration of, PCADM-1 DNAZYM, anti-PCADM-1 antibody, and double-stranded nucleic acid that specifically binds with PCADM-1 either alone or in combination with each other and with substances including, but not limited to, DNAZYMs, or directed to other proteins (e.g., VEGF-1, MMP-2, and the like), peptidomimetics, small molecules, and drugs (e.g., chemotherapeutic agents), and various permutations thereof as the skilled artisan would determine using methods well-known in the art and methods that are developed in the future with respect to administration of such molecules.

Methods for assessing the level of PCADM-1 (e.g., using anti-PCADM-1 antibodies in Western blot or other immune-based analyses such as, FACS analysis, or enzyme linked immunosorbent assay); methods for assessing the level of PCADM-1 expression in a cell and/or tissues (e.g., using Northern blot analysis, and the like); and/or methods such as "Monte Carlo-like" DNA/protein binding assays based on detection of binding of a duplex nucleic acid, (e.g., PCADM-1 probe 1 (SEQ ID NO:5) and PCADM-1 probe 2 (SEQ ID NO:6)), with PCADM-1 (e.g., using nylon membrane-based detection of labeled duplex nucleic acid and/or electrophoresis mobility shift assays (EMSAs) to assess binding of PCADM-1/DNA), are disclosed herein or are well known to those skilled in the art. Such assays can be used to determine the "effective amount or activity" of PCADM-1, nucleic acid, antibody, PCADM-1 DNAZYMs, antisense nucleic acid, ribozyme, recombinant cell, and the like, to be administered to the animal in order to reduce or increase the level of PCADM-1 to a desired level.

C. Methods of Diagnosis and Assessment of Therapies

The present invention includes methods of diagnosis of certain diseases, disorders, or conditions (e.g., prostate cancer) which are associated with or mediated by altered and/or mal-expression of PCADM-1.

The invention includes a method of diagnosing a prostate tumor in a previously undiagnosed mammal. The method comprises obtaining a biological sample from the mammal and comparing the level of PCADM-1 (expression, amount, activity) in the sample with the level of PCADM-1 in a sample from an otherwise identical normal mammal that is not afflicted with a prostate tumor. A higher level of PCADM-1 in the sample from the mammal in question compared with the level of PCADM-1 in the sample obtained from a mammal known not to be afflicted with prostate tumor is an indication that the mammal is afflicted with a prostate tumor. This is because, as disclosed elsewhere herein, an increased level of PCADM-1 expression and/or activity is associated with the presence of prostate cancer. Thus, detection of increased level of PCADM-1 protein, nucleic acid encoding PCADM-1, and/or increased level of PCADM-1 binding with a double-stranded nucleic acid that specifically binds with PCADM-1, in a sample obtained from mammal is an indication that the mammal is afflicted with prostate cancer.

Further, the data disclosed elsewhere herein also demonstrate that there is a correlation between the level of PCADM-1 in the sample and the Gleason Score of the various tumor tissues indicating that the level of PCADM-1 is a staging marker for such tumors. Thus, detection of an altered level of expression of PCADM-1 (whether detected using antibody-based methods or methods based on detection of nucleic acids), or detection of increased PCADM-1 binding of a nucleic acid that specifically binds with PCADM-1 (e.g., such as a nucleic acid having the sequence of SEQ ID NO:5, SEQ ID NO:6, SEQ ID NO:7, and SEQ ID NO:8), is indicative of the stage of a prostate tumor since the data disclosed herewith demonstrates that the level of expression of PCADM-1 is correlated with the Gleason Score of the tumor. Thus, the present invention includes methods of assessing the state, i.e., "staging," a prostate tumor by assessing the level of PCADM-1 in a sample obtained from a mammal compared with the level of PCADM-1 detecting in a sample obtained from an otherwise normal mammal known not to have a prostate cancer tumor or known to have a prostate cancer tumor of a known specific stage and/or having a known Gleason Score.

In one aspect, the biological sample is selected from the group consisting of a blood sample, a prostate biopsy, a urine sample, a prostatic fluid sample, a semen sample, a lymph fluid sample, a seminal vesicle tissue sample, a pleural cavity fluid sample, a perineal cavity fluid sample, a peritoneal cavity fluid sample, a bone marrow sample, a salivary gland fluid sample, and prostate cancer tumor sample, and a sample obtained from other cancer tissues, and the like.

One skilled in the art would understand, based upon the disclosure provided herein, that there are a wide variety of methods for assessing the level of PCADM-1 in a sample. Such methods include, but are not limited to, antibody-based detection methods (e.g., using anti-PCADM-1 or other cross-reactive antibodies in Western blot or other immune-based analyses such as ELISA, FACS assay, and enzyme linked immuno-sandwich assay); methods for assessing the level of PCADM-1 expression in a cell and/or tissues (e.g., using Northern blot analysis, and the like), and/or methods such as "Monte Carlo-like" DNA/protein binding assays based on detection of binding of a duplex nucleic acid, e.g., PCADM-1 probe 1 (SEQ ID NO:5) and PCADM-1 probe 2 (SEQ ID NO:6), with PCADM-1 polypeptide (e.g., using nylon membrane-based detection of double-stranded nucleic acid and/or EMSAs to assess binding of PCADM-1 with a double-stranded nucleic acid that specifically binds with PCADM-1). Thus, methods of detecting PCADM-1, either by detecting a PCADM-1 polypeptide or a nucleic acid encoding PCADM-1 (i.e., RNA or DNA), or a nucleic acid that specifically binds with PCADM-1 polypeptide, are disclosed herein or are well known to those skilled in the art and are encompassed in the present invention. Furthermore, the present invention encompasses similar assays for the detection of a specific protein or nucleic acid in a sample as may be developed in the future.

The invention includes a method of assessing the effectiveness of a treatment for a prostate cancer in a mammal. The method comprises assessing the level of PCADM-1 expression, amount, and/or DNA binding activity, before, during and after a specified course of treatment for a disease, disorder or condition mediated by or associated with increased PCADM-1 expression (e.g., prostate cancer). This is because, as stated previously elsewhere herein, PCADM-1 expression, amount and/or activity is associated with or mediates certain disease states. Thus, assessing the effect of a course of treatment upon PCADM-1 expression/amount/DNA-binding activity indicates the efficacy of the treatment such that a lower level of PCADM-1 expression, amount, or activity indicates that the treatment method is successful.

D. Methods of Identifying DNA-Binding Proteins and their Cognate Double-Stranded Oligonucleotide Binding Partners The present invention includes methods of identifying DNA-binding proteins and double-stranded oligonucleotides bound by the proteins. The methods comprise contacting a member of a set of semi-random double-stranded oligonucleotides with a mixture containing DNA-binding proteins. The oligonucleotides are semi-random in that they comprise an unknown random sequence, which is flanked on both 5' and 3' sides, but at least two known base pairs. In one embodiment, the oligonucleotide was 8 bp in length where the first base pair was an A then the second base pair was varied with each A, T, G, C, while the flanking known pair was the complementary Watson-Crick base pairing match so that where the nucleotide at position 1 was an "A" the nucleotide at position 8 was "T." Similarly, when the second position was A, the seventh nucleotide was T, and so forth. Thus, a set of semi-random oligonucleotides is generated such that the 2 base pairs at the 5' end and the 2 base pairs at the 3' end are known and there is in between them an unknown core sequence of about 4 base pairs.

The skilled artisan would appreciate, based upon the disclosure provided herein that the known flanking base pairs are not limited to 2. Further, one skilled in the art would understand that the unknown, random, core sequence can range from about 3 to 12 base pairs, such that the double-stranded oligonucleotide preferably ranges in size from about 7 to 16 base pairs, i.e., a 5' end comprising 2 known base pairs followed by 3 to 12 unknown core base pairs, which are in turn followed by 2 known base pairs that are a mirror image of the first 2 known base pairs at the 3' end of the oligomer, where the 2 nucleotides at the 5' end of the molecule would be able to bond with the 2 nucleotides at the 3' end of the molecule according to Watson-Crick base pairing rules such that the first two nucleotides of the oligonucleotide and the last two nucleotides would hybridize with each other if the oligonucleotide was single-stranded and could, but need not, form a short stem and loop structure.

Each semi-random oligonucleotide from the set is then mixed with a mixture comprising DNA-binding proteins. The oligonucleotides and proteins are allowed to incubate under conditions where specific DNA-protein binding can occur. Such conditions are well-known in the art and are exemplified herein and the present invention is not limited to any particular set of reaction conditions. Rather, the present invention includes a wide plethora of reaction conditions well known in the art, disclosed herein, and to be developed in the future, which the skilled artisan, armed with the teaching of the present invention, would understand could be used to asses the specific binding of a double-stranded nucleic acid with PCADM-1.

The double-stranded oligonucleotide demonstrating the highest binding affinity to DNA-binding proteins is then selected for use in the design of the next probe. More specifically, as depicted in Table 1, the 8 base pair oligonucleotide demonstrating the highest level of binding with a DNA-binding protein mixture (*CANNNNTG) was selected and a semi-random set of oligonucleotides having this sequence but having an additional known base pair such that the core random sequence was reduced by one base pair to only 3 unknowns (i.e., CACNNNTG, CAGNNNTG, CATNNNTG, and CAANNNTG) was produced. Once again, each member of the set was allowed to bind with a sample comprising DNA-binding proteins and the double-stranded oligonucleotide binding with the highest affinity with the proteins was identified and sequences (i.e., indicated by an asterisk and in bold—CACNNNTG). This procedure was repeated each time adding a known base pair and decreasing the number of unknown, random core sequence base pairs until the entire sequence of the double-stranded nucleic acid that binds with a DNA-binding protein is identified.

Further, one skilled in the art would appreciate, based upon the disclosure provided herein, that the protein that the double stranded oligonucleotide specifically binds with is also identified using this assay. Indeed, the "Monte Carlo-like" assay of the present invention identified the novel DNA-binding protein PCADM-1, and the novel nucleic acid sequence that binds with the protein (e.g., a nucleic acid having the sequence SEQ ID NO:5 and a nucleic acid having the sequence SEQ ID NO:6). Therefore, the invention encompasses methods of identifying DNA-binding proteins and proteins identified using such methods, including, but not limited to, proteins that are present at a higher level in tumor tissue than in otherwise identical, non-tumor tissue.

The skilled artisan would also appreciate, based upon the disclosure provided herein, that double-stranded oligonucleotides ranging in length from about 7 to 9 base pairs are used because, as more fully set forth elsewhere herein, these are the average lengths of many known DNA sequences that specifically bind with proteins, such as transcription factor proteins involved in the regulation of gene expression (Sambrook et al., 1989, supra). Therefore, these lengths were selected for use in the methods of the present invention. However, the present invention is not limited to these lengths; rather, the invention includes a central, unknown sequence ranging from about 3 to 12 base pairs, flanked by at least 2 known base pair such that the double-stranded oligonucleotide of the invention ranges from about 7 to 16 base pairs in length.

The method further comprises detecting specific DNA-protein binding. The skilled artisan, armed with the teachings set forth herein, would understand that specific DNA-protein binding can be detected using techniques well-known in the art such as those, but not limited to, the techniques exemplified herein, including applying the proteins to a solid support such as a nylon membrane and detecting labeled oligonucleotides that are specifically bound to the membrane to identify the protein that specifically binds with a double-stranded oligonucleotide.

Alternatively, detection of DNA-protein complexes can be performed using electrophoretic mobility shift assays, or EMSAs such as those disclosed herein and/or those known in the art. The protein can be excised from the gel and sequenced to determine the amino acid of the protein that specifically binds a double-stranded oligonucleotide. One skilled in the art, based upon the disclosure provided herein, would understand that the specific detection method for assessing the presence of DNA-protein binding, and for determining the identity (e.g., the amino acid sequence) of the protein, is not crucial and that there are many methods that can be used to detect DNA-protein complexes and to isolate and identify the DNA-binding protein and the double-stranded oligonucleotide bound therewith. Thus, using the methods of the invention, both DNA-binding proteins and the cognate double-stranded oligonucleotides that they bind with can be easily identified and characterized.

The invention also includes a method of identifying DNA-binding proteins and the double-stranded oligonucleotide sequences that they specifically bind with which are associated with a disease, disorder or condition, e.g., prostate cancer. The method comprises identifying DNA-binding proteins and their cognate oligonucleotide binding partners that are present in protein extracts prepared from diseased cells or tissue but which are not detected in protein extracts prepared from otherwise identical protein extracts prepared from normal cells and tissues known not to have a disease, disorder or condition. Thus, as would be appreciated by the skilled artisan based upon the disclosure provided herein, the methods of the present invention comprise identifying DNA-binding proteins and the oligonucleotides that they bind and to select those DNA-binding proteins and oligonucleotide binding partners that can be detected in protein extracts from diseased tissue but which are not detected, either because the DNA-binding protein is not present, possesses different properties, or is present in an amount beyond the limit of detection of the assay.

Identification of novel DNA-binding proteins the level of which is elevated in diseased but not in normal, non-diseased tissue is important in that such proteins, and their cognate double-stranded oligonucleotides, are potential diagnostic and therapeutic candidates for the diagnosis and treatment of such diseases, disorders or conditions. That is, such DNA-binding proteins are likely to be involved in or be associated with the disease process in that they may regulate cellular processes such as altered expression of certain genes, that are involved in tumorgenesis.

Indeed, PCADM-1, a novel DNA-binding protein identified using the methods disclosed herein, is involved or, at the very least, is associated with prostate cancer such that detection of PCADM-1 in tissue cells and bodily fluids is an effective means for the diagnosis of prostate cancer. In addition, inhibition of PCADM-1 expression in tumor cells (PC-3 ML) and tumor tissues (in SCID mice) decreased the survival of the tumor cells and the survival of the tumors. These results, which are not limited to PCADM-1, demonstrate the importance of identifying DNA-binding proteins, and the DNA that the specifically bind with, associated with a disease, disorder or condition since they are important for the development of diagnostics and therapeutics to treat these diseases, disorders or conditions.

IX. Kits

The invention includes various kits which comprise a compound, such as a nucleic acid encoding PCADM-1, an antibody that specifically binds PCADM-1, a PCADM-1 DNAZYM (i.e. DNAZYM) complementary, in part, to a nucleic acid encoding PCADM-1 that specifically cleaves PCADM-1 mRNA (e.g., a nucleic acid having sequence SEQ ID NO:9 (PCADM-1 DNAZYM-1), and SEQ ID NO:10, and the like) and/or compositions of the invention, a nucleic acid that specifically binds with a PCADM-1 polypeptide (e.g., PCADM-1 probe 1 [SEQ ID NO:5] and PCADM-1 probe 2 [SEQ ID NO:6]), an applicator, and instructional materials which describe use of the compound to perform the methods of the invention. Although exemplary kits are described below, the contents of other useful kits will be apparent to the skilled artisan in light of the present disclosure. Each of these kits is included within the invention.

In one aspect, the invention includes a kit for alleviating a disease mediated by mal-expression of PCADM-1. The kit is used pursuant to the methods disclosed in the invention. Briefly, the kit may be used to contact a cell with an antibody that specifically binds with PCADM-1, or with a DNAZYM that specifically cleaves PCADM-1 mRNA, wherein the decreased expression, amount, or activity of PCADM-1 mediates a beneficial effect. Moreover, the kit comprises an applicator and an instructional material for the use of the kit. These instructions simply embody the examples provided herein.

The kit includes a pharmaceutically-acceptable carrier. The composition is provided in an appropriate amount as set forth elsewhere herein. Further, the route of administration and the frequency of administration are as previously set forth elsewhere herein.

The invention further includes a kit for assessing the effectiveness of an anticancer treatment. The kit comprises a compound that specifically binds with PCADM-1, or a nucleic acid encoding PCADM-1, such that the level of PCADM-1 present in a sample can be assessed. As previously disclosed elsewhere herein, such PCADM-1 detecting compound includes, but is not limited to, an antibody that specifically binds with PCADM-1 (to be used in antibody based detection methods such as, for example, Western blot analysis, enzyme linked immuno-sandwich assay, FACS assay, or ELISA, enzyme immunoassay or EIA, and the like), a nucleic acid that specifically binds with a nucleic acid encoding PCADM-1 (for use in, e.g., Northern and Southern blot analyses), and a duplex nucleic acid that specifically binds with PCADM-1 polypeptide, e.g., PCADM-1 probe 1 (SEQ ID NO:5) and PCADM-1 probe 2 (SEQ ID NO:6), and double-stranded oligonucleotides that specifically bind with PCADM-1 having the sequence SEQ ID NO:7 and SEQ ID NO:8, all of which can be used to detect PCADM-1 using DNA/protein binding assays (e.g., Monte Carlo-like assay and EMSAs).

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLES

Example 1

Novel Assay for Identification of DNA Binding Proteins and the DNA Molecules that Specifically Bind Therewith The experiments presented in this example may be summarized as follows.

The invention relates to the development of a "proteomics" platform for rapid identification of double stranded DNA sequences, which preferentially bind protein(s), expressed in diseased tissue compared with benign or normal tissue from the same patient. The basic approach entails the systematic synthesis of 7 base pair, 8 base pair, and 9 base pair double stranded DNA sequences starting with the degenerate sequences and ending with "completed" sequences (see Table 2). A quantitative "DNA-protein" binding assay on a solid support (e.g., nylon membrane) is employed to assess 'DNA-protein' binding affinity and to identify the DNA sequence(s), which preferentially bind protein(s) from diseased tissue (i.e., cancer), compared to benign or normal tissue from the same patient, i.e., otherwise identical tissue known not to have any detectable disease, disorder or condition.

The invention field relates to identification of novel DNA sequences, which can uniquely bind protein(s) in diseased tissue and/or normal or benign tissue. The invention further relates to the diagnosis, prevention and treatment of diseases (including cancer) relating to dis-regulation (also referred to as mal-regulation or mal-expression) of nucleic acid expression.

The data disclosed herein demonstrate the discovery of a novel "Monte Carlo-like" assay for the identification of DNA binding proteins and the DNA molecule that specifically binds with the proteins.

The Materials and Methods used and the Results of the experiments presented in this example are now described.

The present invention discloses a novel rapid "quantitative" screening assay for identification of novel double-stranded oligonucleotides ranging in length from about 7 to 9 base pairs (also referred to as 7 to 9 base pairs) where the oligonucleotides bind a protein in a protein extract prepared using a tissue having a detectable disease, disorder or condition (i.e., cancer), but which oligonucleotides do not detectably bind with proteins obtained from otherwise identical tissue that does not demonstrate a disease, disorder or condition (i.e., normal or benign tissue).

The rationale for this approach is that these DNA sequence lengths represent the average length of known DNA sequences which normally bind transcription factors or co-factors involved in the regulation of gene expression in cells and tissue (Sambrook et al. 1989). Therefore, the "semi-random" screening for DNA sequences which bind protein over expressed in matching tissues from the same patient should identify novel DNA sequences which uniquely bind protein(s) involved in the regulation of gene transcription and gene expression associated with normal, benign or diseased tissue. However, the present invention is not limited to any particular length of oligonucleotide to be interrogated for DNA-binding ability. Thus, although oligonucleotides having a length of about 7 to 9 base pairs are exemplified herein, oligonucleotides having other lengths, including from having a length from about 7 to 16 base pairs (7-16 bps or 7-16 mers), are encompassed in the present invention.

The over-all import of the approach described here resides with the fact that identification of 7 base pair, 8 base pair or 9 base pair sequences (as the 7, 8, and 9 base pair oligonucleotides or oligomers, i.e., -mers, are alternatively referred to herein) associated with a specific pathological condition of the tissue will enable the use of these DNA sequences in the diagnosis of the patient's condition (i.e., as healthy, benign or diseased). That is, DNA-protein binding assays can be performed on protein obtained from tissue or body fluids to diagnose the patient's condition or disease status or normal status.

The present invention relates to the synthesis of either 7 base pair, 8 base pair or 9-mer double stranded DNA sequences, which selectively bind protein(s) from crude tissue extracts. The DNA sequences are synthesized and ($\gamma$ATP) $^{32}$P-radiolabeled and purified by column chromatography according to standard methods of Sambrook et al. (1989). Crude protein extracts were prepared from dissected human tissue of the same patient (i.e., normal, benign and cancer, and tissue not exhibiting in any detectable disease, disorder or condition) and increased amounts of protein (1, 5, 10 and 20 μg total protein) was applied to nylon membrane filters. The nylon membranes were then incubated using a constant amount of radiolabeled double stranded DNA and the filters were washed with phosphate buffer to remove non-specifically bound DNA and protein which failed to bind DNA according to established methods (Sambrook et al., 1987).

Table 1 provides an example of the DNA double stranded sequences (8 base pair) screened using the "Monte Carlo-like" array protocol disclosed herein. The amount of radiolabeled probe binding to crude protein extracts from different regions of a human prostate (i.e., prostate cancer, benign prostate hyperplasia, and prostate stroma) was compared for each sequence. Background levels (0 or zero) of radiolabeled probe binding to bovine serum albumin were measured for each probe. Routine screening for probes of interest was done in sequential rounds where the initial sequence had a core of 4N (i.e., random sequence). The sequence from this batch with the highest binding level was then used to generate 4 different sequences with a random unknown core sequence of 3N and the binding assays were repeated to identify the sequence with highest binding activity for the tissue site of interest (i.e., cancer in this case). Likewise, the sequence from this batch was subsequently selected and 4 sequences were produced having a core of 2N, 1N and zero N, respectively, useful to identify the sequence with highest binding activity for the tissue site of interest (i.e., cancer).

Once the sequence of interest (i.e., with sequentially increased levels of binding activity for the crude protein extract from prostate cancer) was identified, then experimental testing was carried out to verify the result. The data disclosed in Table 2 demonstrate for example, that the binding activity of a constant amount of radiolabeled probe (i.e., the ($\gamma$-ATP)$^{32}$P-labeled CACGGATG probe (1 ng at 100,000 cpm)) increased with increased amounts of crude protein (10 μg) from prostate cancer tissue spotted on a nylon membrane filter. The amount of probe binding to benign prostate hyperplasia, normal stroma and bovine serum albumin did not increase in comparable studies, however (Table 2). A degenerate probe (CANNNNTG) used as a control in these comparative assays failed to bind protein at levels above background levels of CACGGATG binding to bovine serum albumin (i.e., non-specific binding). Positive control studies with a known probe which, normally binds AP-2 confirmed that all the protein extracts were "good" and confirmed and that differences in the results were not attributable to how the protein was prepared or the methods used in the binding assays.

Finally, the selective binding of the probe identified was compared for comparable tissue extracts from multiple patient prostates (n=11) in order to verify the observation. The data disclosed herein confirm that the screening and selection strategy was successfully reduced to practice (Table 3).

Likewise, the data demonstrate that a specific double stranded DNA probe consistently bound a protein(s) associated with prostate cancer (Gleason Score 6-8).

An identical strategy and approach can be undertaken for the 7 base pair and 9 base pair sequences. The difference would be to start with core sequences of 3N and 5N, respectively.

TABLE 1

Screening of 8-mer oligonucleotide sequences

| Radiolabeled Probe | Prostate Cancer | Benign Prostate Hyperplasia |
|---|---|---|
| AANNNNTT | 0 | 0 |
| ATNNNNAT | +1 | 0 |
| AGNNNNCT | +1 | +1 |
| ACNNNNGT | +1 | +1 |
| TANNNNTA | 0 | 0 |
| TTNNNNAA | 0 | 0 |
| TGNNNNCA | 0 | 0 |
| TCNNNNGA | 0 | 0 |
| GANNNNTC | +2 | +2 |
| GTNNNNAC | +1 | +1 |
| GGNNNNCC | +1 | +1 |
| GCNNNNGC | +1 | +1 |
| *CANNNNTG | +3 | +1 |
| CTNNNNAG | +1 | 0 |
| CGNNNNCG | +1 | +1 |
| CCNNNNGG | +1 | +1 |
| *CACNNNTG | +3 | +1 |
| CAGNNNTG | +1 | +1 |
| CATNNNTG | +1 | +1 |
| CAANNNTG | +1 | 0 |
| *CACGNNTG | +4 | +1 |

TABLE 1-continued

Screening of 8-mer oligonucleotide sequences

| Radiolabeled Probe | Prostate Cancer | Benign Prostate Hyperplasia |
|---|---|---|
| CACCNNTG | +2 | +1 |
| CACTNNTG | +1 | +2 |
| CACANNTG | +3 | +1 |
| *CACGGNTG | +5 | +1 |
| CACGCNTG | +1 | +2 |
| CACGTNTG | +2 | +1 |
| CACGANTG | +2 | +1 |
| *CACGGATG | +6 | 0 |
| CACGGTTG | +3 | +1 |
| CACGGGTG | +2 | +1 |
| CACGGCTG | +2 | +1 |
| *CACGGATG | +6 | 0 |

Aliquots of the nuclear protein extracts (5, 10 and 20 μg protein total in triplicate test wells for each protein concentration) were dotted on Nylon membrane filters and incubated with the $(\gamma\text{-ATP})^{32}\text{P}$-labeled probe (1 nanogram at 100,000 counts per minute). Values were averaged for the triplicate measurements and then normalized for 10 μg protein from measurements of DNA binding to the 3 different protein concentrations tested. Control assays with a $(\gamma\text{-ATP})^{32}\text{P}$-labeled AP-2 binding probe (1 ng at 100,000 cpm) provided control measurements validating the quality of the protein extracts prepared and usually yielded counts of 100-5000 cpm (+1). The numbers represent: (0) <1000; (+1) 1000-5000; (+2) 5001-10,000; (+3) 10,001-20,000; (+4) 20,001-30,000; (+5) 30,001-40,000; (+6) 40,001-50,000 cpm. N=A, T, G, C.

TABLE 2

Measurements of CACGGATG binding to crude protein extracts (5/10/20 μg protein, respectively).

| Probe | Prostate Cancer | Benign Prostate Hyperplasia |
|---|---|---|
| CACGGATG | +3/+6/+13 | 0/+1/+1 |
| CANNNNTG | 0/+1/+1 | 0/0/+1 |
| AP-2 Probe | +1/+1/+1 | +1/+1/+1 |

See legend for Table 1 for methods.

TABLE 3

Measurements of CACGGATG binding to crude protein extract (10 μg protein) from 11 different prostates.

| Prostate Specimen | Probe | Prostate Cancer | Benign Prostate Hyperplasia |
|---|---|---|---|
| 1 | CACGGATG | +5 | 0 |
| 1 | CANNNNTG | +1 | 0 |
| 1 | AP-2 Probe | +1 | +1 |
| 2 | CACGGATG | +6 | +1 |
| 2 | CANNNNTG | +1 | +1 |
| 2 | AP-2 Probe | +1 | +1 |
| 3 | CACGGATG | +5 | 0 |
| 3 | CANNNNTG | +1 | +1 |
| 3 | AP-2 Probe | +1 | +1 |
| 4 | CACGGATG | +5 | 0 |
| 4 | CANNNNTG | +1 | +1 |
| 4 | AP-2 Probe | +1 | +1 |
| 5 | CACGGATG | +6 | +1 |
| 5 | CANNNNTG | 0 | 0 |
| 5 | AP-2 Probe | +1 | +1 |
| 6 | CACGGATG | +7 | +1 |
| 6 | CANNNNTG | 0 | +1 |
| 6 | AP-2 Probe | +1 | +1 |
| 7 | CACGGATG | +6 | +1 |
| 7 | CANNNNTG | 0 | +1 |
| 7 | AP-2 Probe | +1 | +1 |
| 8 | CACGGATG | +5 | +1 |
| 8 | CANNNNTG | 0 | +1 |
| 8 | AP-2 Probe | +1 | +1 |
| 9 | CACGGATG | +6 | +1 |
| 9 | CANNNNTG | +1 | 0 |
| 9 | AP-2 Probe | +1 | +1 |
| 10 | CACGGATG | +5 | 0 |
| 10 | CANNNNTG | +1 | +1 |
| 10 | AP-2 Probe | +1 | +1 |
| 11 | CACGGATG | +6 | +1 |
| 11 | CANNNNTG | +1 | 0 |
| 11 | AP-2 Probe | +1 | +1 |

See legend for Table 1 for methods.

Example 2

Identification of a Novel DNA Binding Protein, PCADM-1, and the DNA Molecules that Specifically Bind Therewith The experiments presented in this example may be summarized as follows.

The data disclosed herein demonstrate the discovery of a novel nucleic acid encoding a prostate cancer marker protein and a novel DNA molecule that specifically binds with the protein. These nucleic and amino acid sequences can be used to detect prostate cancer.

This invention relates to nucleic acid and amino acid sequences of DNA consensus domains, which, bind a novel marker protein for cancer, herein referred to as "PCADM-1" protein. The invention further relates to the use of these sequences and probes which specifically recognize the PCADM-1 protein in the diagnosis, prevention and treatment of diseases related to disregulated cell growth and proliferation and cancer.

The Materials and Methods used in the experiments presented in this example are now described.

A novel "Monte Carlo-like" type screening assay for identification of novel DNA binding proteins (i.e., transcription factors involved in chromosomal recombination) in nuclear extracts derived from dissected human prostate tissues was developed. For testing of oligonucleotides of 8 base pairs in length, each member of a set of stranded DNA sequences (n=4096 combinations as depicted in Table 1) was screened individual to assess protein binding by the oligonucleotide on nitrocellulose filters and in electrophoretic mobility gel shift assays (EMSAs).

Scintillation counting and phosphoimaging revealed that nuclear protein(s) from prostate cancer glands specifically bound a novel DNA sequence (CACGGATG [SEQ ID NO:5]), designated as "PCADM-1 probe 1." The CACGGATG sequence was very similar to known break point cluster region sequences (Rabbitts and Boehm, 1991, Advances in Immunology 50: 119-146) associated with chromosomal breakage in T-cells and B-cells.

In addition, the data disclosed herein also demonstrate that another double-stranded oligonucleotide (CACAATGA [SEQ ID NO:6]), designated "PCADM-1 probe 2", also bound specifically with PCADM-1. Thus, double-stranded oligonucleotides that specifically bind with PCADM-1 include the following:

```
"PCADM-1 probe 1" (SEQ ID NO: 5):
5'-CACGGATG-3'

3'-GTGCCTAC-5'

"PCADM-1 probe 2" (SEQ ID NO: 6)
5'-CACAATGA-3'

3'-GTGTTACT-5'
```

Utilization of a double stranded CACGGATG probe to screen cDNA libraries identified phagemid clones, which, expressed the "PCADM-1" protein. The recombinant protein was found to bind the presumptive CACGGATG (SEQ ID NO:5) other known break point cluster region sequences (Rabbitts and Boehm, ibid.) in EMSAs. EMSAs and ELISAs demonstrated that the over-expression of PCADM-1 protein in urine and serum was diagnostic and prognostic for human prostate cancer.

The PCADM-1 nucleic acid sequence is at least 99% homologous with that of the S2-ribosomal protein, and exhibiting at least 3 specific base pair mutations, which, render the PCADM-1 protein distinct from S2. In comparison, S2 is a totally different protein which is part of the ribosomal complex in normal cells and which does not appear to be present as a 'free entity' separate from ribosomal complexes in the cell or demonstrate any DNA binding activity. Accordingly, the data disclosed herein demonstrate, surprisingly, that even though S2 and PCADM-1 differ at only five amino acid residues, the two proteins demonstrate vastly different biological characteristics as exemplified and discussed elsewhere herein. More importantly, PCADM-1 is over expressed in prostate tumor cells and tissues and not found in normal cells and tissue. It should be noted that there are several reports demonstrating a connection between over-expression of mRNAs encoding ribosomal proteins and cancer (Chiao et al., 1992, Mol. Carcinog. 5: 219-231; Fernandez-Pol et al., 1993, J. Biol. Chem. 268: 21198-211204; Fernandez-Pol et al., 1994, Cell Growth & Differentiation 5: 821-825; Fernandez-Pol, 1996, Anticancer Res. 16: 2177-2186; Chan et al., 1996, Biochem. and Biophys. Res. Comm. 228: 141-147; Chan et al., 1996, Biochem. and Biophys. Res. Comm. 225: 952-956; Wool, 1996, Trends in Biochemical Sciences 21: 164-165; Wool, 1997, In: The ribosomal RNA and Group I introns, pp. 153-178, Green and Schroeder, eds., R.G. Landes Co., Austin, Tex.; Wool et al., 1995, Biochemistry & Cell Biology 73: 933-947; Vaarala et al., 1998, Int. J. Cancer 78: 27-32), indicating that increased numbers of ribosomal mRNAs are associated with the disease status.

For example, Northern blotting studies with the normal S2 mRNA revealed that the S2 mRNA was elevated in head and neck cancer, but barely detectable in normal tissue (Chaio and Tainsky, 1992, Mol. Carcinog. 5: 219-231). Without wishing to be bound by any particular theory, the wide spread belief is that the over expression of specific ribosomal proteins might somehow play an important role in cancer (Chiao et al., 1992, Mol. Carcinog. 5: 219-231; Fernandez-Pol et al., 1993, J. Biol. Chem. 268: 21198-211204; Fernandez-Pol et al., 1994, Cell Growth & Differentiation 5: 821-825; Fernandez-Pol, 1996, Anticancer Res. 16: 2177-2186; Chan et al., 1996, Biochem. and Biophys. Res. Comm. 228: 141-147; Chan et al., 1996, Biochem. and Biophys. Res. Comm. 225: 952-956; Wool, 1996, Trends in Biochemical Sciences 21: 164-165; Wool, 1997, In: The ribosomal RNA and Group I introns, pp. 153-178, Green and Schroeder, eds., R.G. Landes Co., Austin, Tex.; Wool et al., 1995, Biochemistry & Cell Biology 73: 933-947; Vaarala et al., 1998, Int. J. Cancer 78: 27-32).

One alternative possibility, without wishing to be bound by any particular theory, is that a putative "leucine zipper" sequence motifs or mutant motifs, characteristic of numerous ribosomal proteins, might be mutated and that the mutated "leucine zipper" domain can then bind to nucleic acids (Fernandez-Pol, 1996, Anticancer Res. 16: 2177-2186; Wool, 1996, Trends in Biochemical Sciences 21: 164-165; Wool, 1997, In: The ribosomal RNA and Group I introns, pp. 153-178, Green and Schroeder, eds., R.G. Landes Co., Austin, Tex.) and either function as a DNA binding protein, a nuclease, control ligation or regulate gene transcriptional and translational in cancer cells. For example, the rat ribosomal protein S3a is identical to the product of the rat v-fos transformation effector gene (Chan et al., 1996, Biochem. and Biophys. Res. Comm. 228: 141-147). S3a is involved in initiation of protein synthesis and is also related to proteins involved in the regulation of growth and the cell cycle (Chan et al., 1996, Biochem. and Biophys. Res. Comm. 228: 141-147). Likewise, the rat ribosomal protein L10 is homologous to a DNA-binding protein and to a putative Wilm's tumor suppressor gene (Chan et al., 1996, Biochem. and Biophys. Res. Comm. 225: 952-956). In sum, these studies suggest that mutant "ribosomal-like" proteins might be prognostic or diagnostic for cancer and play important roles in regulating chromosomal DNA activities, gene expression, and the behavior of cancer cells.

It should be understood that the present proteins, nucleotide sequences and methods described in this invention are not limited to the particular methodology, protocols, cell lines, vectors, reagents and applications described. These may vary. Likewise, it should be understood that the terminology used herein is strictly for the purpose of describing particular embodiments only, and is not intended to limit the scope of the present invention or applications. The scope of the invention is only limited by the appended claims.

Development of markers for the early detection of cancers such as prostate cancer is essential to improved treatment of cancer. With respect to prostate cancer, it is generally believed that serum prostate specific antigen (PSA) levels are neither sensitive nor specific for identification of patients with prostate cancer (Garnick, M. B. and Fair, W. R. Prostate Cancer. Scientific American, December 1998, 75-83). It has been estimated that only about 25% of men with prostate cancer are detected at serum PSA levels ranging from about greater than 4 ng/ml to 10 ng/ml (i.e., false negatives). Likewise, as many as 30% of men with benign prostate hyperplasia have elevated PSA levels (i.e., false positives). In addition, attempts to confirm the diagnosis with digital rectal exam are only successful in approximately 25% of patients and biopsies are only successful in 10% to 15% of the patients. Thus, development of more sensitive and more specific assays for cancers, including prostate cancer, is clearly needed. Non-invasive and inexpensive urine based screening assays, which would enable implementation through mass community screening programs, or in routine clinical examinations would be particularly useful.

The present invention relates to nucleic acid sequences, which can be used in screening assays to identify novel DNA binding proteins in nuclear extracts derived from human tissues. In one embodiment, the screening assay is useful in identifying novel transcription factors over-expressed in nuclear protein extracts of prostate tissue (i.e., glands). For this assay, 8 base pair double stranded DNA probes (n=4096) were designed. The DNA probes were then used to screen for differences in protein-DNA binding affinity among matched protein extracts from cancer, benign, high grade prostatic intraepithelial neoplasia, and seminal vesicle tissue in matched specimens from the same patient. Binding of the proteins was determined via measurements of the amount of DNA-protein binding observed on nitrocellulose filters and electrophoretic mobility gel shift assays (EMSAs).

Scintillation counting and phosphoimaging revealed that proteins isolated from nuclear extracts of advanced human prostate cancer tissues specifically bound a nucleic acid sequence comprising CACGGATG. Protein extracts from other tissues examined failed to bind this nucleic acid sequence. This sequence is similar differing by 1 base pair to known BPCR sequences (Rabbitts and Boehm, 1991, Advances in Immunology 50: 119-146) associated with chromosomal breakage in T-cells and B-cells.

The specific DNA sequence (CACGGATG) identified was employed to screen cDNA libraries developed from PC-3ML prostate cells (Wang et al., 1998, Oncology Research 10: 219-233, 1998). This screening resulted in the identification of phagemid clones, which expressed a PCADM-1 protein. Subcloning of the PCADM-1 gene showed that this gene exhibits approximately 99% homology with the chromosomal protein S2 and LLRep3. A nucleic acid sequence encoding this PCADM-1 protein (SEQ ID NO:1) is depicted in FIG. 1 along with the deduced amino acid sequence of this polypeptide (SEQ ID NO:2). This recombinant PCADM-1 protein was demonstrated to bind to the putative BPCR regions and known BPCRs in EMSAs.

The data disclosed herein demonstrate that "DNA-protein" binding assays utilizing EMSAs or nylon filter based binding assays have been developed for the identification of PCADM-1 in biological samples. Using EMSAs, PCADM-1 was detected in tissue extracts, and in urine and serum from human patients.

Polyclonal and monoclonal antibodies (i.e., IgG antibodies) were generated in rabbits and mice, respectively, using standard methods familiar to those schooled in the art of producing antibodies utilizing purified recombinant protein, in this case, PCADM-1, as an antigen.

Antibodies were characterized as being specific for the 33 kDa PCADM-1 antigen using Western dot blotting analysis, EIAs and immunostaining techniques according to standard methods familiar to those schooled in the art. The results disclosed herein demonstrate that the PCADM-1 antibody specifically recognizes PCADM-1 in recombinant plasmid protein extracts, in prostate tumor cell protein extracts and cells, and in urine and serum samples obtained from patients with prostate cancer.

Further, enzyme immuno-assays or EIAs with PCADM-1 specific antibodies demonstrated that the protein was a highly sensitive tissue marker for prostate cancer. As shown in Table 4, PCADM-1 is a significantly better prognostic and diagnostic marker for prostate cancer compared with PSA in prostate tissue extracts. In these experiments, nuclear protein extracts from microdissected regions of the prostate (n=40 radical prostatectomies examined) expressed significantly elevated levels of PCADM-1 compared to very low levels detected in matching seminal vesicle (SV), benign prostatic hyperplasia (BPH) or high grade prostatic intraepithelial neoplasm (HG-PIN) foci.

Further, the data disclosed herein demonstrate that the amounts of PCADM-1 (μg/mg DNA) increased as a function of the Gleason Score (GS) as described by Gleason et al., 1993, J. Urol. 149: 1568-1576.

In comparison, PSA levels (μg/mg DNA) were elevated in BPH, HGPIN, and GS specimens, but were significantly reduced in tissue extracts from GS 6, GS 7, and GS 8-10 foci. As disclosed in Table 4, the PSA levels in the tissue extracts were inversely proportional to the serum PSA levels (ng/ml) detected prior to prostatectomy. Serum PSA levels increased as a function of the Gleason Score (Table 0.4).

TABLE 4

PCADM-1 and PSA in microdissected tissues.

| Pathology | #Tissue PCADM-1 | #Tissue PSA | Serum PSA |
|---|---|---|---|
| SV (n = 30) | 0 | 0 | NA |
| SM (n = 5) | 0 | 0 | NA |
| BPH (n = 24) | 0 | 6.2 ± 0.7 | NA |
| HGPIN (n = 6) | 0.1 ± 0.03 | 3.1 ± 0.3 | NA |
| GS 4 (n = 8) | 1.8 ± 0.31 | 1.8 ± 0.31 | 5.5 ± 0.6 (5.5-12.8)* |
| GS 6 (n = 13) | 10.5 ± 1.15 | 0.5 ± 0.05 | 13.8 ± 7.9 (6.1-18.9)* |
| GS 7 (n = 10) | 20.3 ± 2.06 | 0.3 ± 0.02 | 11.5 ± 4.6 (8.9-43.3)* |

TABLE 4-continued

PCADM-1 and PSA in microdissected tissues.

| Pathology | #Tissue PCADM-1 | #Tissue PSA | Serum PSA |
|---|---|---|---|
| GS 8-10 (n = 9) | 25.2 ± 3.31 | 0.2 ± 0.01 | 15.5 ± 5.6 (9.5-87.0)* |

Note that following radical prostatectomy (n = 40 total), the different glandular foci and tissues were dissected from sagital sections of the prostates.
All BPH and HGPIN specimens came from the same prostates exhibiting cancer. Samples were assayed at least 3 times and the data were averaged for all the patients in the cohort studied.
*(range of PSA detected).
PCADM-1 and PSA levels (μg/mg DNA).
NA—not applicable.
All serum PSA measurements were from routine diagnostic tests taken upon examination of the patient by the Urologist and prior to radical prostatectomy.

Diagnostic tests were conducted to compare urine PCADM-1 levels with serum PSA levels in patients. Data from these tests are disclosed in Table 5.

TABLE 5

PCADM-1 urine assay (n = 227 total)

| Diagnosis | *PCADM-1 Positive | *PCADM-1 Negative |
|---|---|---|
| Prostate Cancer Biopsy positive: (GS 4-8) | 24/33 (6-13 ng/ml) | 9/33 |
| Post-Radical Prostatectomy | 2/14 (5-7 ng/ml) | 12/14 (<1 ng/ml) |
| BPH | 15/96 (2-8.3 ng/ml) | 81/96 (0.4-12 ng/ml) |
| Other Prostatic Disorders | 1/14 | 13/14 |
| Erectile Dysfunctions | 2/13 | 11/13 |
| Volunteers (22-53 yrs) | 0/40 | 40/40 |
| Women | 1/5 (neurogenic bladder) | 4/5 |
| Renal Cancer | 1/1 | 0/1 |
| Rectal Cancer | 0/2 | 2/2 |
| Infections/Inflammation | 5/9 | 4/9 |

Detection limit cut offs were:
*PCADM-1 positive (>0.2 ng/ml);
*PCADM-1 negative (<0.2 ng/ml).
The PCADM-1 levels ranged from 0.2-93 ng/l in PCADM-1 positive patients; and from 0-0.2 ng/ml in PCADM-1 negative patients.

The EIA studies on human urine were carried out with freshly collected urine or urine stored frozen according to methods familiar to those schooled in the art. In brief, the urine sample (100-200 μl) was applied to 96 well titer plates, the antigen allowed to attach for several hours, the plates washed with buffer, primary and secondary antibody were applied, and antibody detecting reagents were added, and the plates were read in a MicroTiter Plate ELISA reader (set at A450 nm) (BioRad, Hercules, Calif.).

As shown in Table 5, the sensitivity of the urine PCADM-1 assay was 73% (i.e., n=24/33) and correlated with the patients having elevated serum PSA levels and biopsy positive specimens (GS 4-8). Interestingly, in 2 patients with their prostates removed 3-4 years before the assay (i.e., GS 8-10, stage T3 cancers), the urine PCADM-1 levels were elevated and these patients also had elevated serum PSA levels (i.e., greater than about 5 ng/ml). These patients are currently under observation to determine whether there is recurring cancer. Conversely, 12 of these patients who, were negative for urine PCADM-1 (i.e. GS 5-6, stage T2 cancers) and they also had very low serum PSA values (<1 ng/ml).

In patients diagnosed with BPH (and no indication of cancer), about 16% (n=15/96) exhibited elevated PCADM-1 urine. Several (n=3/96) also had elevated serum PSA levels. In this cohort of patients, 84% (n=81/96) of the BPH patients were negative for PCADM-1. In these specimens n=40/96 (about 42%) also had low serum PSA levels (i.e. less than about 2 ng/ml). Of the 40 volunteer men, all were negative for PCADM-1 and had low serum PSA levels. Presumably, they were also negative for PSA. Interestingly, 1 patient with rectal cancer was positive for PCADM-1 and 5 patients (n=5/9) with infections or inflammation were positive for PCADM-1, indicating false positives might arise from infections or inflammation.

Thus, these data demonstrate that the sensitivity of the PCADM-1 urine assay is about 73% for prostate cancer. The overall specificity (i.e., total negative divided by total patients without the disease) was 167/194 or about 86%. Accordingly, the data disclosed herein demonstrate that PCADM-1 protein can be an independent diagnostic marker for cancer and, in particular, prostate cancer.

The present invention also relates to the screening assay and 8 base pair nucleic acid sequences identified, which, are capable of detecting PCADM-1. In one embodiment, the nucleic acid is a probe comprising the nucleic sequence of SEQ ID NO:5, and the sequence SEQ ID NO:6. Further, the double-stranded oligonucleotides having the sequence SEQ ID NO:7 and SEQ ID NO:8, also bind specifically with PCADM-1 and can be used to detect and assess the level of PCADM-1.

In one aspect of the present invention, nucleic acid sequences, which encode the PCADM-1 protein (SEQ ID NO:1), and the amino acid sequence of the PCADM-1 protein encoded by these nucleic acid sequences (SEQ ID NO:2) are provided. An exemplary nucleic acid sequence encoding the PCADM-1 protein (SEQ ID NO:1) and an exemplary deduced amino acid sequence (SEQ ID NO:2) is depicted in FIGS. 1A and 1B, respectively.

The present invention also relates to expression vectors and host cells containing expression vectors, which comprise these nucleic acid sequences. Expression vectors and host cells, which can be transfected with an expression vector, are well known in the art. Methods for incorporating a selected nucleic acid sequence such as that of the present invention into a vector and ultimately into a host cells are also well known.

The nucleic acid and amino acid sequences of the present invention are useful in developing screening assays for detection of PCADM-1 protein in biological samples. As demonstrated herein, in one embodiment, antibodies can be raised against the PCADM-1 protein and used in an immunoassay such as an EIA or ELISA to detect PCADM-1 protein in a biological sample such as tissue, sputum, urine or serum. Antibodies can be raised against this protein in accordance with well known procedures. Alternatively, labeled nucleic acid probes can be prepared from the nucleic acid sequences of the present invention and used in EMSAs to detect PCADM-1 in nuclear extracts of tissue biopsy samples.

Thus, another aspect of the present invention relates to methods and kits for detection of PCADM-1 in biological samples. As demonstrated herein, detection of PCADM-1 levels in a biological sample of a patient is useful in diagnosing and prognosticating prostate cancer or other cancers in the patient. In the method of the present invention a biological sample is obtained from a patient and then contacted with a means for detecting PCADM-1 in the biological sample. In one embodiment, this means the kit can comprise an antibody raised against the PCADM-1 protein, which is capable of detecting PCADM-1 protein in biological samples such as tissue, sputum, urine and serum. In another embodiment, this means the kit can comprise a labeled nucleic acid probe such as CACGGATG, which is capable of detecting PCADM-1 protein in biological samples such as tissue biopsies.

Accordingly in the kits of the present invention a means for detecting PCADM-1 protein in a sample and a PCADM-1 protein standard is provided. Means for detecting PCADM-1 protein may comprise an antibody raised against the PCADM-1 protein or a labeled nucleic acid probe capable of binding to the protein. The presence of PCADM-1 in the biological sample is indicative of the patient having prostate cancer. Methods and kits of the present invention can also be used in patients with prostate cancer to assess their prognosis and evaluate treatments by monitoring changes in levels of PCADM-1 in the patient over time. Increases in the level of PCADM-1 over time is indicative of the cancer progressing while decreases in the level of PCADM-1 over time is indicative of regression of the cancer.

Further, it is believed that these methods and kits for detecting PCADM-1 protein levels may also be useful in diagnosing and prognosticating other types of cancer, inflammatory conditions, infections and genetic mutations.

Example 3

Modulation of PCADM-1 Expression Using Enzymatic Nucleic Acids and Treatment of Diseases, Disorders or Conditions Associated with PCADM-1 Expression The experiments presented in this example may be summarized as follows.

The prostate cancer antigen diagnostic marker 1 (PCADM-1) is a 33 kDa cytoplasmic protein, which, as more fully disclosed elsewhere previously herein, is over-expressed in human prostate cancer tissue and is detected in the urine of patients afflicted with prostate cancer. Without wishing to be bound by any particular theory, expression of PCADM-1 can convey a selective growth and/or survival advantage to tumor cells and/or cause chromosomal alteration(s), which lead to the development of prostate cancer or other cancers. That is, the data disclosed elsewhere herein suggest that increased expression of PCADM-1, compared with the level of expression in a tissue known not to have a disease or condition, is correlated with, associated with, and/or can mediate a disease or condition, e.g., prostate cancer. Therefore, therapeutic strategies based on modulation of PCADM-1 expression, which can potentially inhibit or reduce the aberrant (i.e., increased) expression of PCADM-1, were examined as potential anti-cancer therapies. The data disclosed herein demonstrate the use of a PCADM-1 specific PCADM-1 DNAZYM, designated PCADM-1 DNAZYM-1 (SEQ ID NO:9), to inhibit PCADM-1 expression and the significant therapeutic effects related thereto.

The Materials and Methods used in and the Results of the experiments presented in this example are now described.
Selection of PCADM-1 DNAZYM Cleavage Site in Human PCADM-1 RNA Targets for useful DNA enzyme can be determined as disclosed in Draper et al., WO 93/23569; Sullivan et al., WO 93/23057; Thompson et al., WO 94/02595; Draper et al., WO 95/04758; McSwiggen et al., U.S. Pat. No. 5,525,468, and hereby incorporated by reference herein in their totality. Rather than repeat the guidance provided in those documents here, below are provided specific examples of such methods, not limited to those in the art or to be developed in the future.

DNAZYMs to such target mRNAs were designed as described in those applications and were synthesized to be tested in vitro and in vivo, as also described in standard treatises. DNAZYMs can also be optimized and delivered as described therein.

To test whether the sites predicted by the computer-based RNA folding algorithm corresponded to accessible sites in PCADM-1 mRNA, PCADM-1 DNAZYM target sites were selected by analyzing cDNA sequences of human PCADM-1 and prioritizing the cleavage sites on translational initiation site of PCADM-1 gene.

PCADM-1 DNAZYMs were designed that could bind each target and were individually analyzed by computer folding (Christoffersen et al., 1994 J. Mol. Struc. Theochem. 311: 273; Jaeger et al., 1989, Proc. Natl. Acad. Sci. USA, 86:7706; Jaeger et al., 1989, RNA 2: 419-428) to assess whether the PCADM-1 DNAZYM sequences fold into the appropriate secondary structure. The PCADM-1 DNAZYMs with unfavorable intramolecular interactions between the binding arms and the catalytic core were eliminated from consideration. As noted below, varying binding arm lengths can be chosen to optimize activity. Generally, at least 8 to 10 bases on each arm flanking a catalytic core are sufficient for binding to, or otherwise interacting with, the target mRNA.

Optimizing PCADM-1 DNAZYM-1 Activity

The proliferation and survival of PC-3 ML was inhibited by the direct addition of chemically stabilized DNAZYMs. Presumably, and without wishing to be bound by any particular theory, DNAZYM uptake was mediated by passive diffusion of the anionic nucleic acid across the cell membrane. In this case, efficacy can be greatly enhanced by directly coupling a ligand to the DNAZYM. The DNAZYMs can be delivered to the cells by receptor-mediated uptake. Using such conjugated adducts, cellular uptake can be increased by several orders of magnitude without having to alter the phosphodiester linkages necessary for PCADM-1 DNAZYM cleavage activity.

Alternatively, DNAZYMs can be administered to cells using a variety of methods known to those familiar to the art, including, but not restricted to, antennapae peptide coupled DNAZYM delivery, encapsulation in liposomes, by ionophoresis, or by incorporation into other vehicles, as well as hydrogels, cyclodextrins, biodegradable nanocapsules, and bioadhesive microspheres. The DNA/vehicle combination is delivered locally by direct injection or by use of a needle, catheter, infusion pump or stent. Alternative routes of delivery include, but are not limited to, intramuscular injection, aerosol inhalation, oral (tablet or pill form), topical, systemic, ocular, intraperitoneal and/or intrathecal delivery. More detailed descriptions of DNAZYM delivery and administration are provided in Sullivan, et al., WO 93/23057, and Draper et al., WO 95/04818, which have been incorporated by reference herein.

Chemical Modification

PCADM-1 DNAZYM sequences and PCADM-1 DNAZYM-1 motifs described in this invention are meant to be non-limiting examples, and those skilled in the art will recognize that other modifications (base, sugar and phosphate modifications) to enhance nuclease stability of a PCADM-1 DNAZYM can be readily generated using standard techniques and are hence within the scope of this invention.

Use of DNAZYMs Targeting PCADM-1

Figure 4:
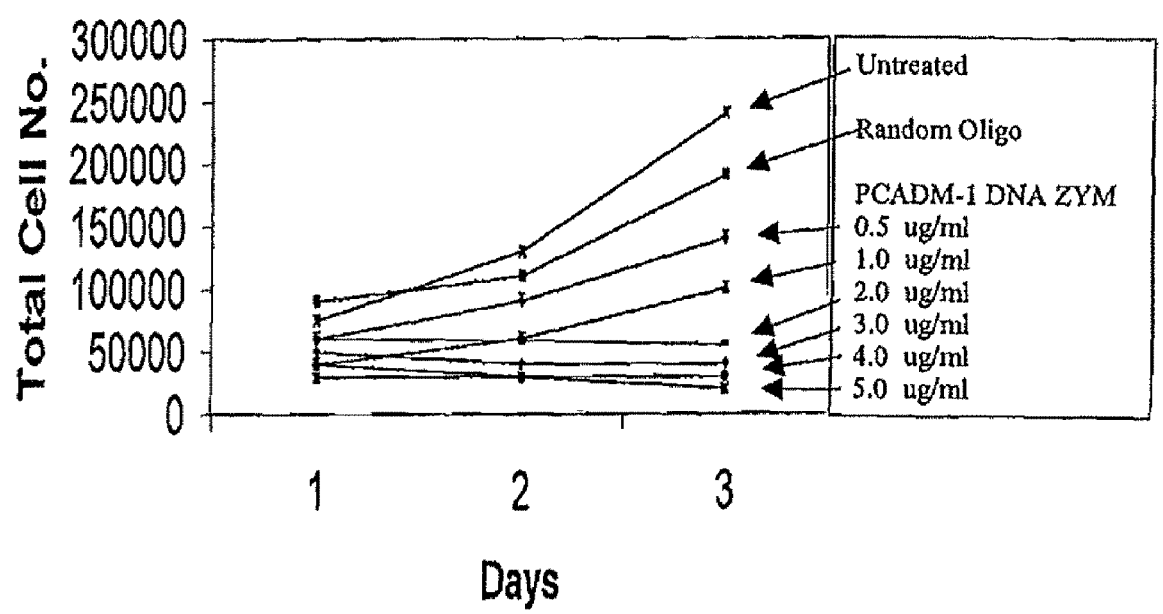
FIG. 4 is a graph depicting cell survival curves after 1-3 days for PC-3 ML cells. Legend on the Y axis (far left) corresponds to the curves (from top to bottom) showing the influence on cell growth of untreated cells, cells treated with a random oligonucleotide (5 μg/ml), or with PCADM-1 DNAZYM-1 at 0.5, 1.0, 2.0, 3.0, 4.0 and 5.0 μg/ml, respectively.

The data disclosed herein demonstrate that increased expression of PCADM-1 is associated with prostate cancer. Further, the data disclosed herein demonstrate that inhibition of PCADM-1 expression (for example using DNAZYMs) reduced cell proliferation of a number of prostate tumor cell lines, both in vitro and in vivo. Further, the data disclosed herein demonstrate that inhibition of PCADM-1 expression, such as, but not limited to, using a DNAZYM, reduce the proliferative potential of prostate tumor cell lines, while inducing cell death (i.e., greater than about 80% PC-3 ML cell death by 48-72 hours) (FIG. 4).

DNAZYMs, with their catalytic activity and increased site specificity, represent a potent and safe therapeutic molecule for the treatment of cancer. In the present invention, PCADM-1 DNAZYM-1 (SEQ ID NO:9) did not inhibit smooth muscle, fibroblast, or normal prostate epithelial cell survival or proliferation. However, PCADM-1 DNAZYM-1, in combination with VEGF-1 and MMP-2 DNAZYMs administered locally, inhibited growth and/or eradicated human prostate PC-3 ML cell tumor growth in vivo in SCID mice (n=45/50 mice tumors treated over 2-3 months) for a 90% response rate.

In control experiments, where mice were untreated or treated with a random oligonucleotide greater than 75% of the mice grew large tumors over a similar time frame. In experiments where the PCADM-1 DNAZYM-1 was administered as a single agent, i.v. via the tail vein, PCADM-1 DNAZYM-1 inhibited PC-3 ML tumor growth of PC-3 ML cells injected i.v. (n=12/13 mice) for a 92% success rate. The untreated mice (n=9/9) and control mice to which a random oligonucleotide was administered all (n=5/5) developed numerous metastatic nodules over a 2 month interval. In all these experiments, mouse survival rates increased from 0% to greater than about 80% to 92% over the 2-3 month treatment intervals for treated mice.

These data demonstrate that PCADM-1 DNAZYM-1 can be delivered in a similar fashion to cancer cells in patients and can inhibit their proliferation and survival and metastases. Thus, these data indicate that a PCADM-1 DNAZYM-1 can be used in conjunction with existing cancer therapies and physical treatments (e.g., cryoablation and radiation treatment), or by itself, to improve overall patient survival rates.

Again, the data disclosed herein demonstrate that administering DNAZYMs that specifically cleave RNA encoding other proteins, e.g., VEGF-1 and MMP-2, further increased the therapeutic effect of administering PCADM-1 DNAZYM with localized delivery. Thus, the present invention encompasses methods where PCADM-1 DNAZYMs are co-administered with other DNA enzymes that cleave RNAs encoding proteins such as growth factors and the like.

Diagnostic Uses

DNAZYMs of this invention provide diagnostic tools to examine genetic drift and mutations within diseased cells or to detect the presence of PCADM-1 RNA in a cell, tissues or body fluids. The close relationship between DNAZYM activity and the structure of the target RNA allows the detection of mutations in any region of the molecule, which alters the base-pairing and three-dimensional structure of the target RNA. By using multiple DNAZYM targeting the PCADM-1 mRNA, one can map nucleotide changes which are important to RNA structure and function in vitro, as well as in cells and tissues. Cleavage of target RNAs with DNAZYMs can be used to inhibit gene expression and define the role of specified gene products in the progression of disease. In this manner, other genetic targets can be defined as important mediators of the disease. These experiments can lead to better treatment of the disease progression by providing potential combination therapies (e.g., multiple DNA enzymes targeted to different genes, DNA enzymes coupled with known small molecule inhibitors, or intermittent treatment with combinations of DNA enzymes and/or other chemical or biological molecules).

Other in vitro uses of DNA enzymes of this invention are well known in the art, and include detection of the presence of mRNAs associated with PCADM-1 related condition. Such RNA is detected by determining the presence of a cleavage product after treatment with a PCADM-1 DNAZYMs using standard methodology.

Effect of Cell Survival of PCADM-1 mRNA Expression

Cell survival curves after 1-3 days in culture demonstrated that transient transfection overnight with PCADM-1 DNAZYM-1 (SEQ ID. NO:9) at increased concentrations (0.5 to 5 µg/ml) (FIG. 4) inhibited growth of PC-3 ML cells (FIG. 4). Control experiments with a random oligonucleotide failed to detectably affect PC-3 ML cell growth (FIG. 4). Similar experiments using NPTX-1532 cells treated with a control non-specific PCADM-1 DNAZYM (i.e., DNAZYM-11) failed to inhibit cell growth or cell survival. These data demonstrate that PCADM-1 DNAZYMs are powerful therapeutics for the inhibition of prostate cancer cell growth and survival and clearly demonstrate that PCADM-1 expression is associated with and/or mediates, among other things, prostate cancer and/or proliferation and/or growth of cancer cells.

Example 4

Diagnostic Use of Antibodies for PCADM-1-Related Proteins

The data disclosed herein demonstrate that PCADM protein of the present invention shares a high degree of homology with ribosomal S2 protein, i.e., about 98% amino acid sequence homology. Accordingly, anti-S2 antibodies can be used as a diagnostic agent for prostate cancer in an antibody-based assay according to the present invention. Antibodies to the S2 protein described in the present specification can be produced according to methods well-known to those of skill in the art.

In a further embodiment of the present invention, anti-S2 antibodies can be used in an antibody-based urine assay for prostate cancer, wherein the anti-S2 antibody is used to detect PCADM-1, as more fully set forth elsewhere herein.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of diagnosing prostate cancer in a mammal, said method comprising obtaining a biological sample from said mammal, assessing the level of polynucleotide encoding PCADM-1 in said biological sample, and comparing the level of polynucleotide encoding PCADM-1 in said biological sample with the level of polynucleotide encoding PCADM-1 in a biological sample obtained from a like mammal not afflicted with prostate cancer, wherein a higher level of polynucleotide encoding PCADM-1 in said biological sample from said mammal compared with the level of polynucleotide encoding PCADM-1 in said biological sample from said like mammal is an indication that said mammal is afflicted with prostate cancer, thereby diagnosing prostate cancer in said mammal, wherein the sequence of the polynucleotide encoding PCADM-1 comprises the polynucleotide sequence set forth in SEQ ID NO:1.

2. The method of claim 1, wherein said mammal is selected from the group consisting of a human and a dog.

3. The method of claim 1, wherein said biological sample is selected from the group consisting of a prostate tissue sample, a blood sample, a urine sample, a sputum sample, a peritoneal cavity fluid sample, a perineal cavity fluid sample, a pleural cavity fluid sample, a semen sample, a prostatic fluid sample, a stool sample, and a bone marrow sample.

4. A kit for detecting a polynucleotide encoding prostate cancer antigen diagnostic marker 1 (PCADM-1) in a mammal, said kit comprising a molecule that specifically binds with nucleic acid encoding PCADM-1, said kit further comprising an applicator, and an instructional material for the use thereof, wherein the sequence of the nucleic acid encoding PCADM-1 comprises the polynucleotide sequence of SEQ ID NO:1.

5. The kit of claim 4, wherein said mammal is selected from the group consisting of a dog and a human.

6. The kit of claim 4, wherein said molecule that specifically binds with a nucleic acid encoding PCADM-1 is selected from the group consisting of a nucleic acid complementary with a nucleic acid sharing greater than 99% sequence identity with sequence SEQ ID NO: 1.

* * * * *

SEQUENCE LISTING

<160> NUMBER OF SEQ ID NOS: 10

<210> SEQ ID NO 1
<211> LENGTH: 914
<212> TYPE: DNA

<213> ORGANISM: Homo sapiens

<400> SEQUENCE: 1

```
gcacgaggga tgacgccggt gcagcggggg ggcccggggg ccctggtggc cctgggatgg      60
ggaaccgcgg tggcttccgc ggaggtttcg gcagtggcat ccggggccgg ggtcgcggcc     120
gtggacgggg ccggggccga ggccgcggag ctcgcggagg caaggccgag gataaggagt     180
ggatgcccgt caccaagttg ggccgcttgg tcaaggacat gaagatcaag tccctggagg     240
agatcactct cttctccctg cccattaagg aatcagagat cattgatttc ttcctggggg     300
cctctctcaa ggatgaggtt ttgaagatta tgccagtgca gaagcagacc cgtgccggcc     360
agcgcaccag gttcaaggca tttgttgcta tcggggacta caatggccac gtcggtctgg     420
gtgttaagtg ctccaaggag gtggccaccg ccatccgtgg ggccatcatc ctggccaagc     480
tctccatcgt ccccgtgcgc agaggctact gggggaacaa catcggcaag gcccacactg     540
tccgttgcaa ggtgacaggc cgctgcggct ctgtgctggt acgcctcatc cctgcaccca     600
ggggcactgg catcgtctcc gcacctgtgc ctaagaagct gctcatgatg gctggtatcg     660
atgactgcta cacctcagcc cggggctgca ctgccaccct gggcaacttc accaaggcca     720
cctttgatgc catttctaag acctacagct acctgacccc cgacctctgg aaggagactg     780
tattcaccaa gtctccctat caggagttca ctgaccacct cgtcaagacc cacaccagag     840
tctccgtgca gcggactcag gctccagctg tggctacaac atagggtttt tatacccaag     900
aaaagaaaaa taaa                                                       914
```

<210> SEQ ID NO 2
<211> LENGTH: 275
<212> TYPE: PRT
<213> ORGANISM: Homo sapiens

<400> SEQUENCE: 2

```
Met Gly Asn Arg Gly Gly Phe Arg Gly Gly Phe Gly Ser Gly Ile Arg
  1               5                  10                  15

Gly Arg Gly Arg Gly Arg Gly Arg Gly Arg Gly Arg Gly Arg Gly Ala
                 20                  25                  30

Arg Gly Gly Lys Ala Glu Asp Lys Glu Trp Met Pro Val Thr Lys Leu
             35                  40                  45

Gly Arg Leu Val Lys Asp Met Lys Ile Lys Ser Leu Glu Glu Ile Thr
         50                  55                  60

Leu Phe Ser Leu Pro Ile Lys Glu Ser Glu Ile Ile Asp Phe Phe Leu
 65                  70                  75                  80

Gly Ala Ser Leu Lys Asp Glu Val Leu Lys Ile Met Pro Val Gln Lys
                 85                  90                  95

Gln Thr Arg Ala Gly Gln Arg Thr Arg Phe Lys Ala Phe Val Ala Ile
            100                 105                 110

Gly Asp Tyr Asn Gly His Val Gly Leu Gly Val Lys Cys Ser Lys Glu
        115                 120                 125

Val Ala Thr Ala Ile Arg Gly Ala Ile Ile Leu Ala Lys Leu Ser Ile
    130                 135                 140

Val Pro Val Arg Arg Gly Tyr Trp Gly Asn Asn Ile Gly Lys Ala His
145                 150                 155                 160

Thr Val Arg Cys Lys Val Thr Gly Arg Cys Gly Ser Val Leu Val Arg
                165                 170                 175

Leu Ile Pro Ala Pro Arg Gly Thr Gly Ile Val Ser Ala Pro Val Pro
            180                 185                 190
```

```
Lys Lys Leu Leu Met Met Ala Gly Ile Asp Asp Cys Tyr Thr Ser Ala
        195                 200                 205

Arg Gly Cys Thr Ala Thr Leu Gly Asn Phe Thr Lys Ala Thr Phe Asp
        210                 215                 220

Ala Ile Ser Lys Thr Tyr Ser Tyr Leu Thr Pro Asp Leu Trp Lys Glu
225                 230                 235                 240

Thr Val Phe Thr Lys Ser Pro Tyr Gln Glu Phe Thr Asp His Leu Val
            245                 250                 255

Lys Thr His Thr Arg Val Ser Val Gln Arg Thr Gln Ala Pro Ala Val
            260                 265                 270

Ala Thr Thr
        275

<210> SEQ ID NO 3
<211> LENGTH: 13
<212> TYPE: DNA
<213> ORGANISM: Homo sapiens

<400> SEQUENCE: 3
gggggggggg ggg                                                              13

<210> SEQ ID NO 4
<211> LENGTH: 13
<212> TYPE: DNA
<213> ORGANISM: Homo sapiens

<400> SEQUENCE: 4
gggggggggg ggg                                                              13

<210> SEQ ID NO 5
<211> LENGTH: 8
<212> TYPE: DNA
<213> ORGANISM: artificial sequence
<220> FEATURE:
<223> OTHER INFORMATION: double-stranded PCAM-1 binding oligonucleotide

<400> SEQUENCE: 5 cacggatg                                                                     8

<210> SEQ ID NO 6
<211> LENGTH: 8
<212> TYPE: DNA
<213> ORGANISM: Artificial Sequence
<220> FEATURE:
<223> OTHER INFORMATION: double-stranded PCAM-1 binding oligonucleotide

<400> SEQUENCE: 6 cacaatga                                                                     8

<210> SEQ ID NO 7
<211> LENGTH: 7
<212> TYPE: DNA
<213> ORGANISM: Artificial Sequence
<220> FEATURE:
<223> OTHER INFORMATION: double-stranded PCAM-1 binding oligonucleotide

<400> SEQUENCE: 7 cacaatg                                                                      7

<210> SEQ ID NO 8
<211> LENGTH: 14
<212> TYPE: DNA
<213> ORGANISM: Artificial Sequence
<220> FEATURE:
```

```
<223> OTHER INFORMATION: double-stranded PCAM-1 binding oligonucleotide

<400> SEQUENCE: 8
cacaatgttt ttgt                                                              14

<210> SEQ ID NO 9
<211> LENGTH: 31
<212> TYPE: DNA
<213> ORGANISM: Artificial Sequence
<220> FEATURE:
<223> OTHER INFORMATION: enzymatic nucleic acid (PCAM-1) rybozyme

<400> SEQUENCE: 9
gatcttcagg ctagctacaa cgagtccttg a                                           31

<210> SEQ ID NO 10

<400> SEQUENCE: 10

000
```